(12) United States Patent
Kawata et al.

(10) Patent No.: US 8,563,740 B2
(45) Date of Patent: Oct. 22, 2013

(54) OXADIAZOLE DERIVATIVE, AND LIGHT-EMITTING ELEMENT, LIGHT-EMITTING DEVICE, ELECTRONIC DEVICE, AND LIGHTING DEVICE USING THE OXADIAZOLE DERIVATIVE

(75) Inventors: Yuko Kawata, Kanagawa (JP); Hiroshi Kadoma, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 22 days.

(21) Appl. No.: 13/297,937

(22) Filed: Nov. 16, 2011

(65) Prior Publication Data
US 2012/0130081 A1 May 24, 2012

(30) Foreign Application Priority Data
Nov. 18, 2010 (JP) .................. 2010-257739

(51) Int. Cl.
*C07D 271/10* (2006.01)
(52) U.S. Cl.
USPC .......................... 548/145; 428/690
(58) Field of Classification Search
USPC .......................... 428/690; 548/143
See application file for complete search history.

(56) References Cited

U.S. PATENT DOCUMENTS

| 7,906,228 B2 * | 3/2011 | Lee et al. ................. 428/690 |
| 2007/0149784 A1 | 6/2007 | Murata et al. |
| 2007/0222376 A1 | 9/2007 | Ohsawa et al. |

FOREIGN PATENT DOCUMENTS

JP 2008-311480 12/2008

OTHER PUBLICATIONS

Baldo, M.A. et al, "Very High-Efficiency Green Organic Light-Emitting Devices Based on Electrophosphorescence," Applied Physics Letters, vol. 75, No. 1, Jul. 5, 1999, pp. 4-6.

* cited by examiner

*Primary Examiner* — Yong Chu
(74) *Attorney, Agent, or Firm* — Husch Blackwell LLP

(57) ABSTRACT

An object of one embodiment of the present invention is to provide a novel oxadiazole derivative as a substance having high excitation energy, in particular, a substance having high triplet excitation energy. One embodiment of the present invention is an oxadiazole derivative represented by General Formula (G1) below.

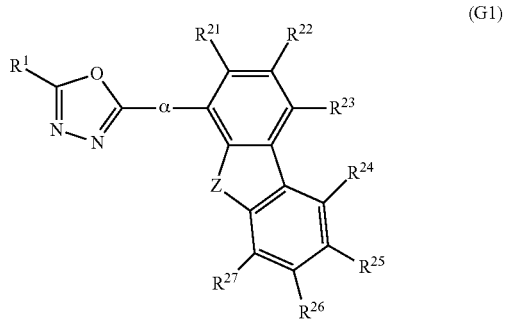

In General Formula (G1), $R^1$ represents either an alkyl group having 1 to 4 carbon atoms or a substituted or unsubstituted aryl group having 6 to 13 carbon atoms. In General Formula (G1), $R^{21}$ to $R^{27}$ separately represent any one of a hydrogen atom, an alkyl group having 1 to 4 carbon atoms, and a substituted or unsubstituted aryl group having 6 to 13 carbon atoms. In General Formula (G1), α represents a substituted or unsubstituted arylene group having 6 to 13 carbon atoms. In General Formula (G1), Z represents either a sulfur atom or an oxygen atom.

13 Claims, 23 Drawing Sheets

OXADIAZOLE DERIVATIVE, AND LIGHT-EMITTING ELEMENT, LIGHT-EMITTING DEVICE, ELECTRONIC DEVICE, AND LIGHTING DEVICE USING THE OXADIAZOLE DERIVATIVE

BACKGROUND OF THE INVENTION

1. Field of the Invention

The present invention relates to an oxadiazole derivative, and a light-emitting element, a light-emitting device, an electronic device, and a lighting device each using the oxadiazole derivative.

2. Description of the Related Art

In recent years, research and development have been extensively conducted on light-emitting elements utilizing electroluminescence (EL). In the basic structure of such a light-emitting element, a layer containing a light-emitting substance is interposed between a pair of electrodes. By voltage application to this element, light emission from the light-emitting substance can be obtained.

Since such light-emitting elements are self-luminous elements, it has advantages over liquid crystal displays in having high pixel visibility and eliminating the need for backlights, for example; thus, light-emitting elements are thought to be suitable for flat panel display elements. Light-emitting elements are also highly advantageous in that they can be thin and lightweight. Furthermore, very high speed response is also one of the features of such elements.

Furthermore, since such light-emitting elements can be formed in a film form, they make it possible to provide planar light emission; thus, large-area elements utilizing planar light emission can be easily fowled. This is a difficult feature to obtain with point light sources typified by incandescent lamps and LEDs or linear light sources typified by fluorescent lamps. Thus, light-emitting elements also have great potential as planar light sources applicable to lighting devices and the like.

Light-emitting elements utilizing electroluminescence are broadly classified according to whether they use an organic compound or an inorganic compound as a light-emitting substance. In the case where an organic compound is used as a light-emitting substance, by application of voltage to a light-emitting element, electrons and holes are injected into a layer containing the light-emitting organic compound from a pair of electrodes, whereby current flows. Then, these carriers (i.e., electrons and holes) are recombined, whereby the light-emitting organic compound is excited. The light-emitting organic compound returns to the ground state from the excited state, thereby emitting light. Note that the excited state of an organic compound can be a singlet excited state or a triplet excited state, and luminescence from the singlet excited state (S*) is referred to as fluorescence, and luminescence from the triplet excited state (T*) is referred to as phosphorescence. The statistical generation ratio thereof in a light-emitting element is considered to be S*:T*=1:3.

At room temperature, a compound that is capable of converting energy of a singlet excited state into luminescence (hereinafter, referred to as a fluorescent compound) exhibits only luminescence from the singlet excited state (fluorescence), not luminescence from the triplet excited state (phosphorescence). Thus, the internal quantum efficiency (the ratio of generated photons to injected carriers) of a light-emitting element using a fluorescent compound is assumed to have a theoretical limit of 25% on the basis of S*:T*=1:3.

In contrast, with a compound that can convert energy of a triplet excited state into luminescence (hereinafter, called a phosphorescent compound), the internal quantum efficiency can be increased to 75% to 100% in theory. In other words, an element using a phosphorescent compound can have three to four times as high emission efficiency as that of an element using a fluorescent compound. For these reasons, a light-emitting element using a phosphorescent compound has been actively developed in recent years in order to achieve a highly-efficient light-emitting element (e.g., see Non-Patent Document 1).

When formed using the above-described phosphorescent compound, a light-emitting layer of a light-emitting element is often formed such that a phosphorescent compound is dispersed in a matrix of another compound in order to suppress concentration quenching or quenching due to triplet-triplet annihilation in the phosphorescent compound. Here, the substance serving as a matrix is called a host material, and the substance dispersed in a matrix, such as a phosphorescent compound, is called a guest material.

A host material needs to have higher triplet excitation energy (an energy difference between a ground state and a triplet excited state) than a phosphorescent compound in the case where the phosphorescent compound is a guest material. In addition, the host material needs to have a carrier transport property by which desired carrier balance can be controlled in a light-emitting layer. With the use of such a host material, characteristics of a light-emitting element can be improved.

REFERENCE

[Non-Patent Document 1] M. A. Baldo, and four others, *Applied Physics Letters*, vol. 75, No. 1, 4-6 (1999)

SUMMARY OF THE INVENTION

A novel oxadiazole derivative is provided as a substance having high excitation energy, in particular, a substance having high triplet excitation energy. A novel oxadiazole derivative having a high electron-transport property is provided. By applying the novel oxadiazole derivative to a light-emitting element, element characteristics of the light-emitting element are improved. A light-emitting device, an electronic device, and a lighting device each having low power consumption and low driving voltage are provided.

One embodiment of the present invention is an oxadiazole derivative represented by General Formula (G1) below.

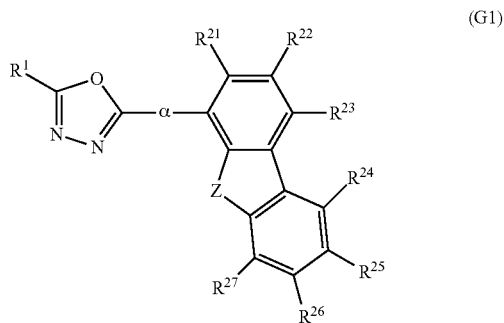

(G1)

In General Formula (G1), $R^1$ represents either an alkyl group having 1 to 4 carbon atoms or a substituted or unsubstituted aryl group having 6 to 13 carbon atoms. In General Formula (G1), $R^{21}$ to $R^{27}$ separately represent any one of a hydrogen atom, an alkyl group having 1 to 4 carbon atoms, and a substituted or unsubstituted aryl group having 6 to 13 carbon atoms. In General Formula (G1), α represents a substituted or unsubstituted arylene group having 6 to 13 carbon atoms. In General Formula (G1), Z represents either a sulfur atom or an oxygen atom.

One embodiment of the present invention is an oxadiazole derivative represented by General Formula (G2) below.

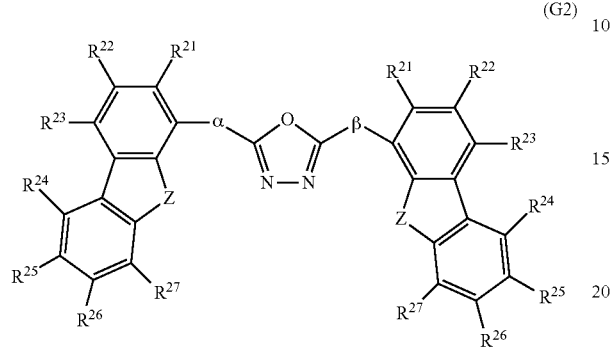

(G2)

In General Formula (G2), $R^{21}$ to $R^{27}$ separately represent any one of a hydrogen atom, an alkyl group having 1 to 4 carbon atoms, and a substituted or unsubstituted aryl group having 6 to 13 carbon atoms. In General Formula (G2), α and β separately represent a substituted or unsubstituted arylene group having 6 to 13 carbon atoms. In General Formula (G2), Z represents either a sulfur atom or an oxygen atom.

One embodiment of the present invention is an oxadiazole derivative in which α and β in General Formulae (G1) and (G2) separately represent either a substituted or unsubstituted phenylene group or a substituted or unsubstituted biphenyldiyl group.

One embodiment of the present invention is an oxadiazole derivative in which α and β in General Formulae (G1) and (G2) separately represent a substituted or unsubstituted phenylene group.

One embodiment of the present invention is an oxadiazole derivative in which α and β in General Formulae (G1) and (G2) separately represent any one of structures represented by Structural Formulae (I-1) to (1-15) below.

(I-1)

(1-2)

(1-3)

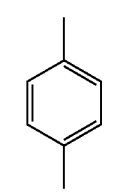

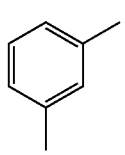

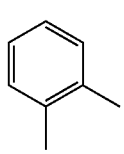

-continued (1-4)

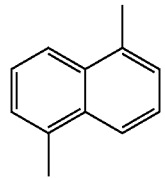

(1-5)

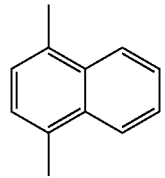

(1-6)

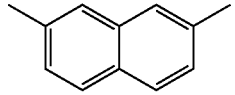

(1-7)

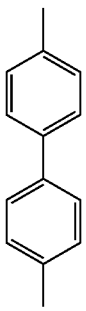

(1-8)

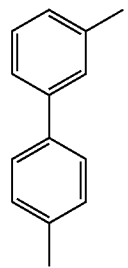

(1-9)

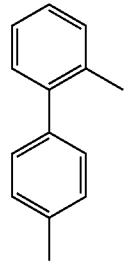

(1-10)

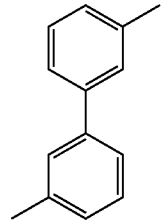

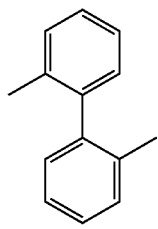
(1-11)

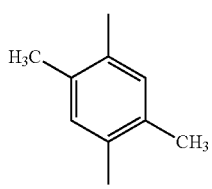
(1-12)

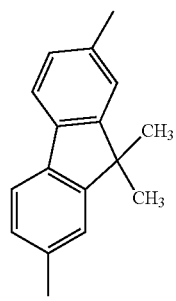
(1-13)

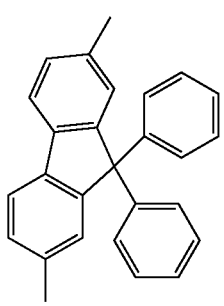
(1-14)

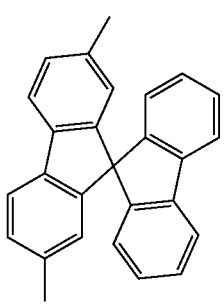
(1-15)

One embodiment of the present invention is an oxadiazole derivative represented by General Formula (G1-1) below.

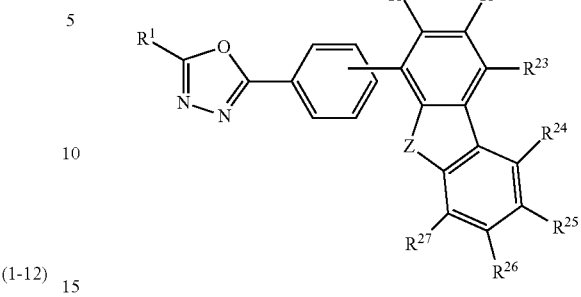
(G1-1)

In General Formula (G1-1), $R^1$ represents either an alkyl group having 1 to 4 carbon atoms or a substituted or unsubstituted aryl group having 6 to 13 carbon atoms. In General Formula (G1-1), $R^{21}$ to $R^{27}$ separately represent any one of a hydrogen atom, an alkyl group having 1 to 4 carbon atoms, and a substituted or unsubstituted aryl group having 6 to 13 carbon atoms. In General Formula (G1-1), Z represents either a sulfur atom or an oxygen atom.

One embodiment of the present invention is an oxadiazole derivative represented by General Formula (G2-1) below.

(G2-1)

In General Formula (G2-1), $R^{21}$ to $R^{27}$ separately represent any one of a hydrogen atom, an alkyl group having 1 to 4 carbon atoms, and a substituted or unsubstituted aryl group having 6 to 13 carbon atoms. In General Formula (G2-1), Z represents either a sulfur atom or an oxygen atom.

One embodiment of the present invention is an oxadiazole derivative in which $R^1$ in General Formulae (G1) and (G1-1) separately represent any one of structures represented by Structural Formulae (2-1) to (2-22) below.

(2-1)

(2-2)

(2-3)

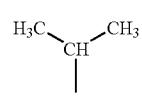 (2-4)
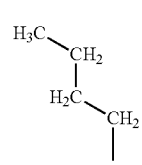 (2-5)
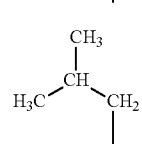 (2-6)
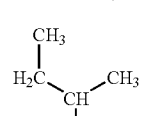 (2-7)
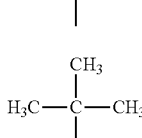 (2-8)
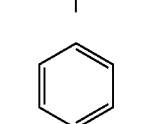 (2-9)
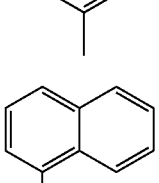 (2-10)
 (2-11)
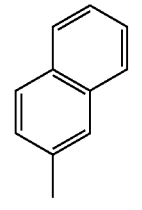 (2-11)
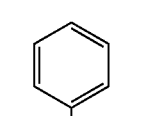 (2-12)
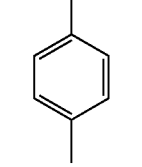 (2-13)
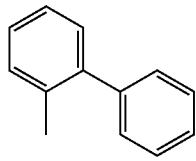 (2-14)
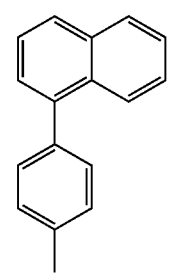 (2-15)
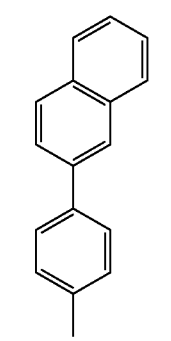 (2-16)
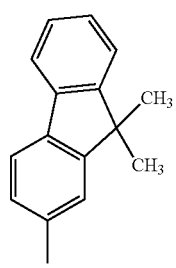 (2-17)
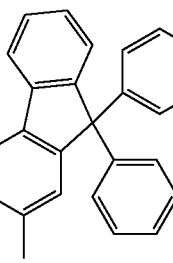 (2-18)
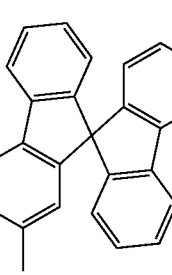 (2-19)

(2-20) 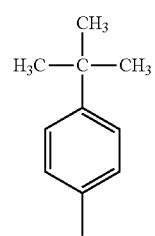
(2-21) 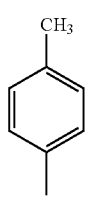
(2-22) 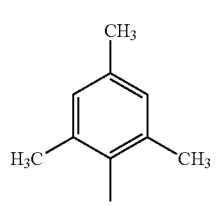
One embodiment of the present invention is an oxadiazole derivative in which $R^{21}$ to $R^{27}$ in General formulae (G1), (G2), (G1-1), and (G2-1) separately represent any one of structures represented by Structural Formulae (3-1) to (3-23) below.
(3-1) to (3-7) 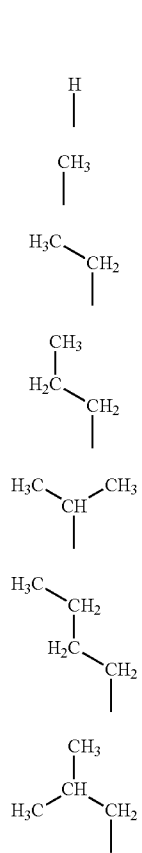
(3-8) 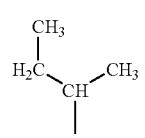
(3-9) 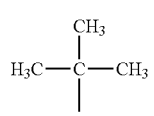
(3-10) 
(3-11) 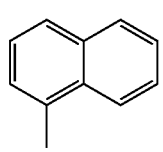
(3-12) 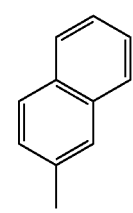
(3-13) 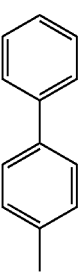
(3-14) 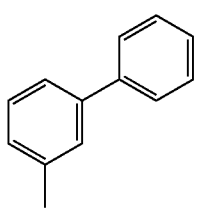
(3-15) 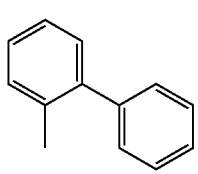

(3-16) 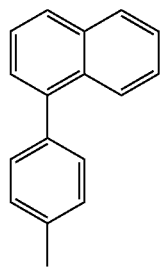

(3-17) 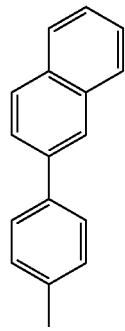

(3-18) 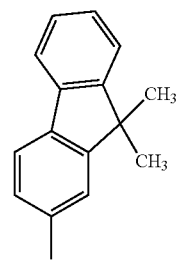

(3-19) 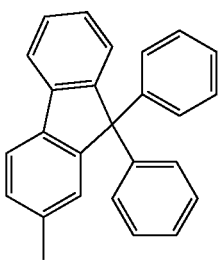

(3-20) 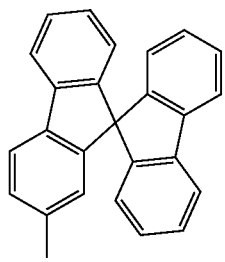

(3-21) 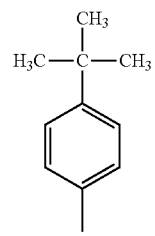

(3-22) 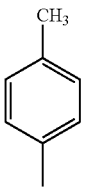

(3-23) 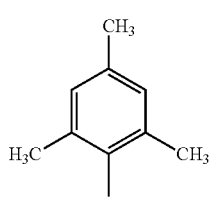

One embodiment of the present invention is a light-emitting element including an EL layer between a pair of electrodes, in which the EL layer includes any of the above oxadiazole derivatives.

Note that since the oxadiazole derivatives which are embodiments of the present invention are suitable for use as a host material of a light-emitting layer in an EL layer because of their high excitation energy. Accordingly, one embodiment of the present invention is a light-emitting element including an EL layer between a pair of electrodes. A light-emitting layer in the EL layer includes any of the above oxadiazole derivatives which are embodiments of the present invention and a light-emitting substance.

The oxadiazole derivatives which are embodiments of the present invention have a high electron-transport property; therefore, the oxadiazole derivative is optimal for use as an electron-transport material for an electron-transport layer in an EL layer of a light-emitting element.

One embodiment of the present invention is a light-emitting device manufactured using the light-emitting element which is one embodiment of the present invention.

One embodiment of the present invention is an electronic device manufactured using the light-emitting device which is one embodiment of the present invention.

One embodiment of the present invention is a lighting device manufactured using the light-emitting device which is one embodiment of the present invention.

Note that a light emitting device in this specification refers to an image display device, a light emitting device, or a light source. Further, the light-emitting device includes, in its category, all of a module in which a connector such as a flexible printed circuit (FPC), a tape automated bonding (TAB) tape, or a tape carrier package (TCP) is attached to a light-emitting device; a module having a TAB tape or a TCP provided with a printed wiring board at the end thereof; and a module having an integrated circuit (IC) directly mounted over a light-emitting element by a chip on glass (COG) method.

According to one embodiment of the present invention, an oxadiazole derivative having high excitation energy, in particular, an oxadiazole derivative having high triplet excitation energy can be provided. According to one embodiment of the present invention, a light-emitting element having high current efficiency, which is formed using the oxadiazole derivative of one embodiment of the present invention, can be provided. According to one embodiment of the present invention, a light-emitting device, an electronic device, and a lighting device each having low power consumption and low driving voltage, to which the light-emitting elements are applied, can be provided.

DETAILED DESCRIPTION OF THE INVENTION

Figure 1A:
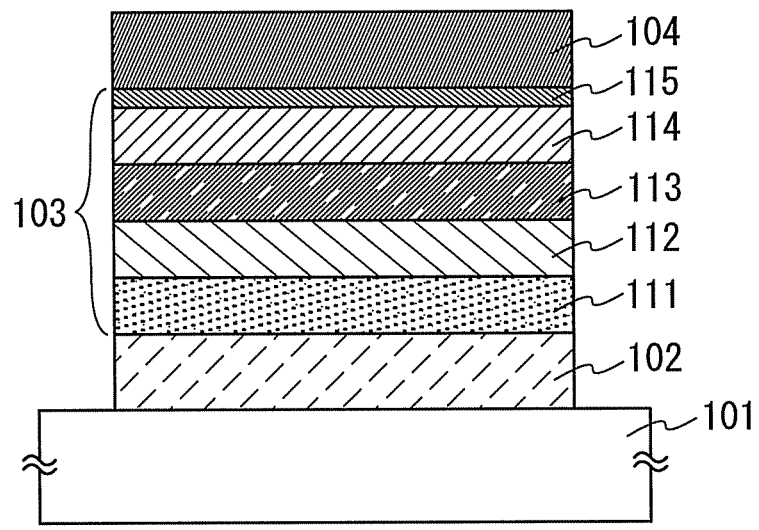
FIGS. 1A and 1B each illustrate a light-emitting element of one embodiment of the present invention.

Hereinafter, embodiments of the present invention are described with reference to the accompanying drawings. Note that the present invention is not limited to the description given below, and it will be easily understood by those skilled in the art that various changes and modifications can be made without departing from the spirit and scope of the present invention. Therefore, the present invention should not be construed as being limited to the description in the following embodiments.

Embodiment 1

In Embodiment 1, oxadiazole derivatives which are embodiments of the present invention will be described.

An oxadiazole derivative according to one embodiment of the present invention is represented by General Formula (G1).

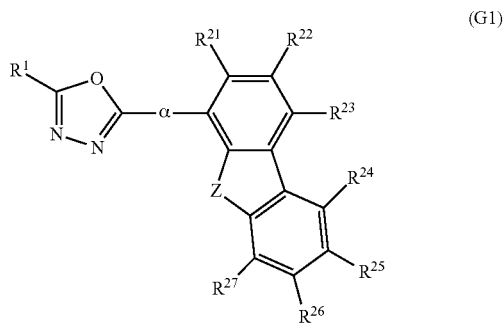

(G1)

In General Formula (G1), $R^1$ represents either an alkyl group having 1 to 4 carbon atoms or a substituted or unsubstituted aryl group having 6 to 13 carbon atoms. In General Formula (G1), $R^{21}$ to $R^{27}$ separately represent any one of a hydrogen atom, an alkyl group having 1 to 4 carbon atoms, and a substituted or unsubstituted aryl group having 6 to 13 carbon atoms. In General Formula (G1), α represents a substituted or unsubstituted arylene group having 6 to 13 carbon atoms. In General Formula (G1), Z represents either a sulfur atom or an oxygen atom.

An oxadiazole derivative according to one embodiment of the present invention is represented by General Formula (G2) below.

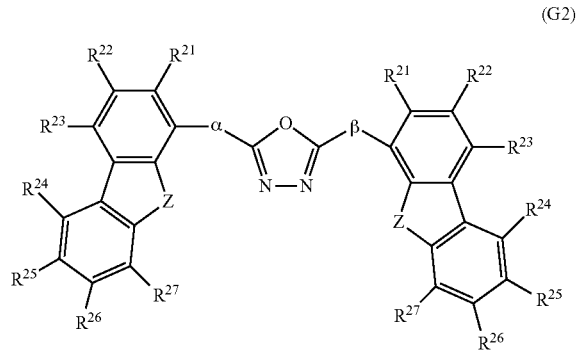

(G2)

In General Formula (G2), $R^{21}$ to $R^{27}$ separately represent any one of a hydrogen atom, an alkyl group having 1 to 4 carbon atoms, and a substituted or unsubstituted aryl group having 6 to 13 carbon atoms. In General Formula (G2), α and β separately represent a substituted or unsubstituted arylene group having 6 to 13 carbon atoms. In General Formula (G2), Z represents either a sulfur atom or an oxygen atom.

In an oxadiazole derivative according to one embodiment of the present invention, α and β in General Formulae (G1) and (G2) separately represent either a substituted or unsubstituted phenylene group or a substituted or unsubstituted biphenyldiyl group.

In an oxadiazole derivative according to one embodiment of the present invention, α and β in General Formulae (G1) and (G2) separately represent a substituted or unsubstituted phenylene group.

In General Formulae (G1) and (G2), as specific examples of structures represented by α and β, structures represented by Structural Formulae (1-1) to (1-15) shown below can be given.

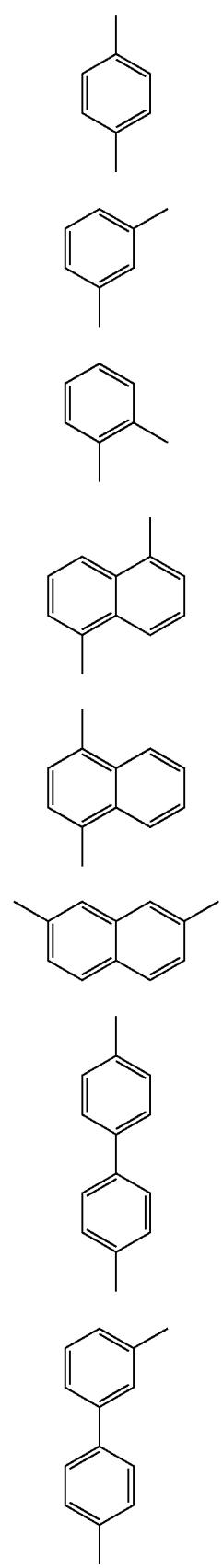
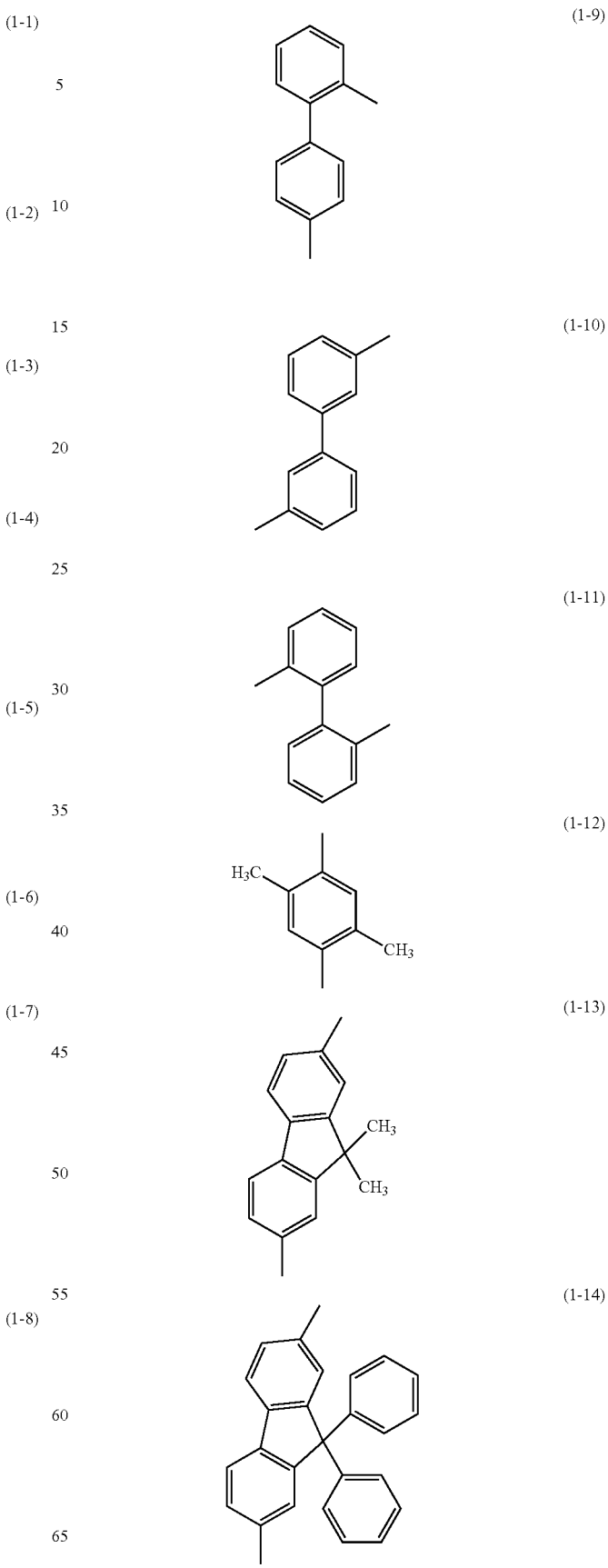

(1-15)

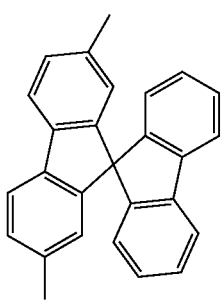

One embodiment of the present invention is an oxadiazole derivative represented by General Formula (G1-1) below.

(G1-1)

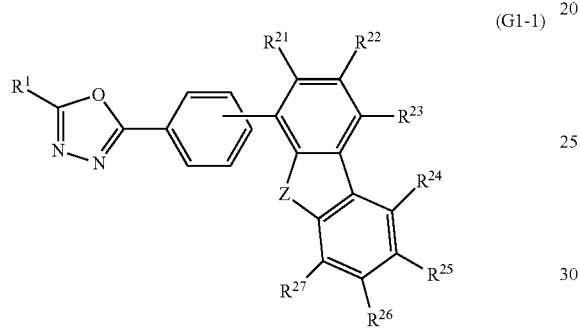

In General Formula (G1-1), $R^1$ represents either an alkyl group having 1 to 4 carbon atoms or a substituted or unsubstituted aryl group having 6 to 13 carbon atoms. In General Formula (G1-1), $R^{21}$ to $R^{27}$ separately represent any one of a hydrogen atom, an alkyl group having 1 to 4 carbon atoms, and a substituted or unsubstituted aryl group having 6 to 13 carbon atoms. In General Formula (G1-1), Z represents either a sulfur atom or an oxygen atom.

One embodiment of the present invention is an oxadiazole derivative represented by General Formula (G2-1) below.

(G2-1)

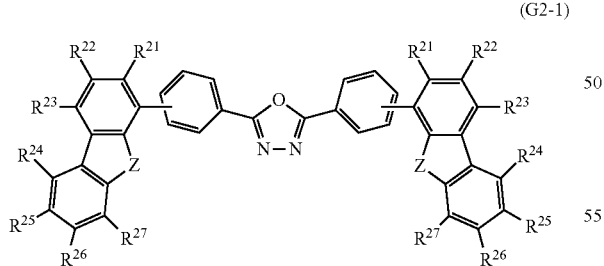

In General Formula (G2-1), $R^{21}$ to $R^{27}$ separately represent any one of a hydrogen atom, an alkyl group having 1 to 4 carbon atoms, and a substituted or unsubstituted aryl group having 6 to 13 carbon atoms. In General Formula (G2-1), Z represents either a sulfur atom or an oxygen atom.

As specific examples of a substituent represented by $R^1$ in General Formulae (G1) and (G1-1), substituents represented by Structural Formulae (2-1) to (2-22) below can be given.

(2-1)

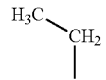
(2-2)

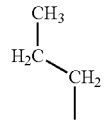
(2-3)

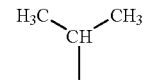
(2-4)

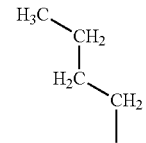
(2-5)

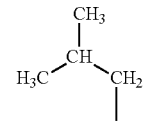
(2-6)

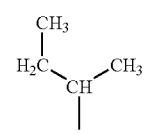
(2-7)

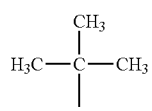
(2-8)

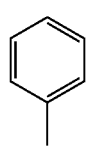
(2-9)

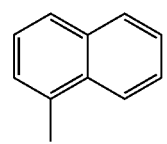
(2-10)

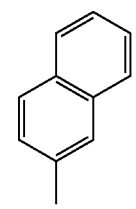
(2-11)

(2-12)
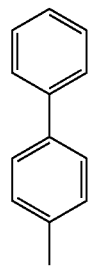
(2-13)
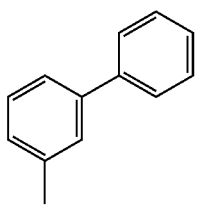
(2-14)
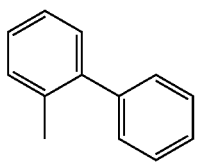
(2-15)
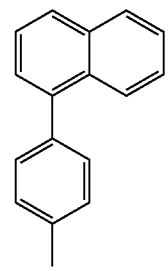
(2-16)
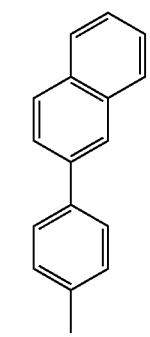
(2-17)
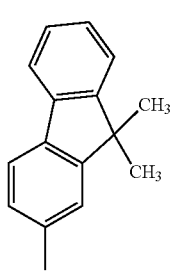
(2-18)
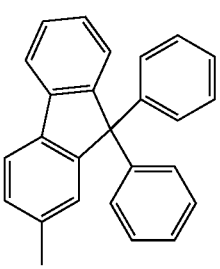
(2-19)
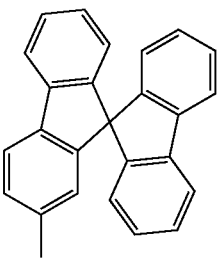
(2-20)
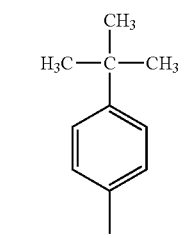
(2-21)
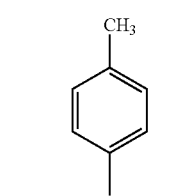
(2-22)
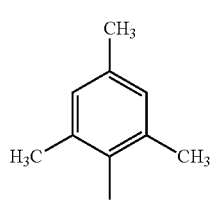
As specific examples of substituents represented by $R^{21}$ to $R^{27}$ in General Formulae (G1), (G2), (G1-1), and (G2-1), substituents represented by Structural Formulae (3-1) to (3-23) below can be given.
(3-1)
(3-2)
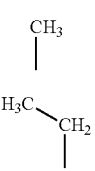
(3-3)

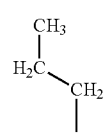 (3-4)
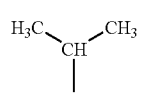 (3-5)
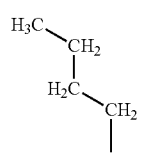 (3-6)
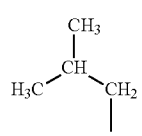 (3-7)
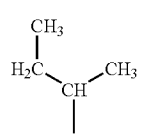 (3-8)
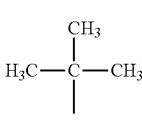 (3-9)
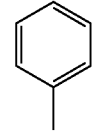 (3-10)
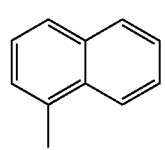 (3-11)
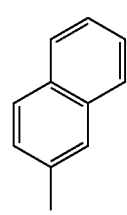 (3-12)
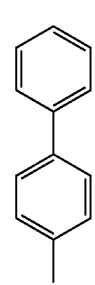 (3-13)
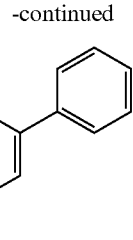 (3-14)
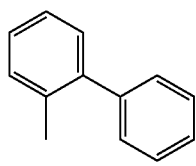 (3-15)
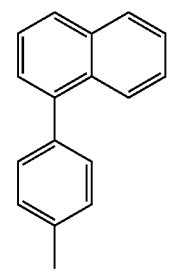 (3-16)
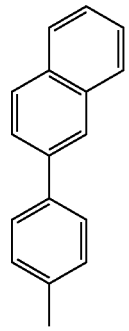 (3-17)
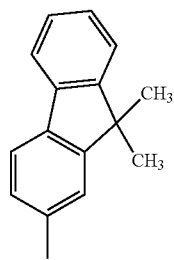 (3-18)

(3-19)
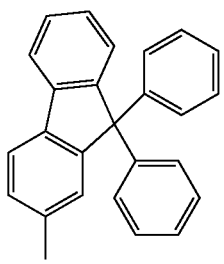
(3-20)
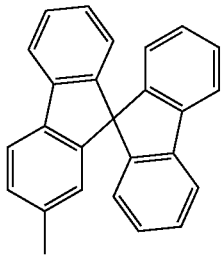
(3-21)
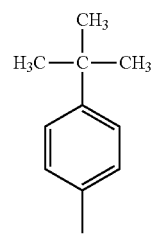
(3-22)
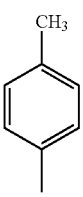
(3-23)
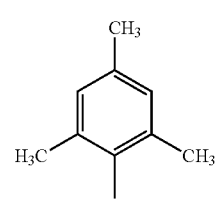
Specific examples of the oxadiazole derivative of one embodiment of the present invention, which is represented by General Formula (G1), include oxadiazole derivatives represented by Structural Formulae (100) to (167), (200) to (235), (300) to (367), and (400) to (435). However, the present invention is not limited to these.
(100)
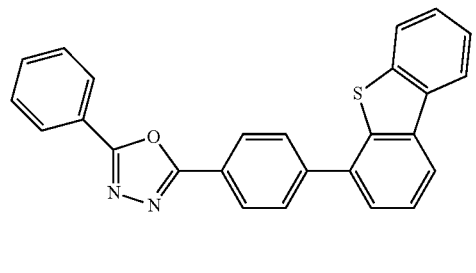
(101)
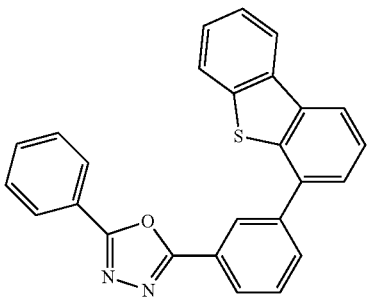
(102)
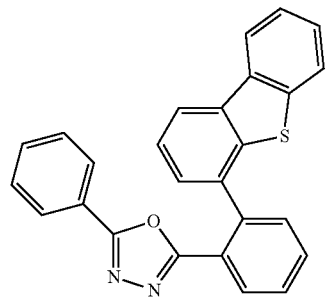
(103)
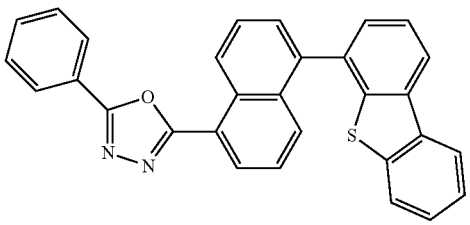

-continued
(104) 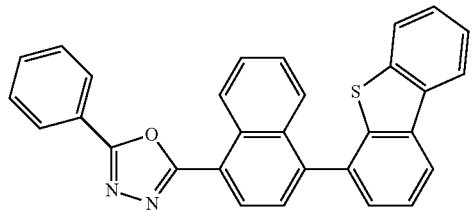
(105) 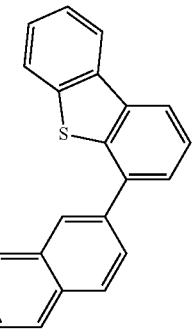
(106) 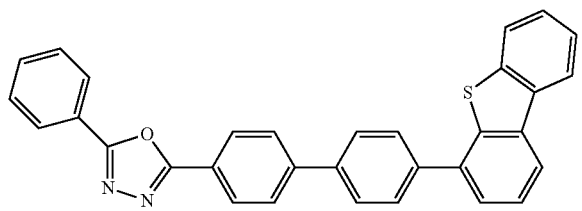
(107) 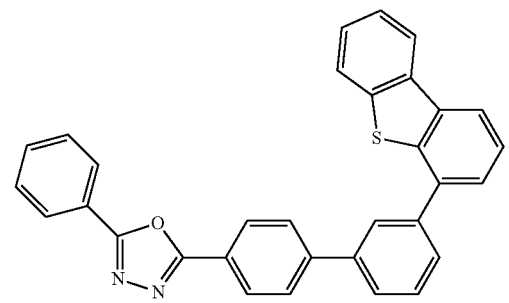
(108) 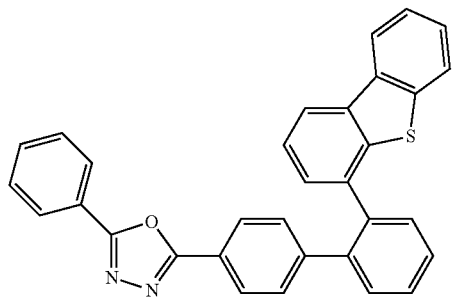
(109) 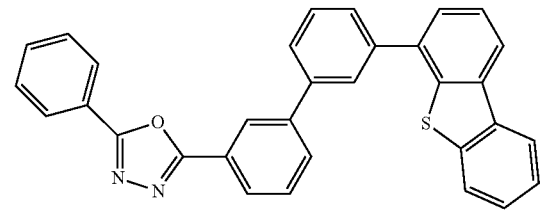
(110) 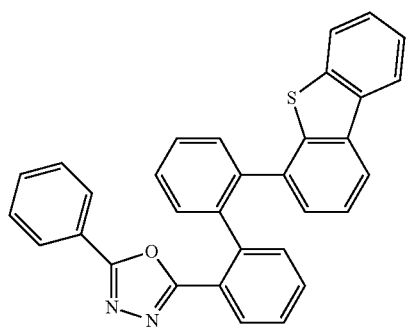
(111) 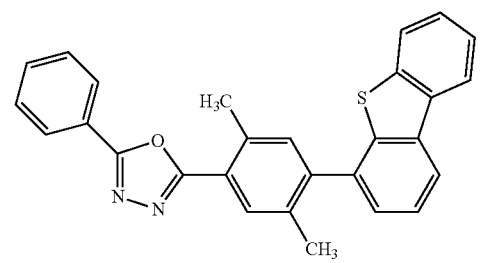
(112) 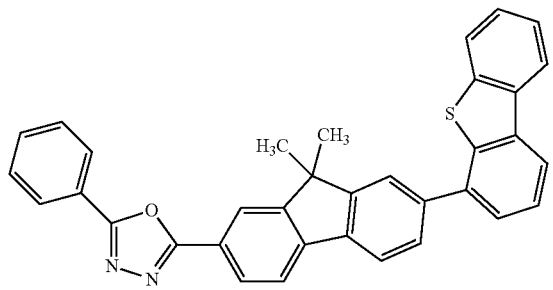
(113) 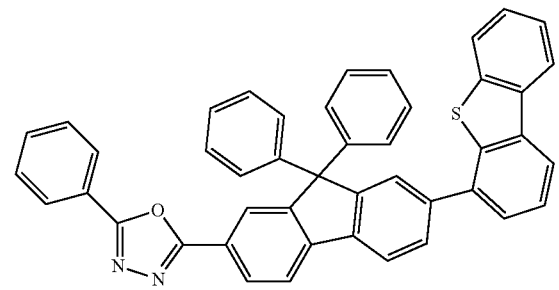

-continued
(114)
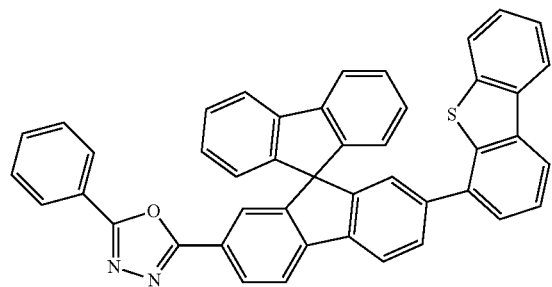
(115)
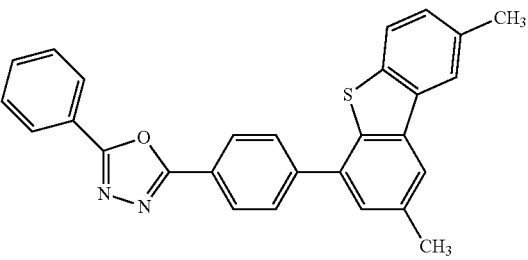
(116)
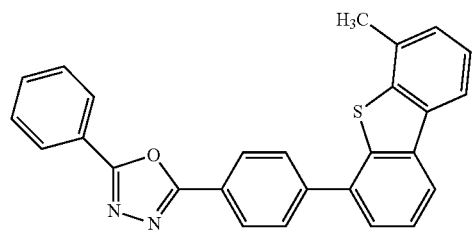
(117)
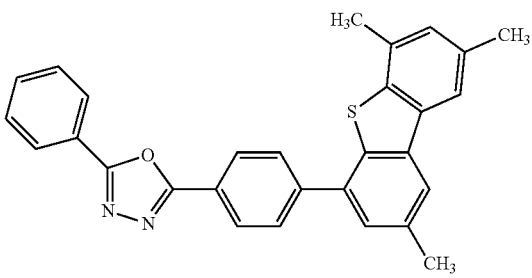
(118)
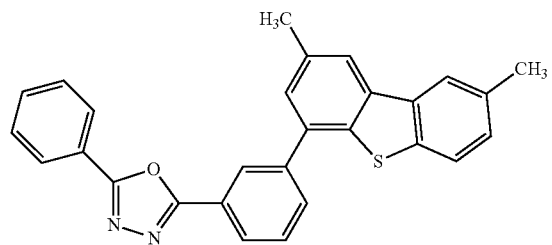
(119)
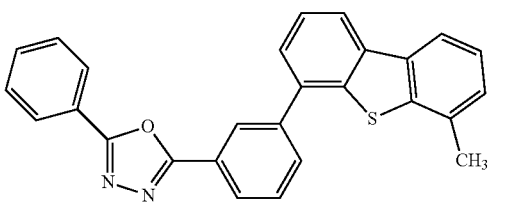
(120)
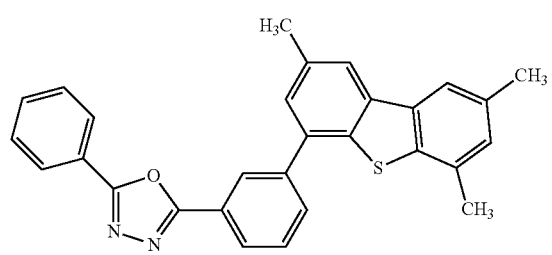
(121)
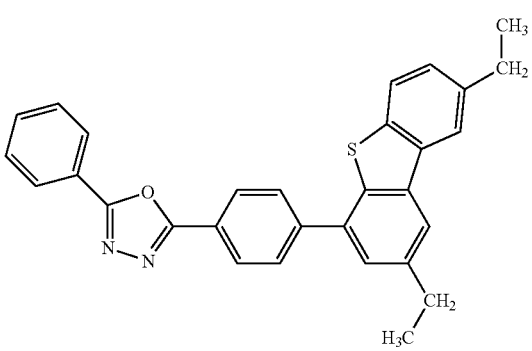
(122)
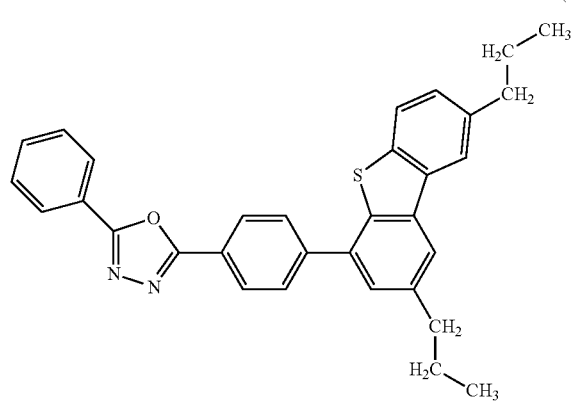
(123)
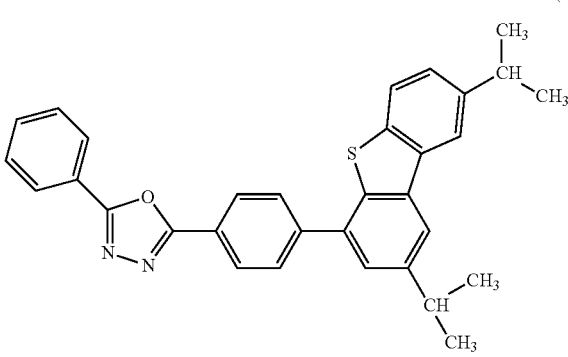

-continued
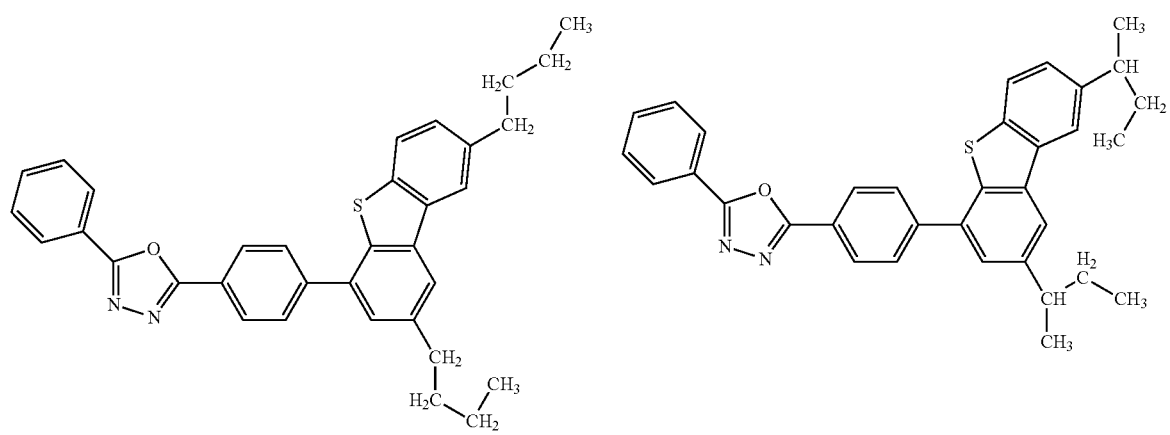
(124) (125)
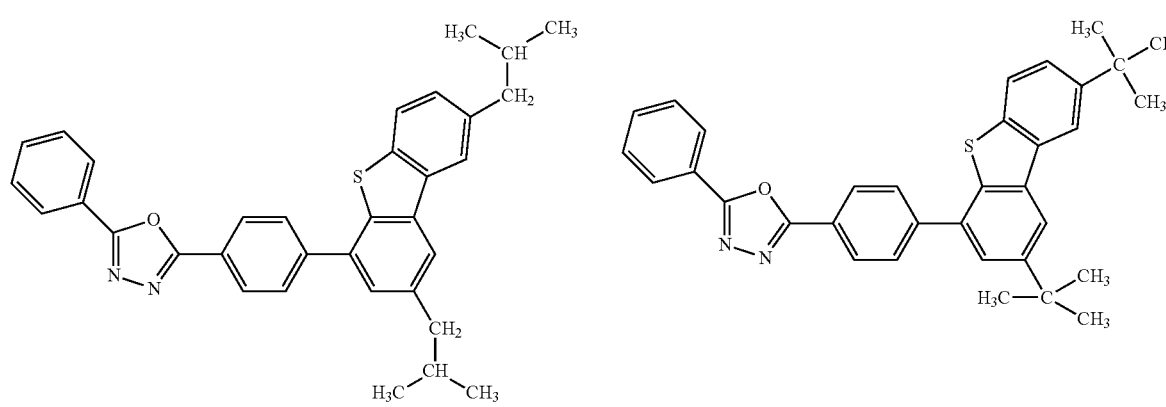
(126) (127)
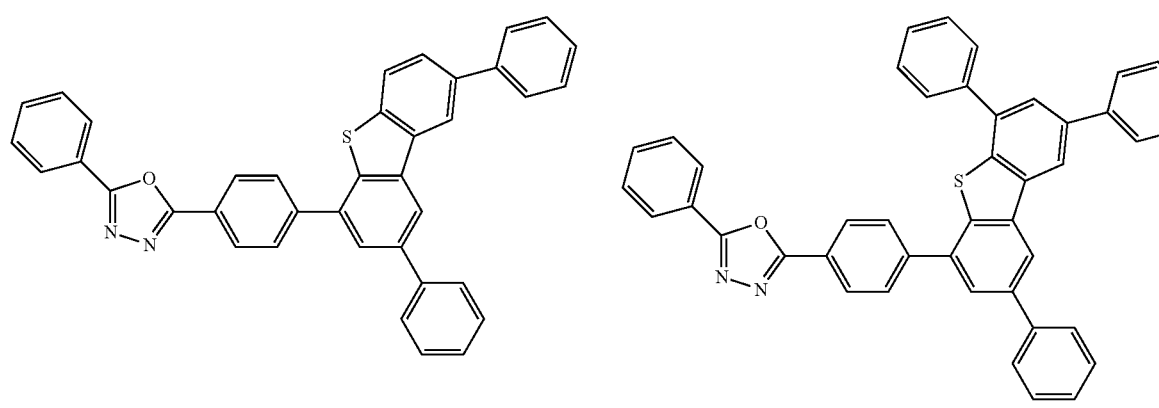
(128) (129)
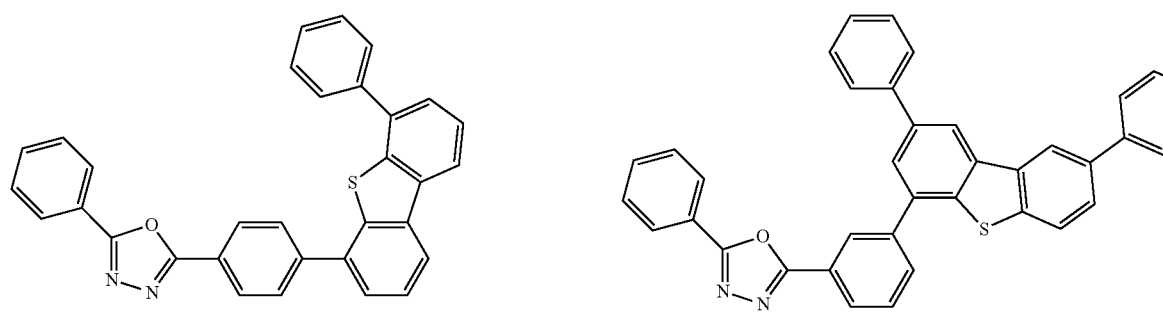
(130) (131)

-continued
(132)
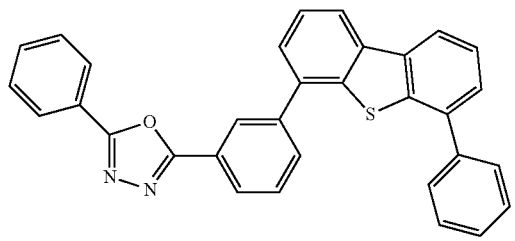
(133)
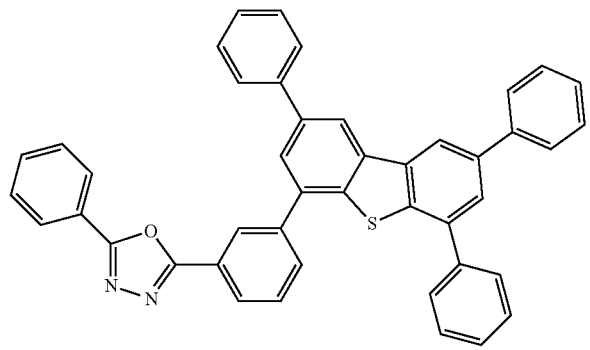
(134)
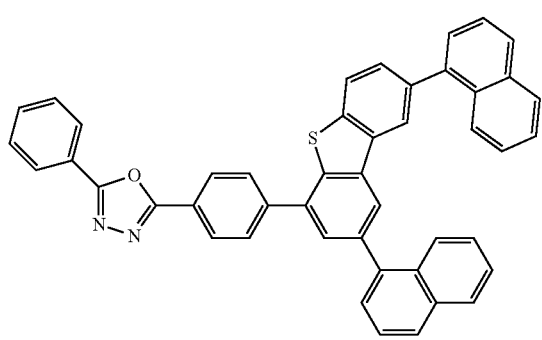
(135)
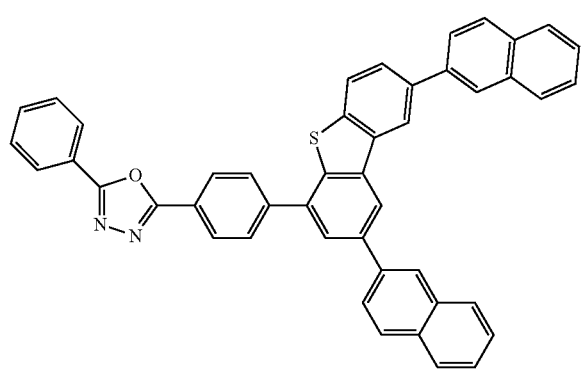
(136)
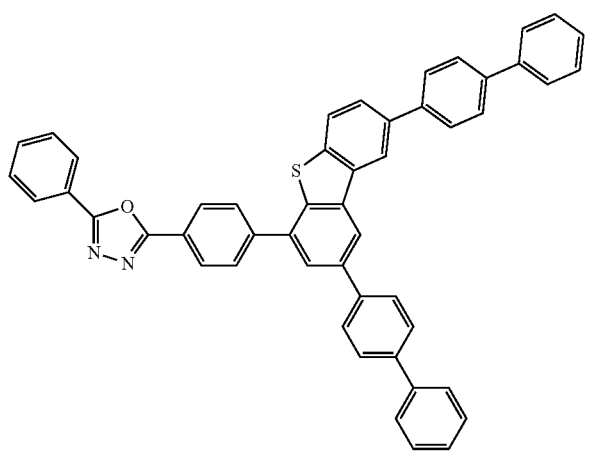
(137)
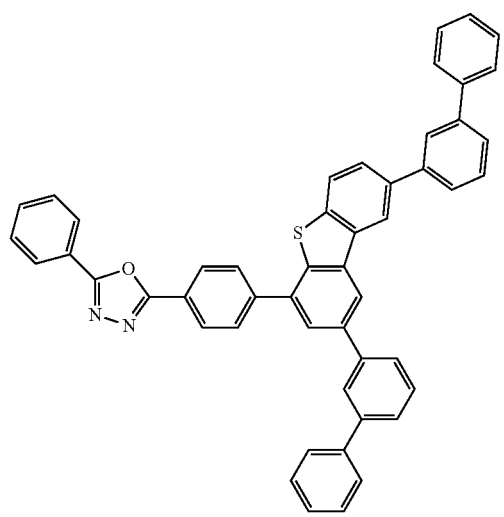

-continued
(138)
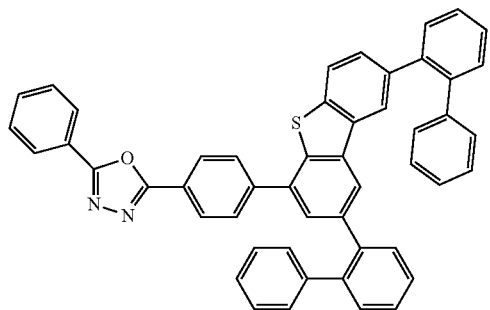
(139)
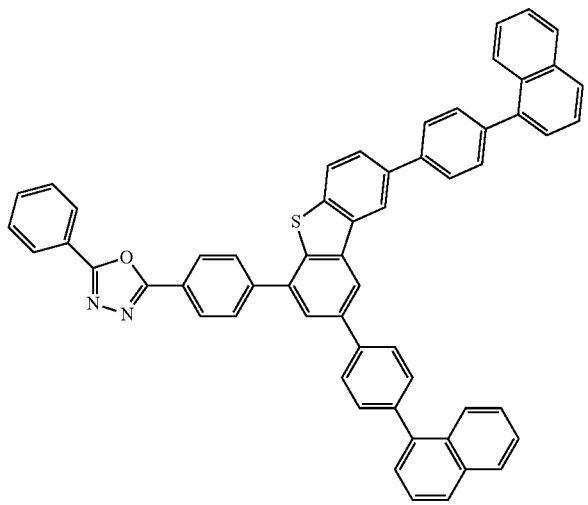
(140)
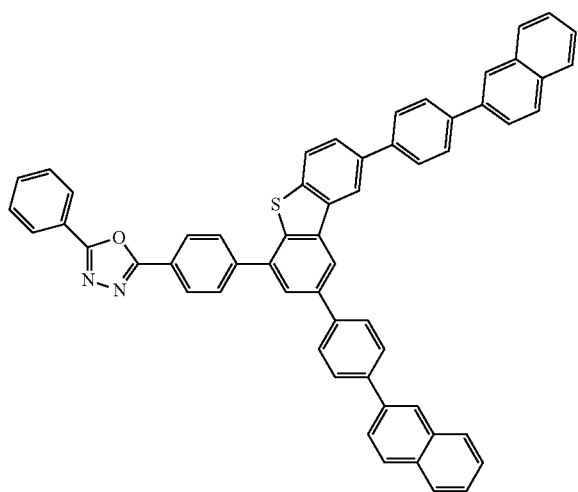
(141)
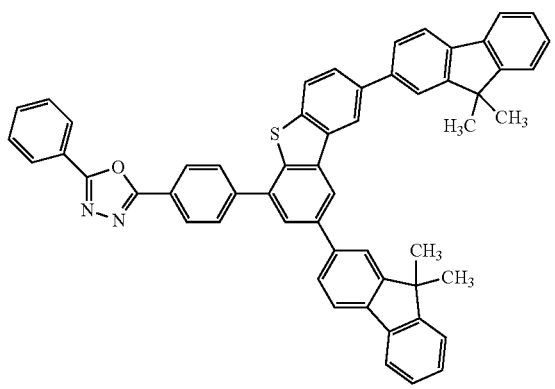
(142)
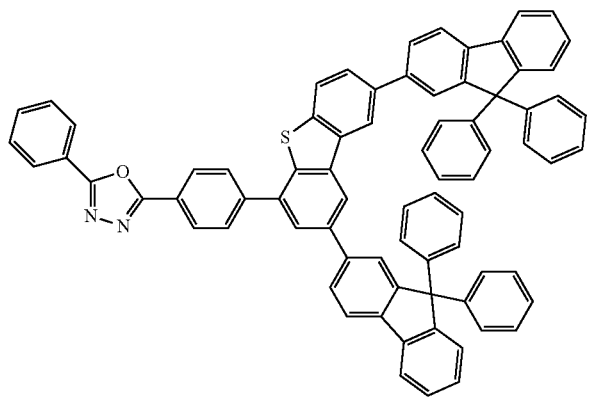
(143)
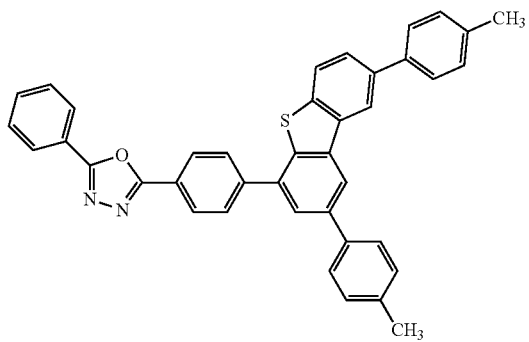

-continued
(144)
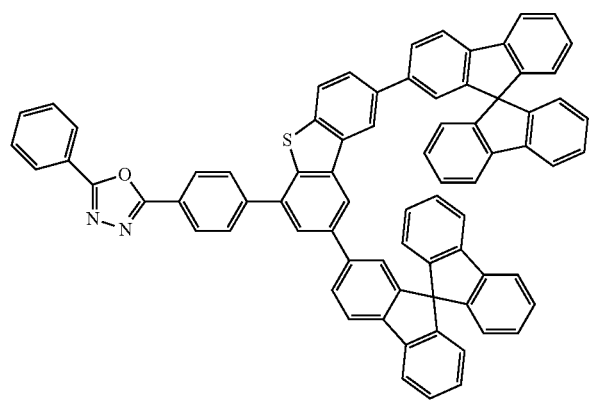
(145)
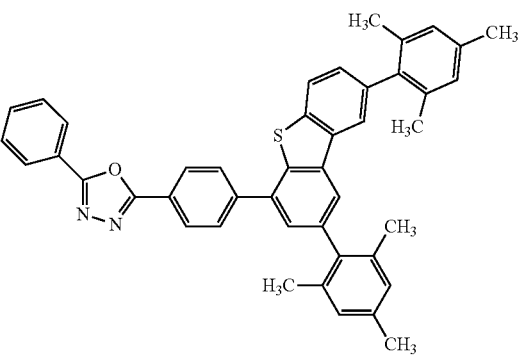
(146)
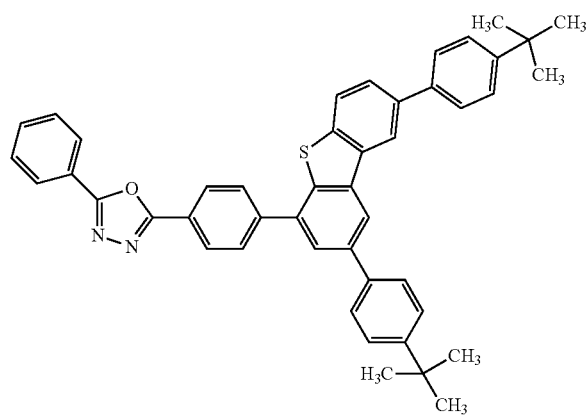
(147)
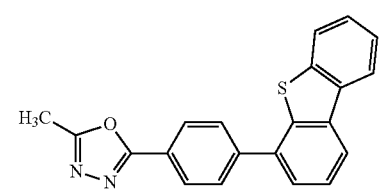
(148)
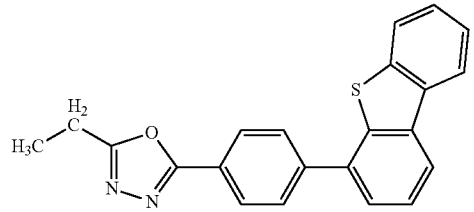
(149)
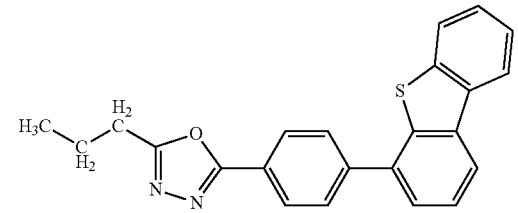
(150)
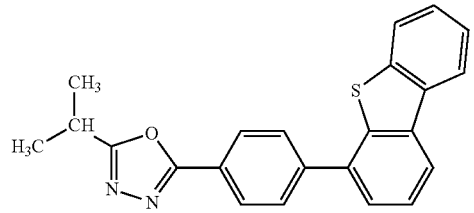
(151)
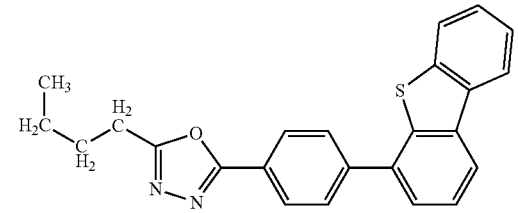
(152)
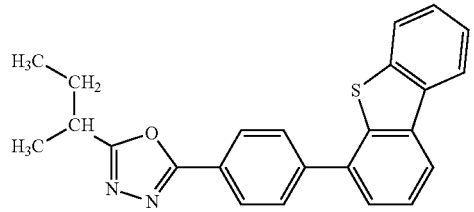
(153)
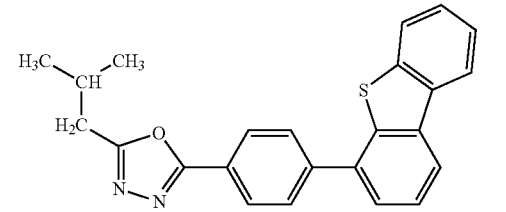

-continued
(154)
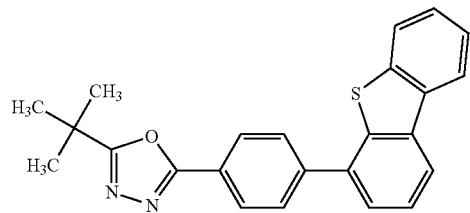
(155)
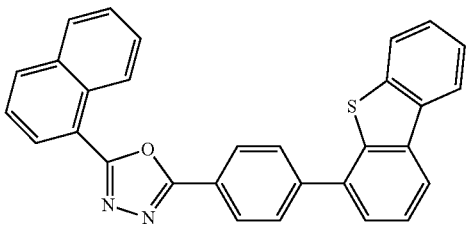
(156)
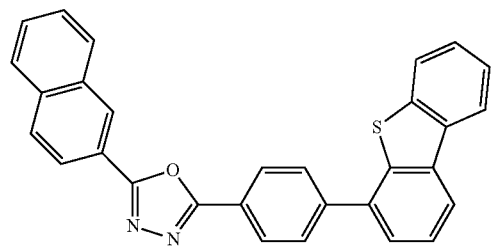
(157)
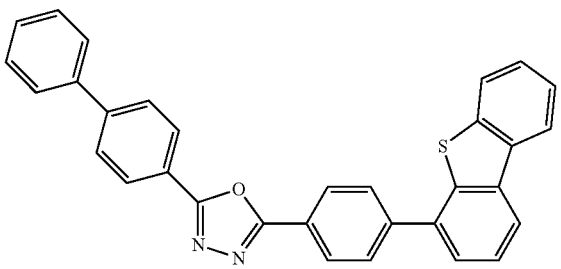
(158)
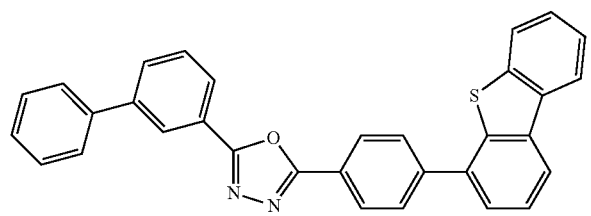
(159)
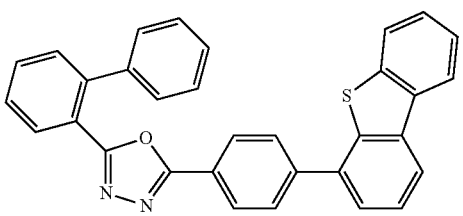
(160)
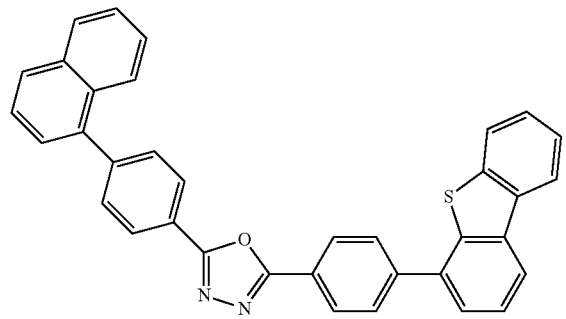
(161)
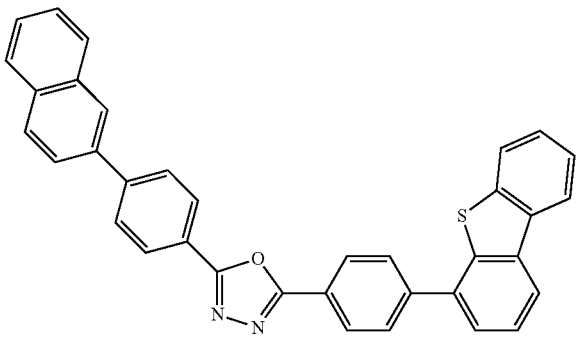
(162)
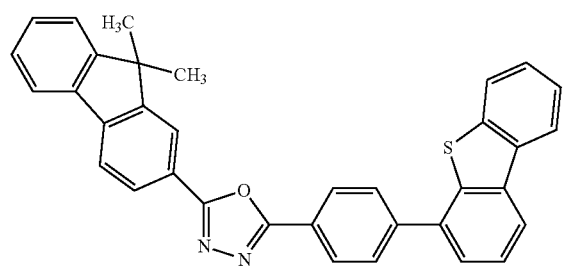
(163)
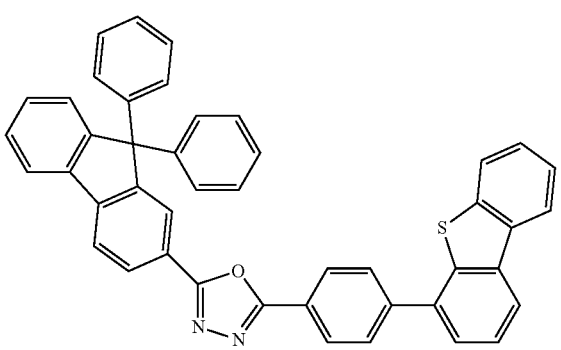

-continued
(164)
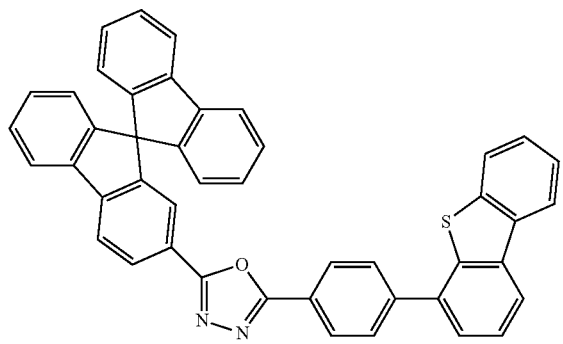
(165)
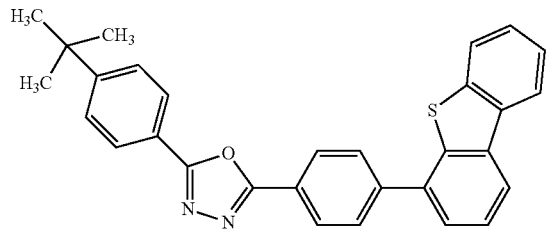
(166)
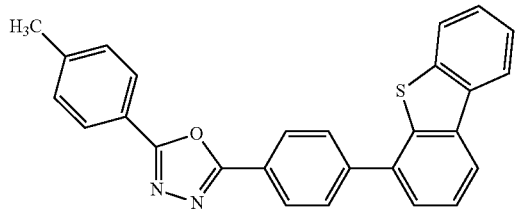
(167)
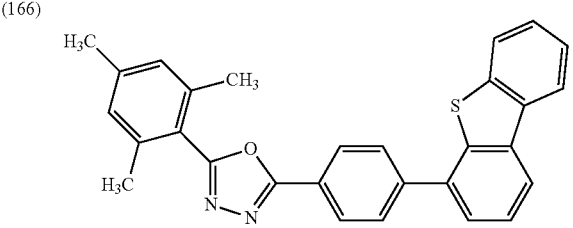
(200)
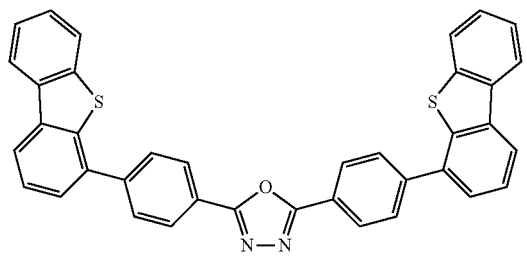
(201)
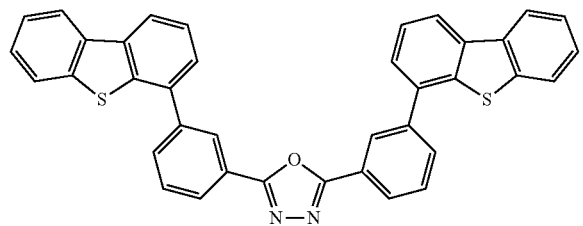
(202)
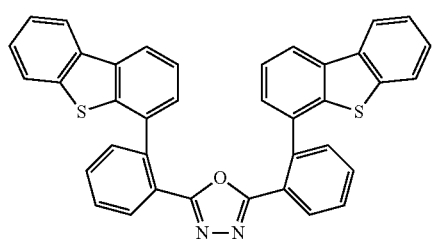
(203)
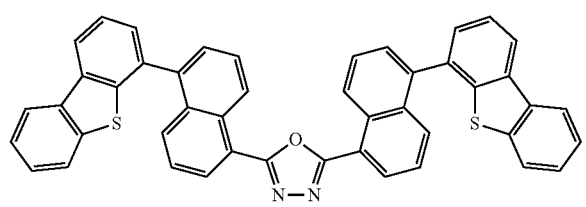
(204)
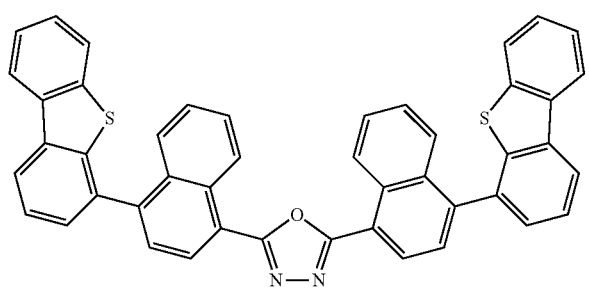
(205)
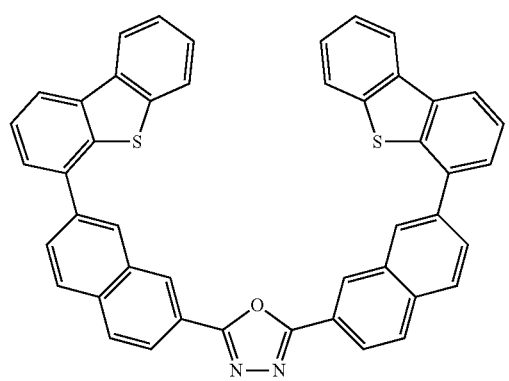

-continued
(206)
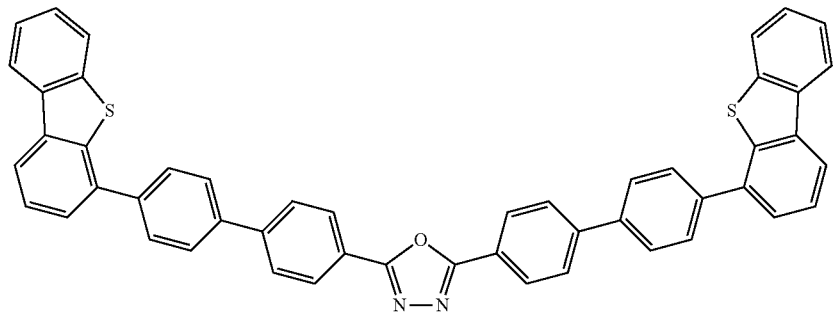
(207) (208)
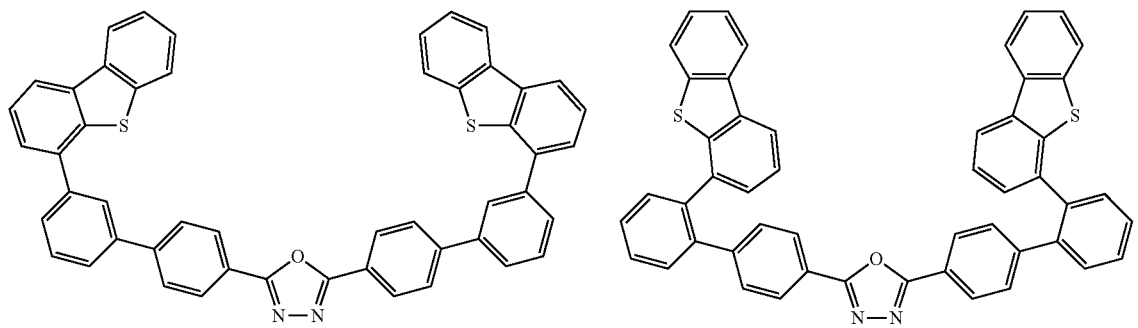
(209)
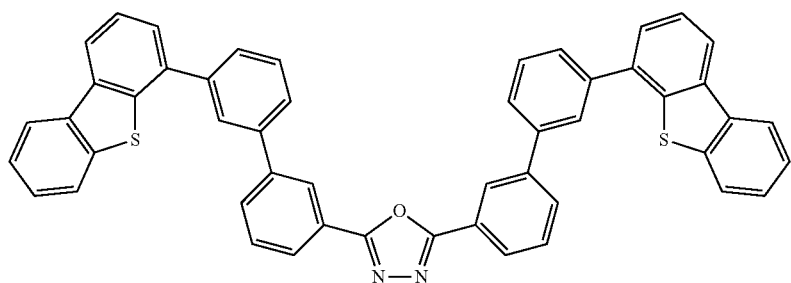
(210) (211)
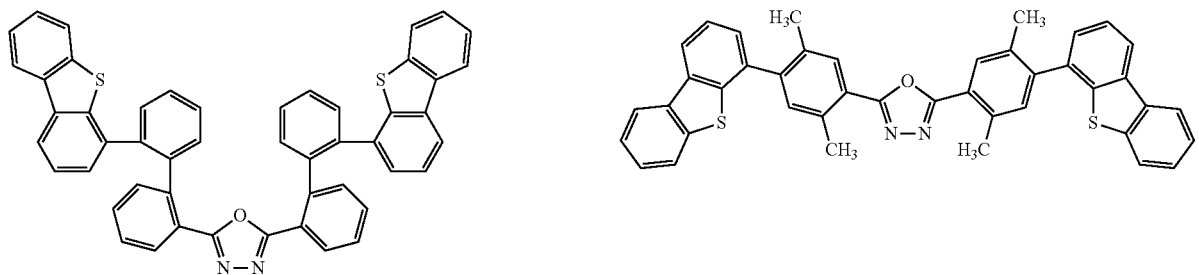
(212)
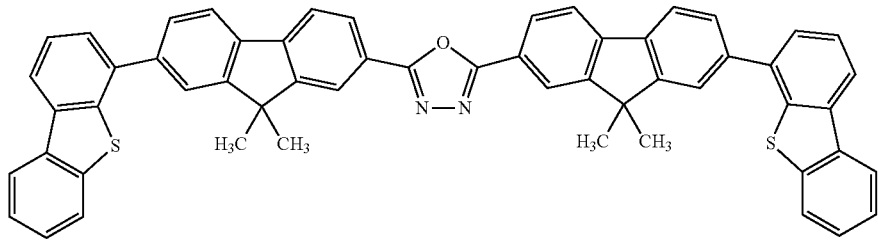

(213)
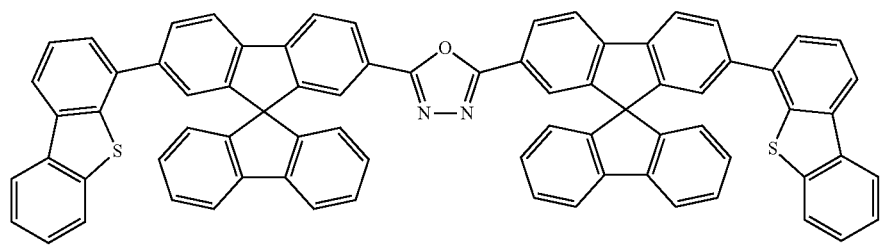
(214)
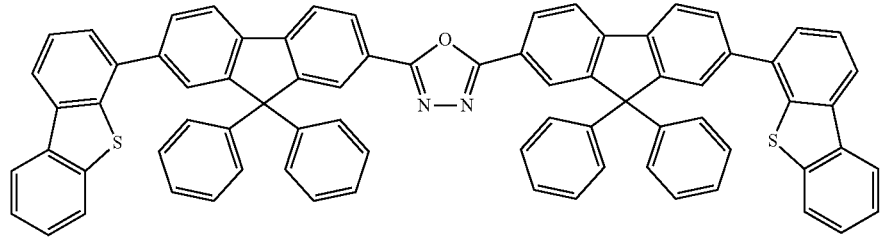
(215) (216)
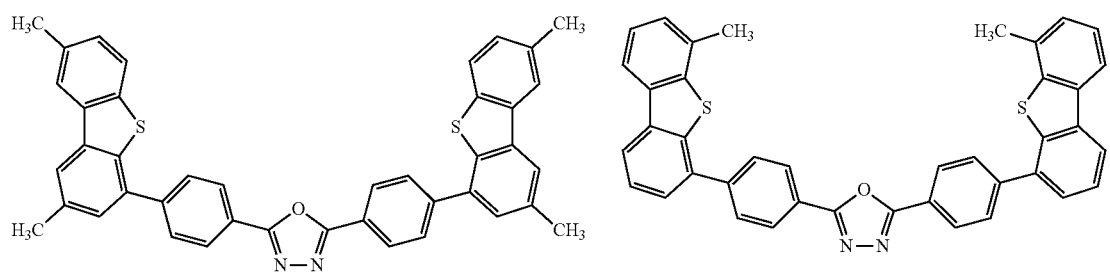
(217)
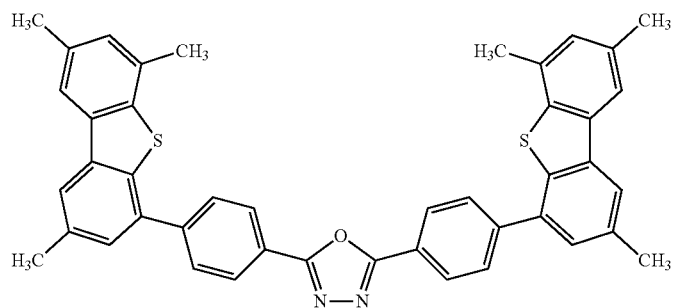
(218)
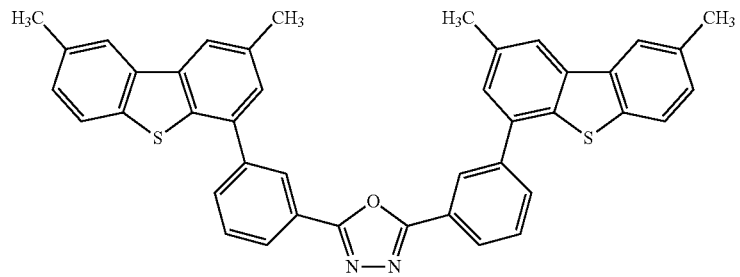
(219)
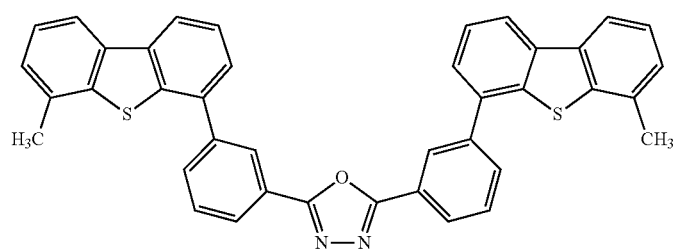

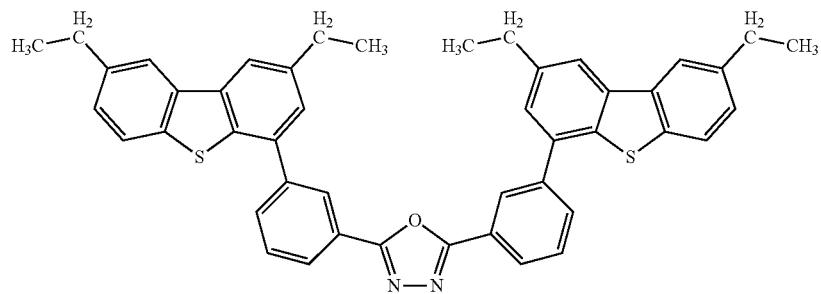
(220)
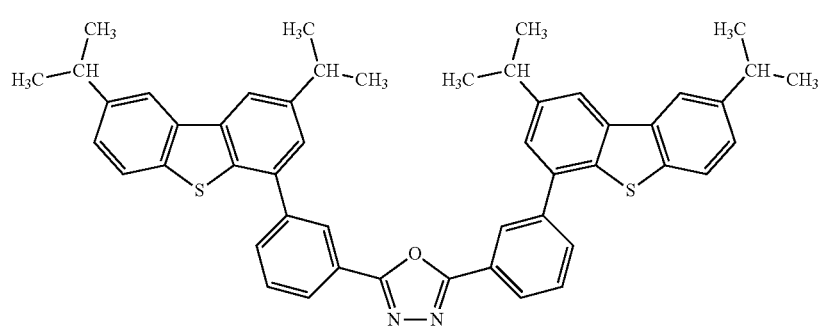
(221)
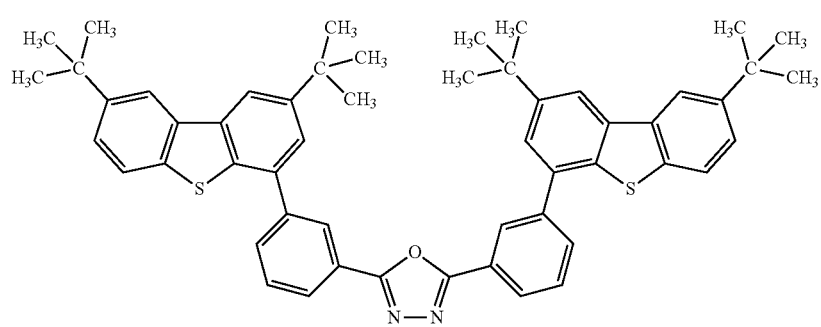
(222)
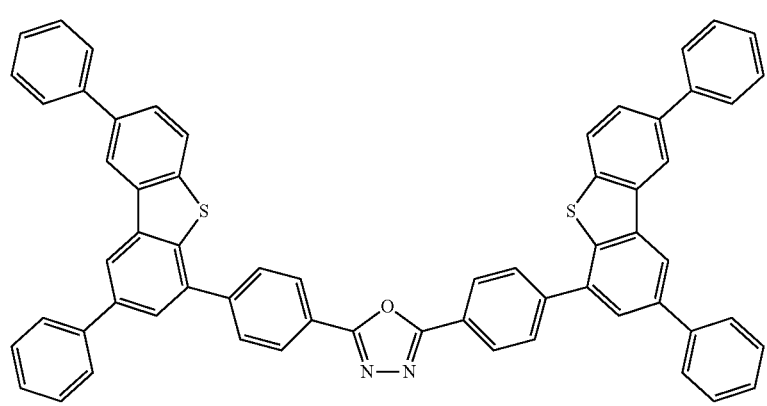
(223)

-continued
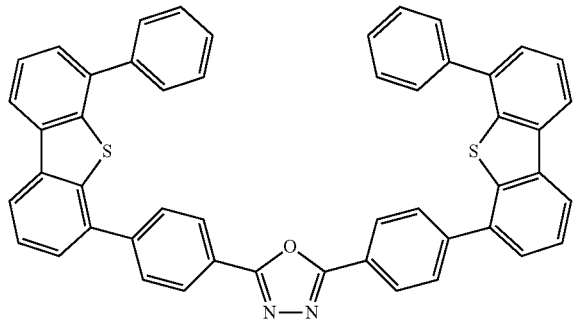
(224)
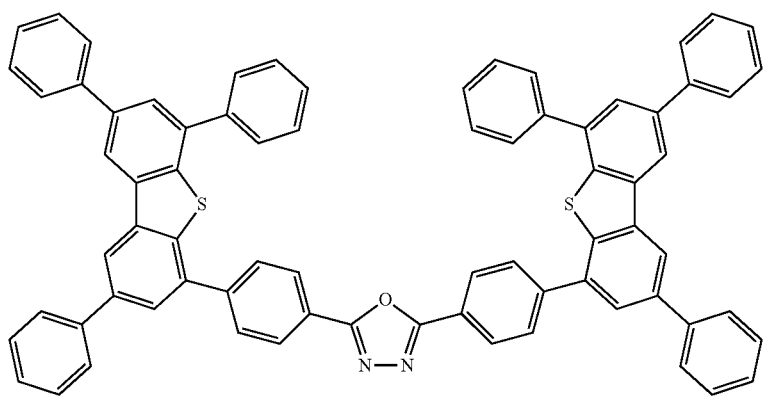
(225)
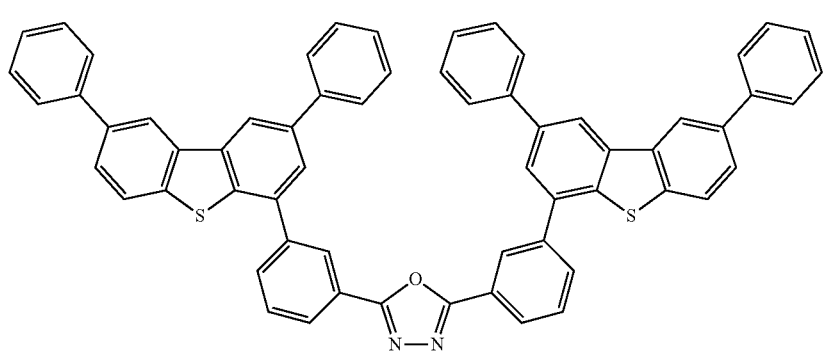
(226)
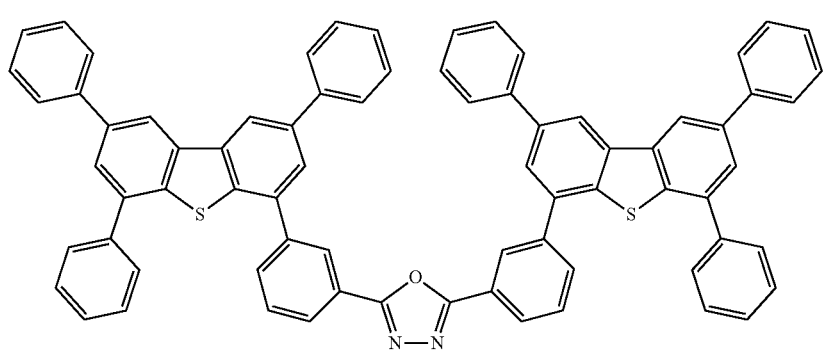
(227)

-continued
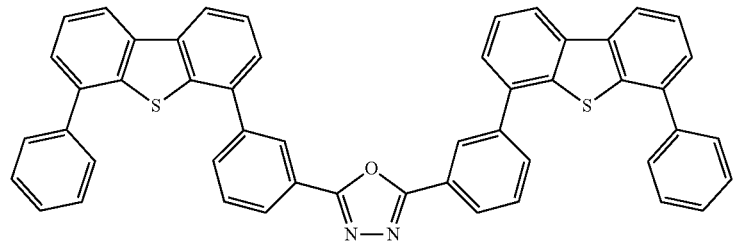
(228)
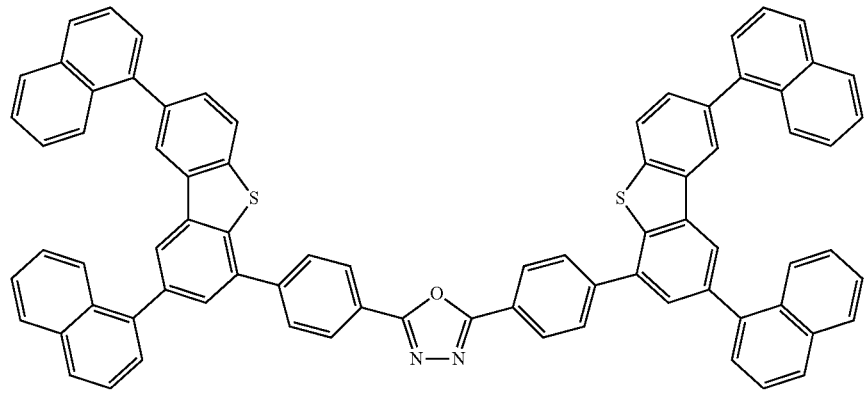
(229)
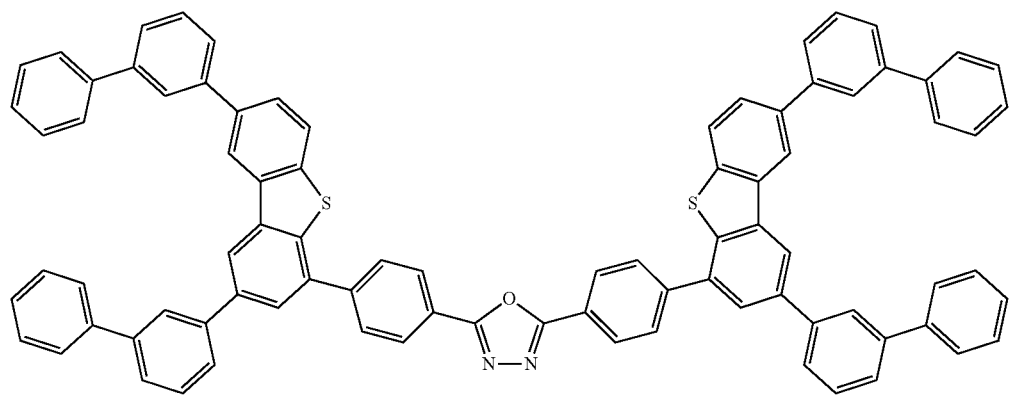
(230)
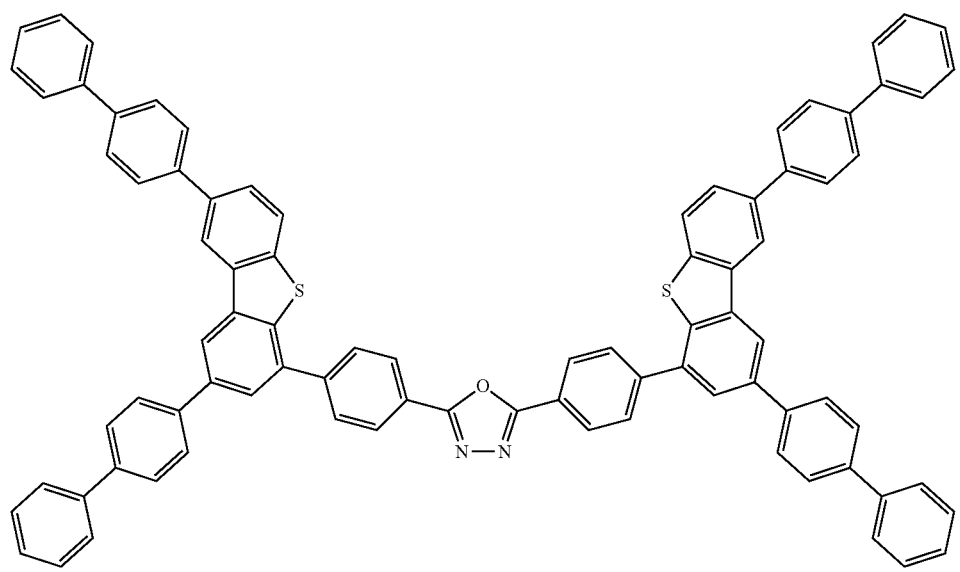
(231)

(232)
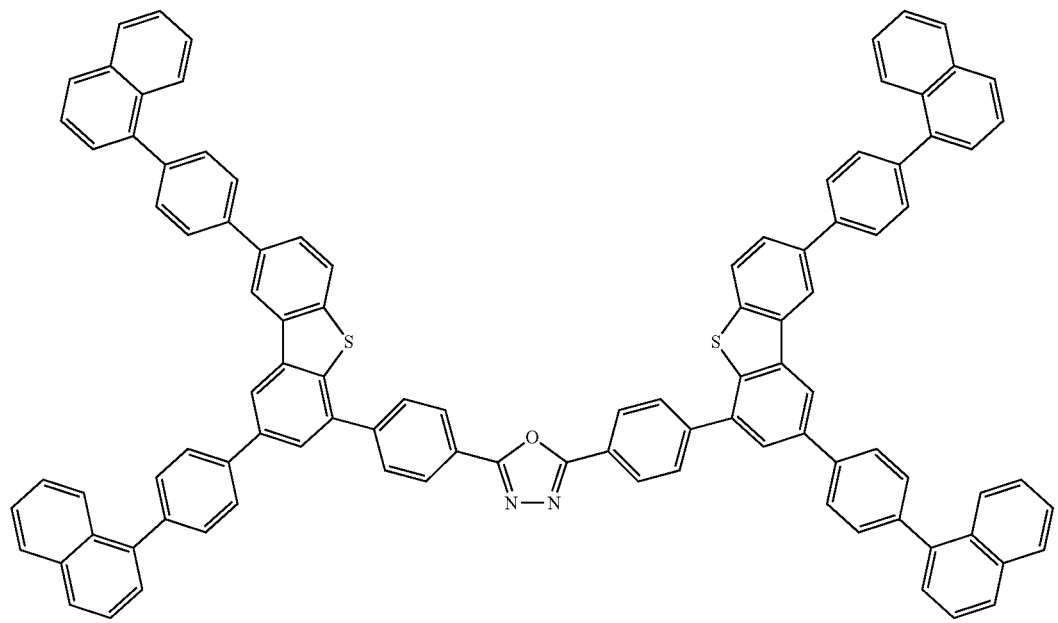
(233)
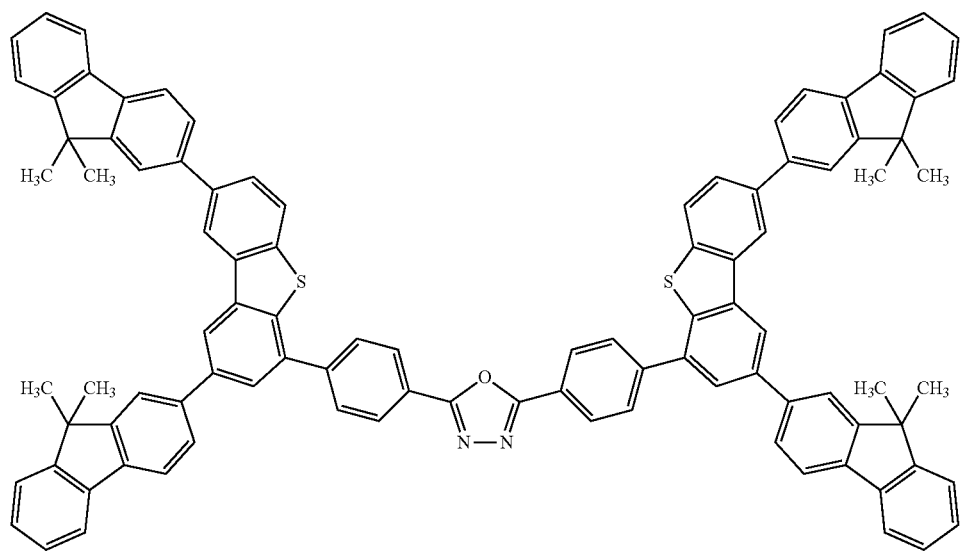

(234)
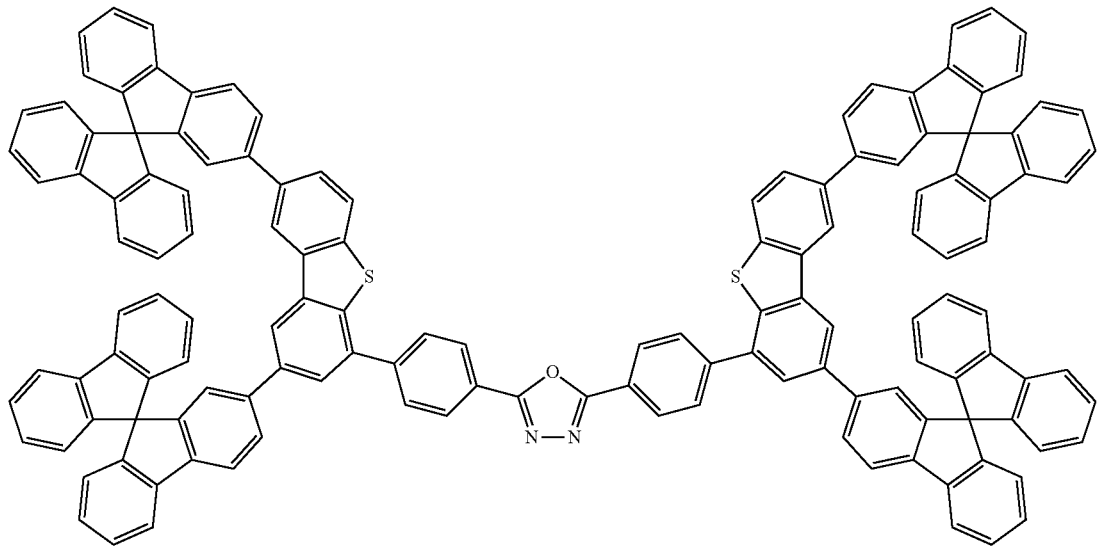
(235)
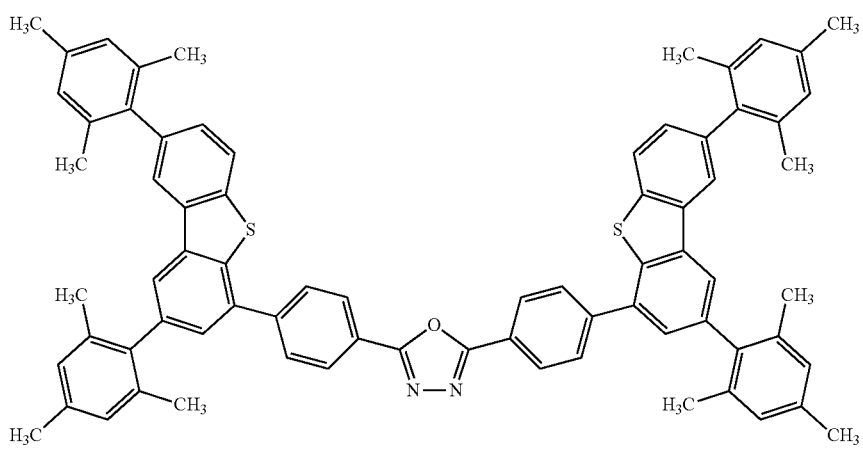
(300)
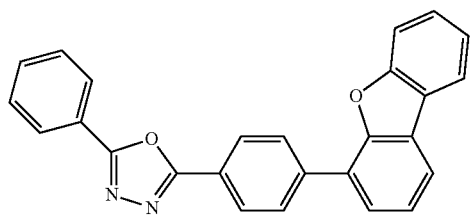
(301)
(302)
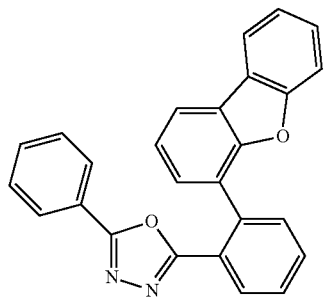
(303)
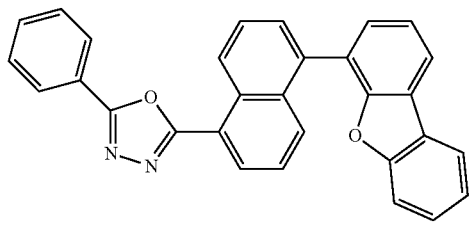

-continued
(304)
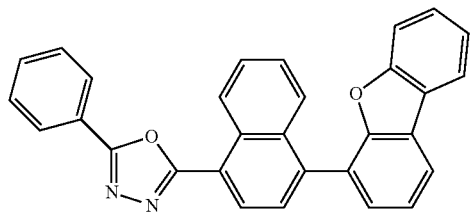
(305)
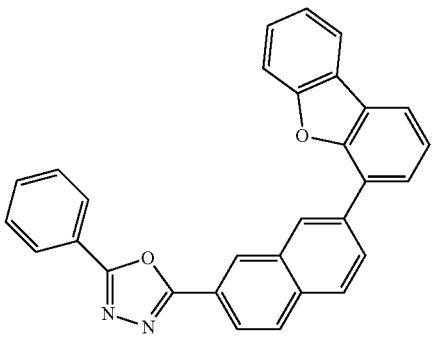
(306)
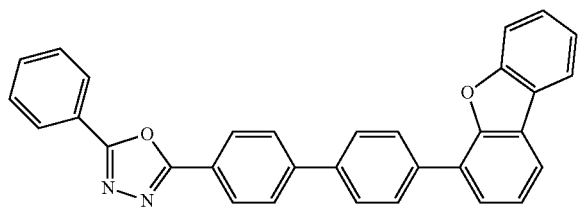
(307)
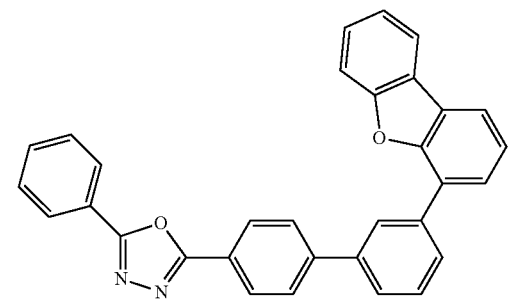
(308)
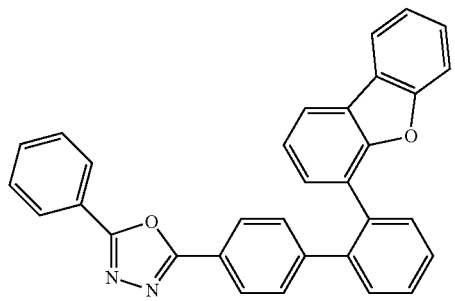
(309)
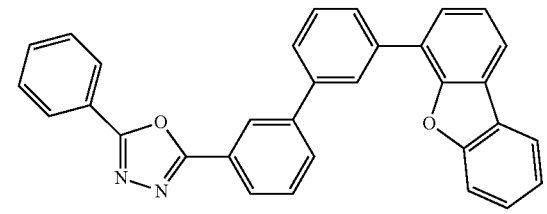
(310)
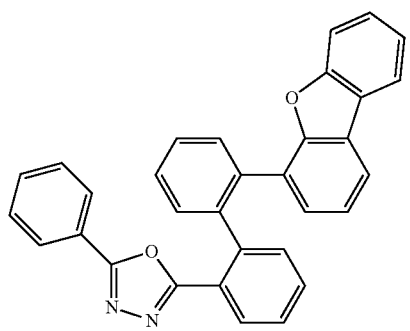
(311)
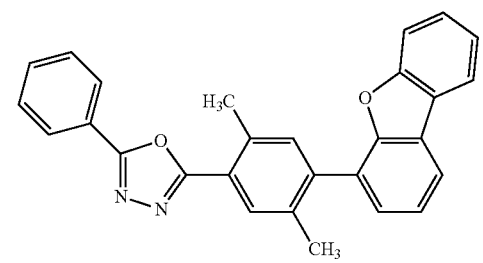
(312)
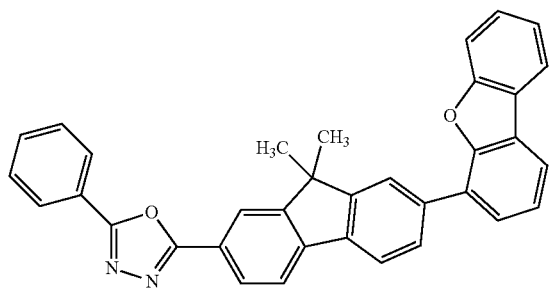
(313)
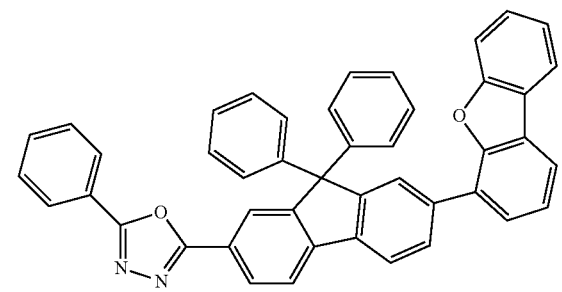

-continued
(314)
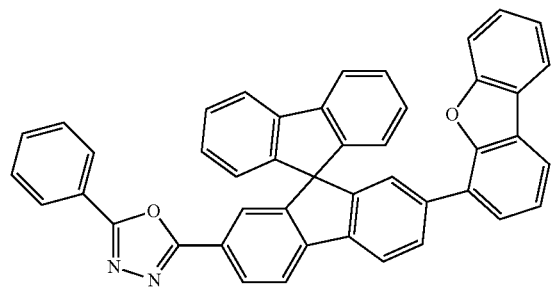
(315)
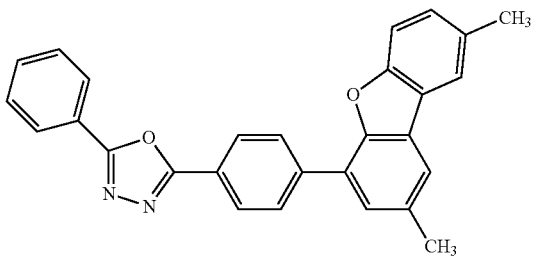
(316)
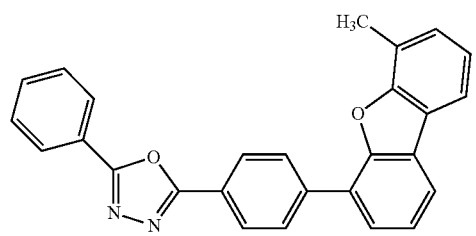
(317)
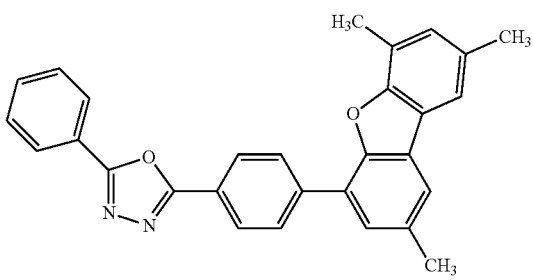
(318)
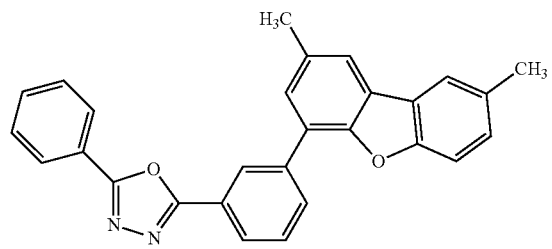
(319)
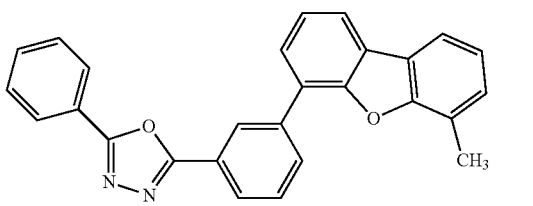
(320)
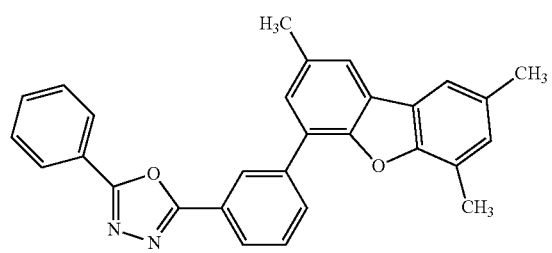
(321)
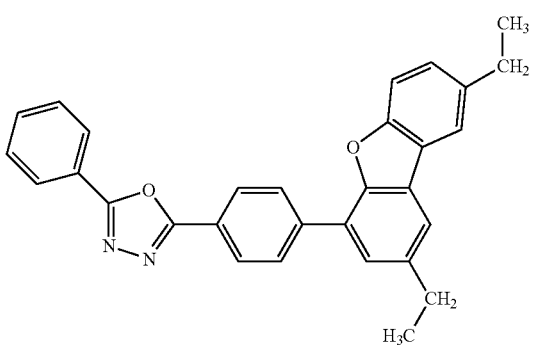
(322)
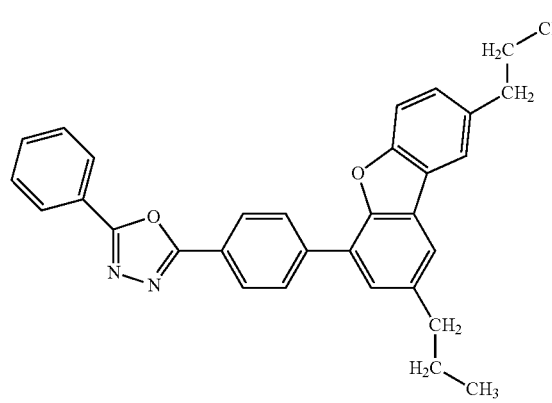
(323)
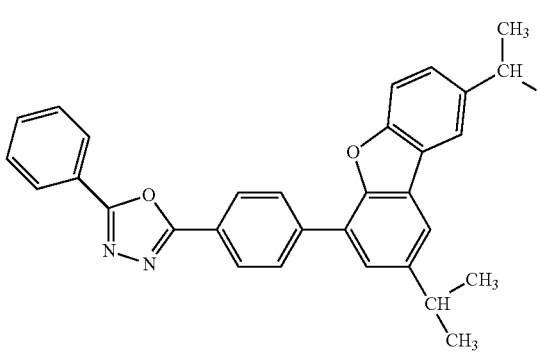

-continued
(324)
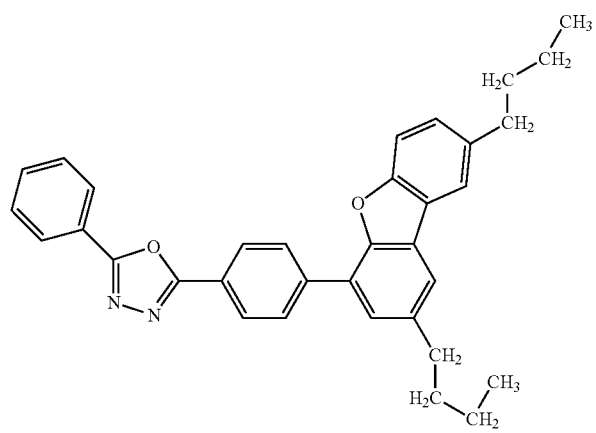
(325)
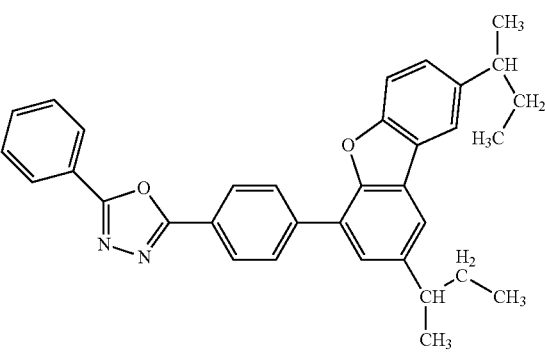
(326)
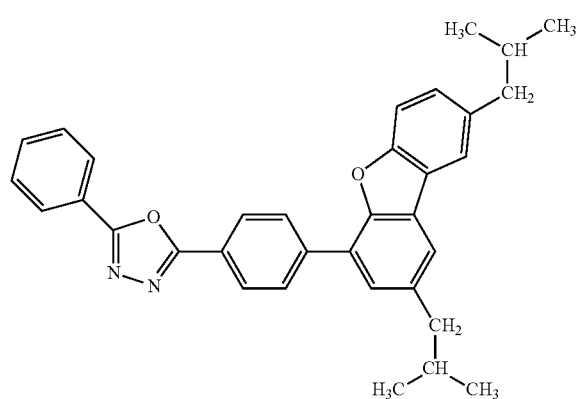
(327)
(328)
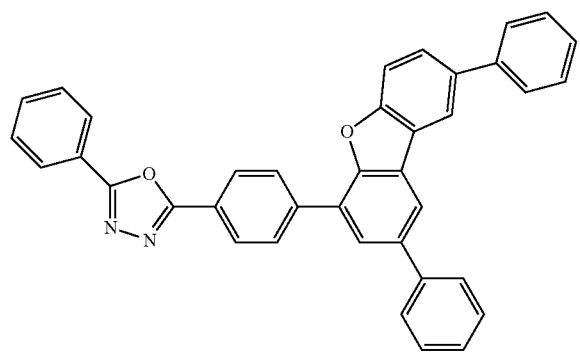
(329)
(330)
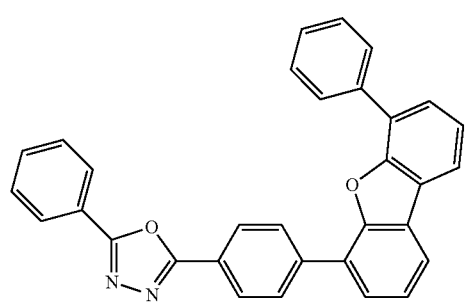
(331)
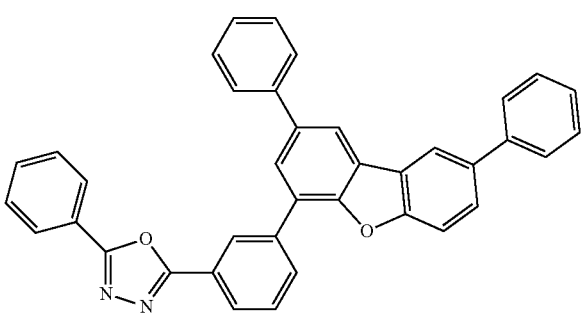

-continued
(332)
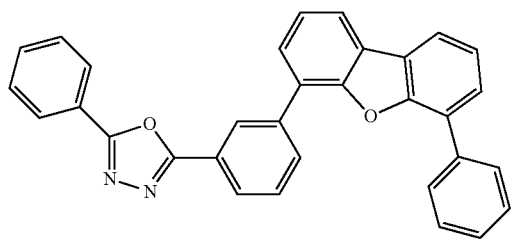
(333)
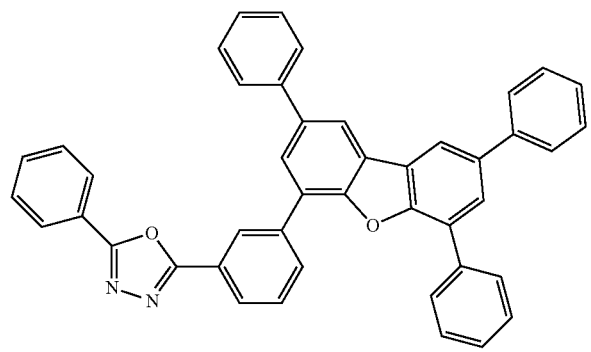
(334)
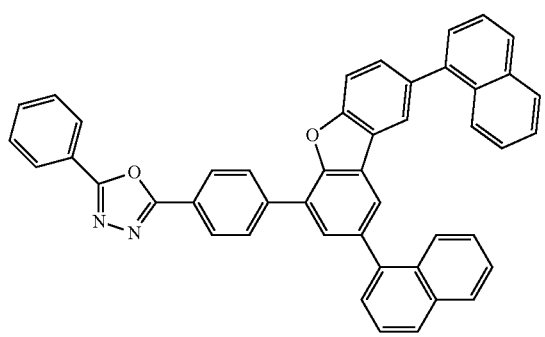
(335)
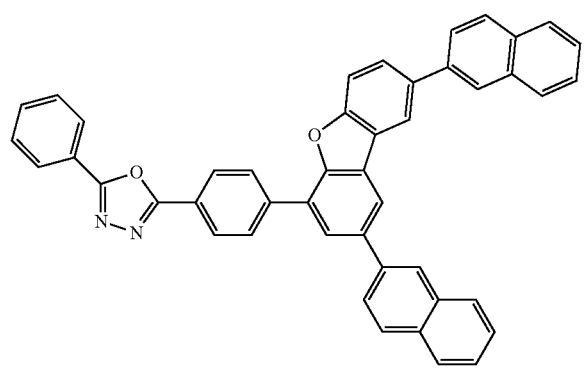
(336)
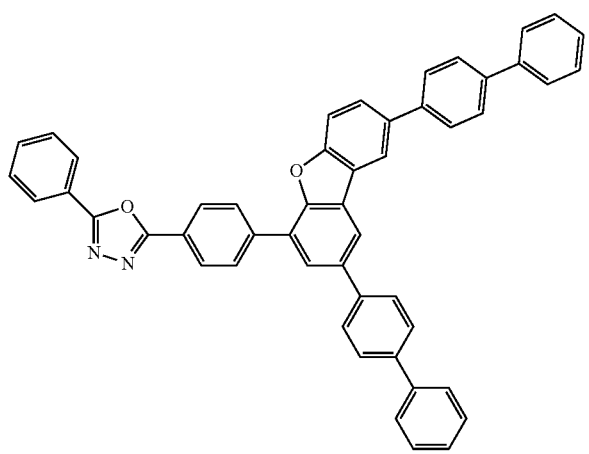
(337)
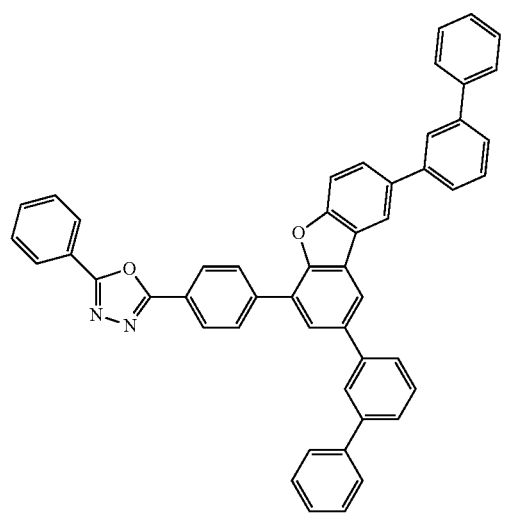

-continued
(338)
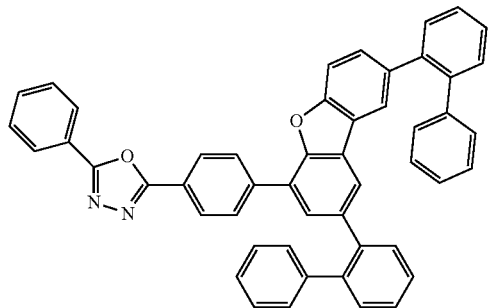
(339)
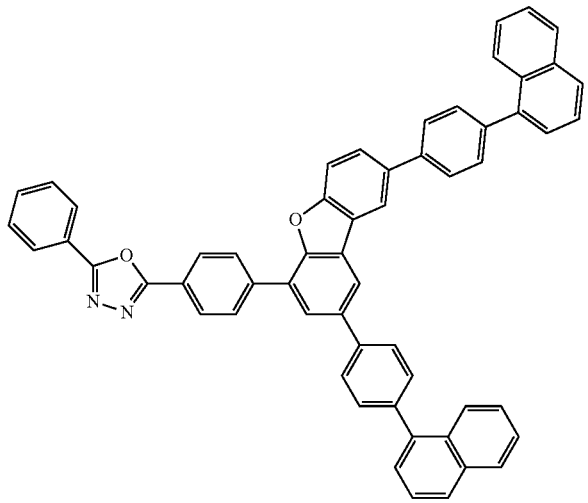
(340)
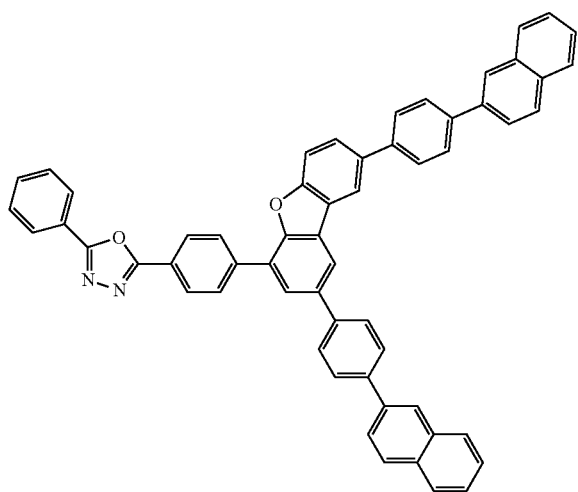
(341)
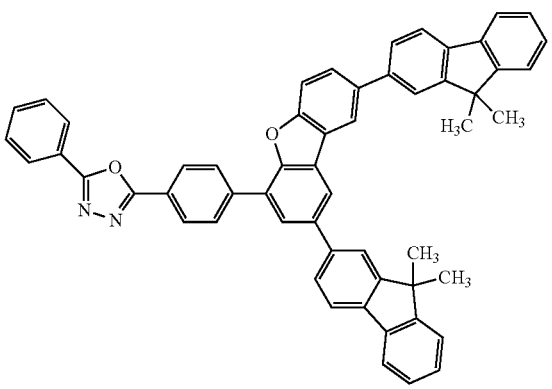
(342)
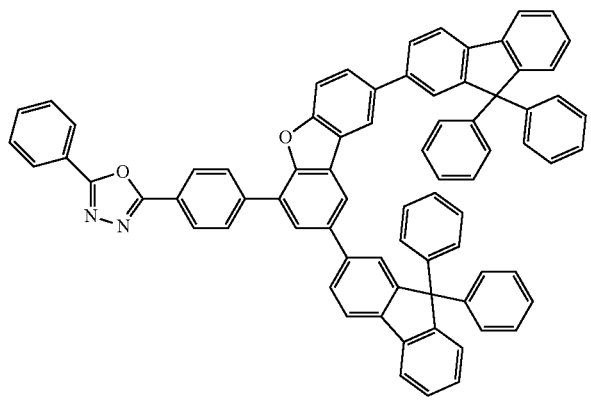
(343)
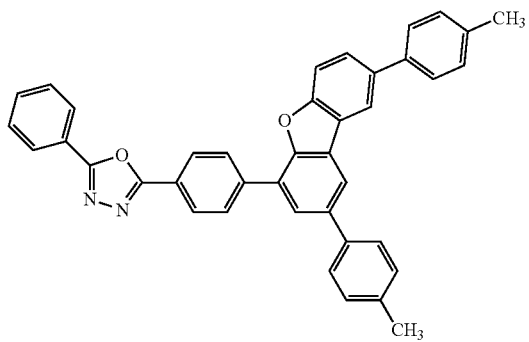

-continued
(344)
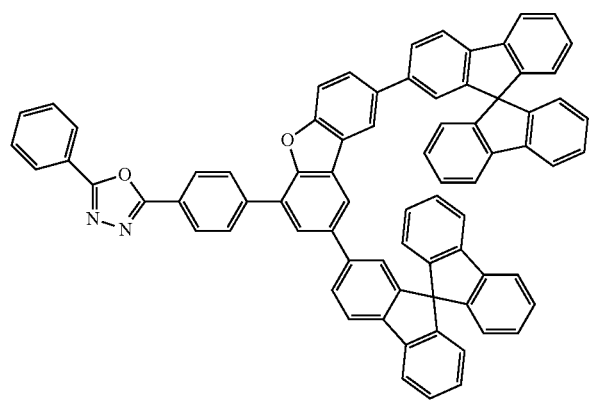
(345)
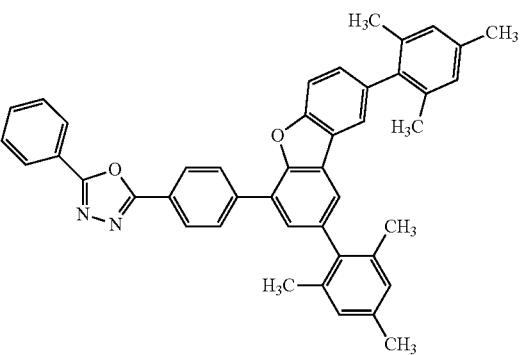
(346)
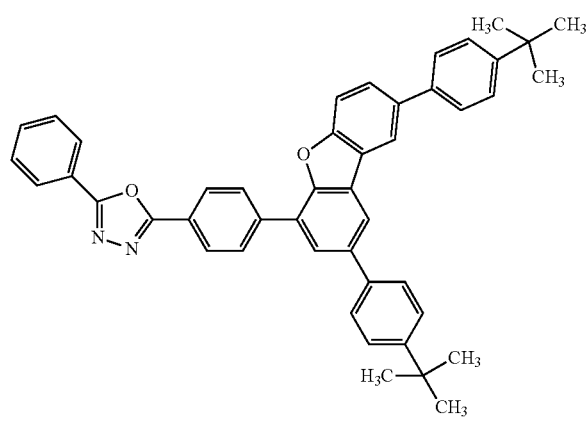
(347)
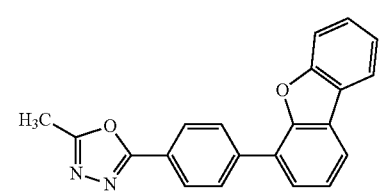
(348)
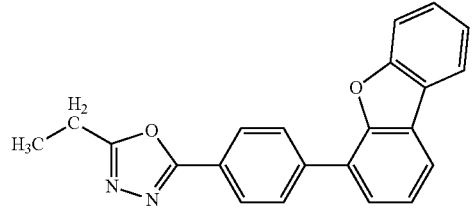
(349)
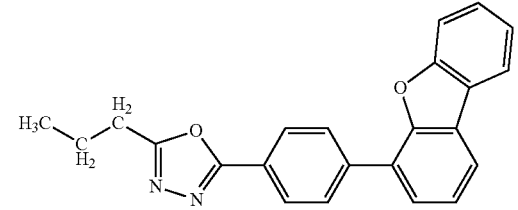
(350)
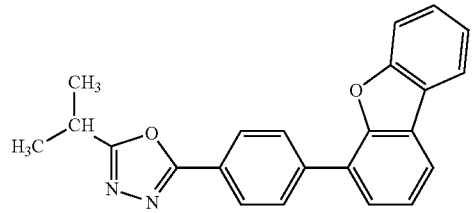
(351)
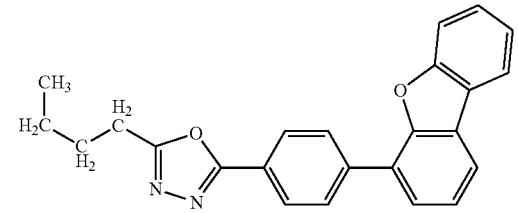
(352)
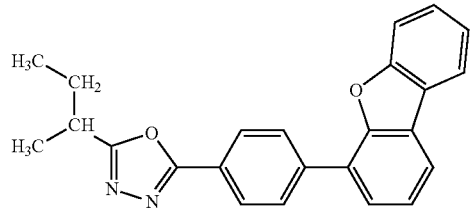
(353)
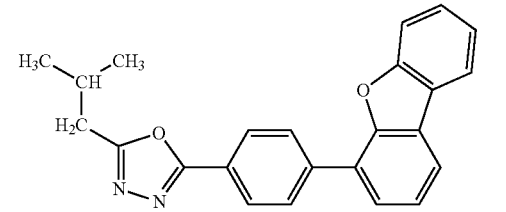

-continued
(354) 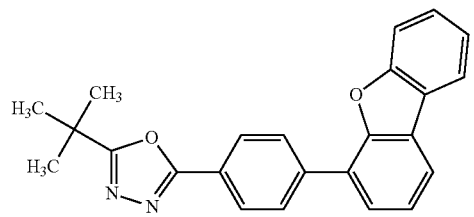
(355) 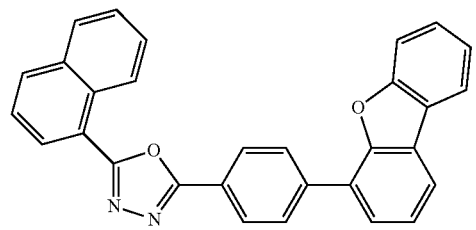
(356) 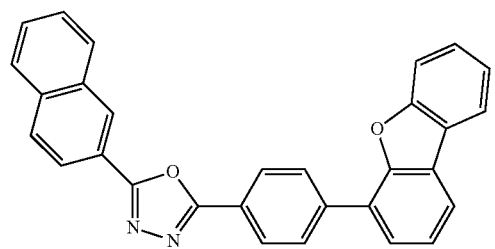
(357) 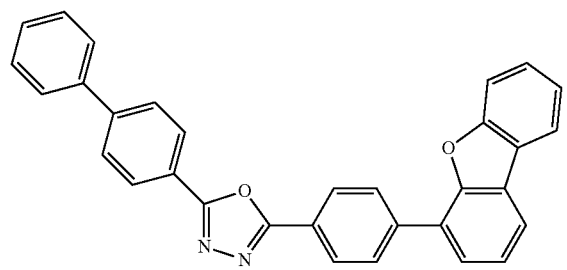
(358) 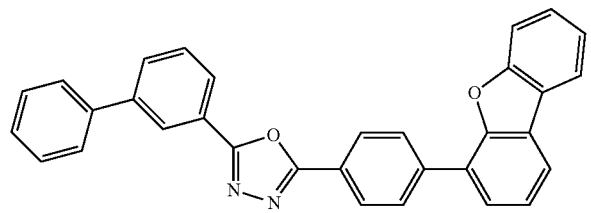
(359) 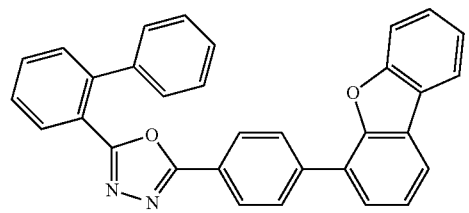
(360) 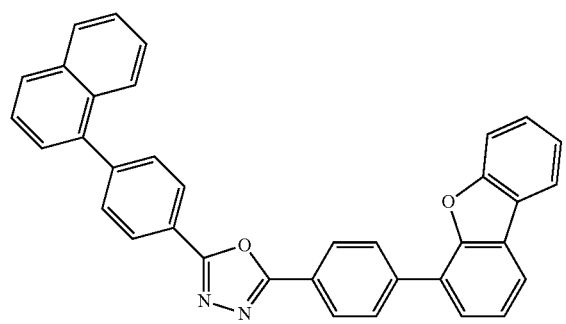
(361) 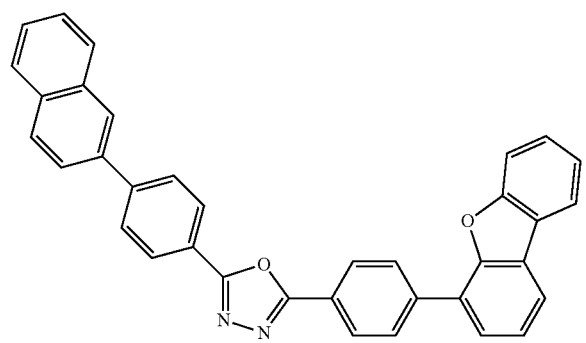
(362) 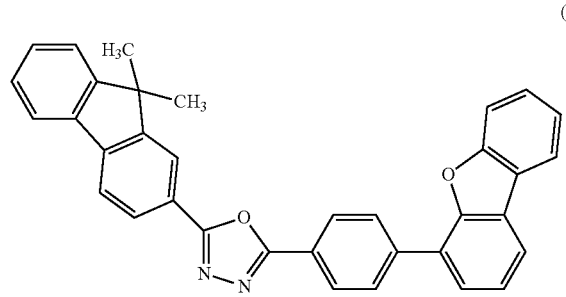
(363) 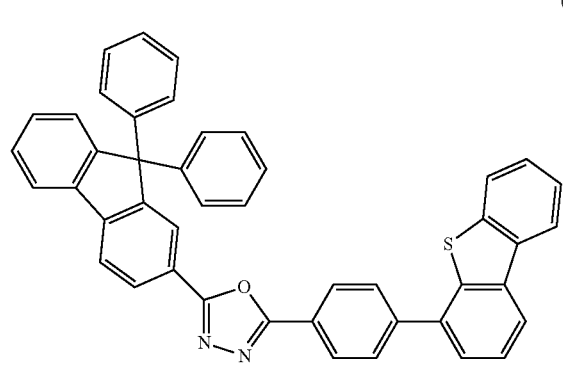

-continued
(364)
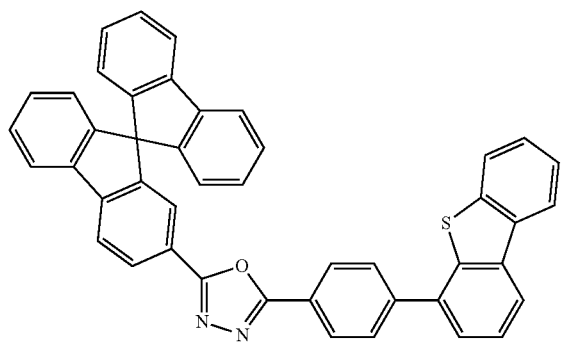
(365)
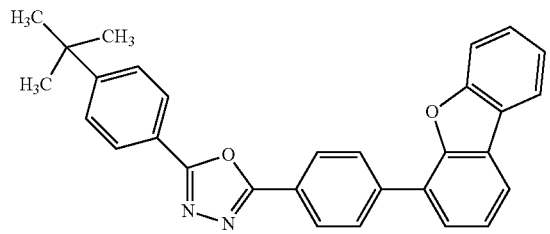
(366)
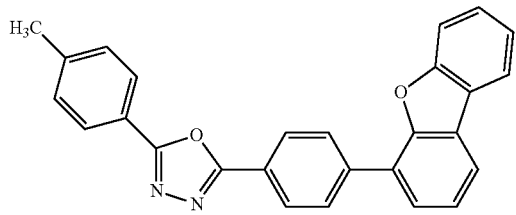
(367)
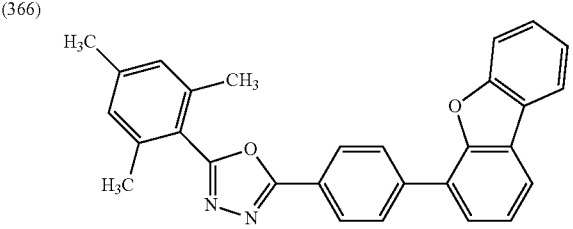
(400)
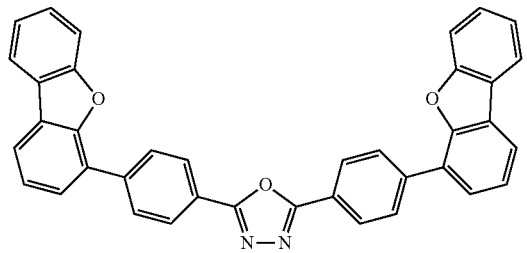
(401)
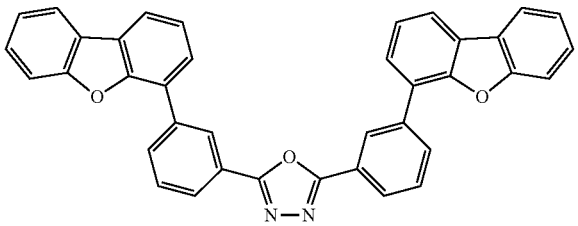
(402)
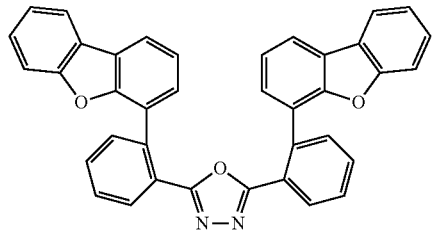
(403)
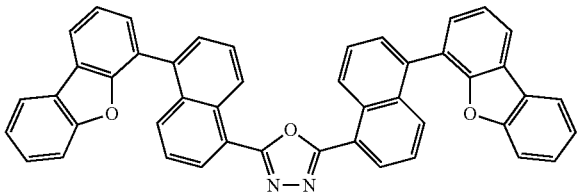
(404)
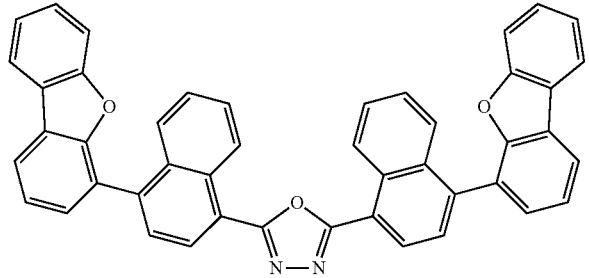
(405)
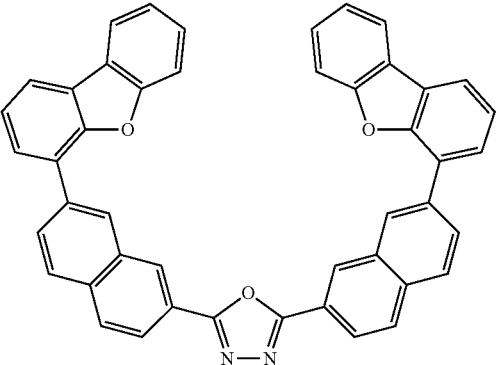

-continued
(406)
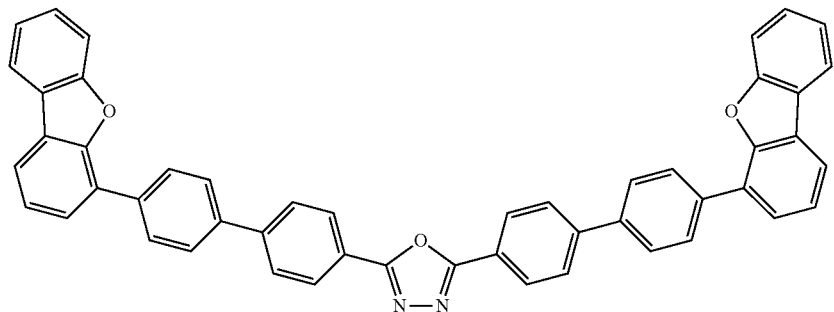
(407) (408)
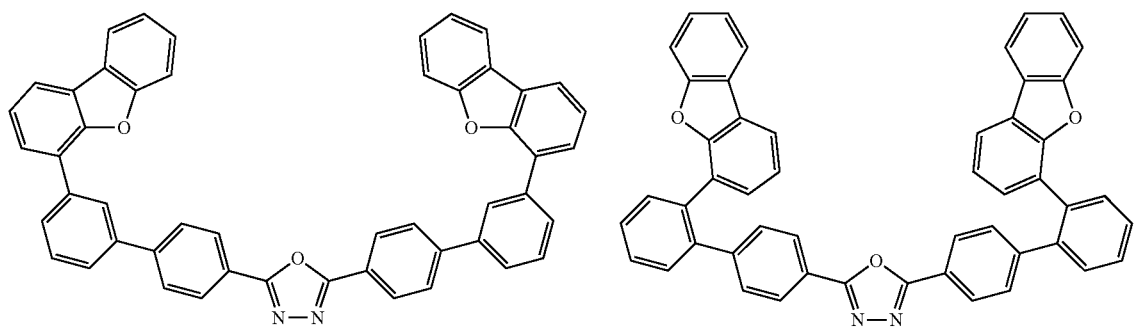
(409)
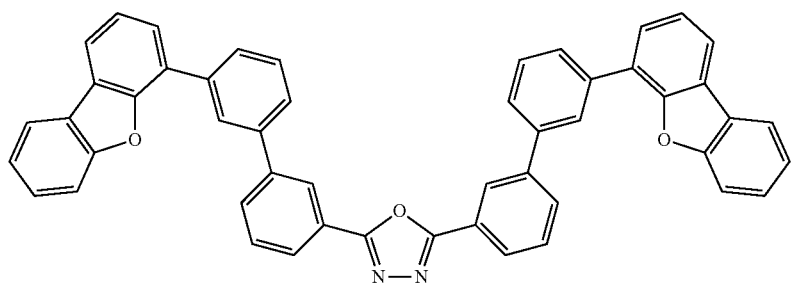
(410) (411)
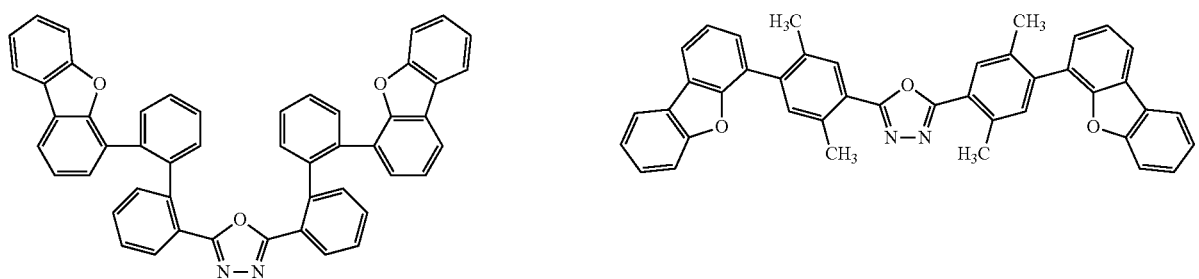
(412)
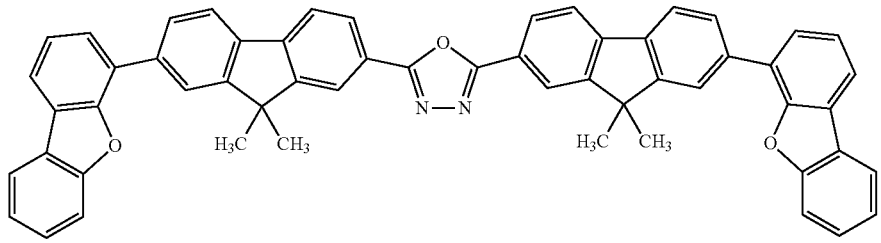

(413)
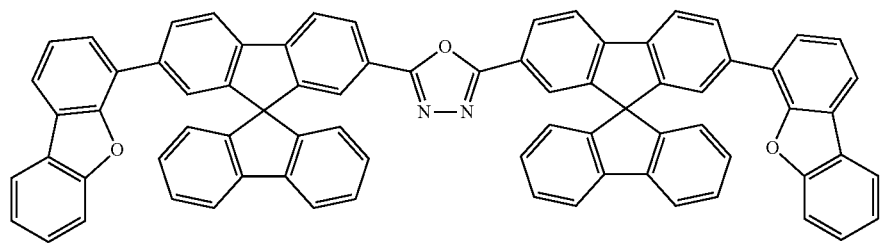
(414)
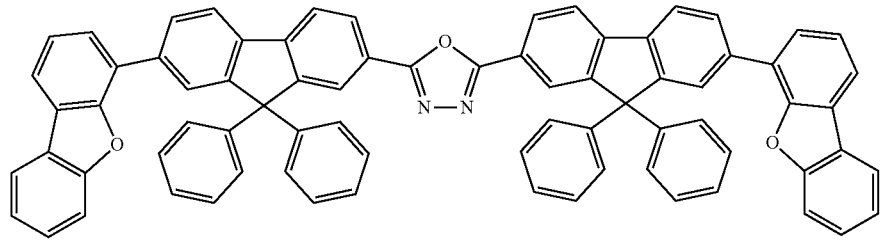
(415) (416)
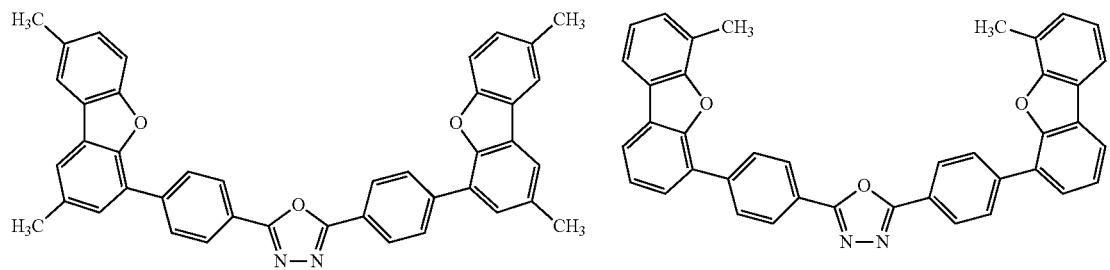
(417)
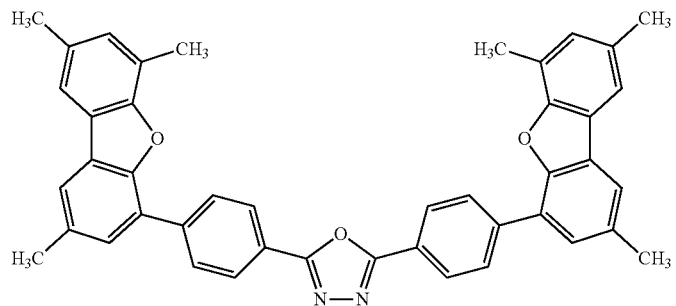
(418)
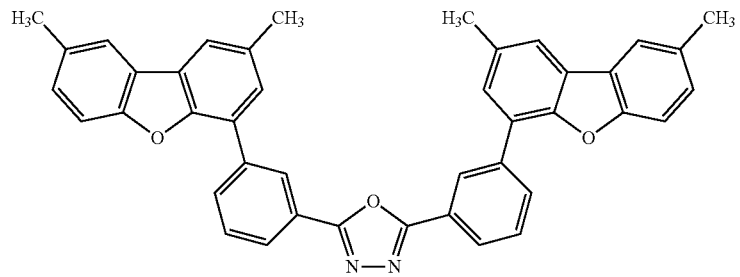
(419)
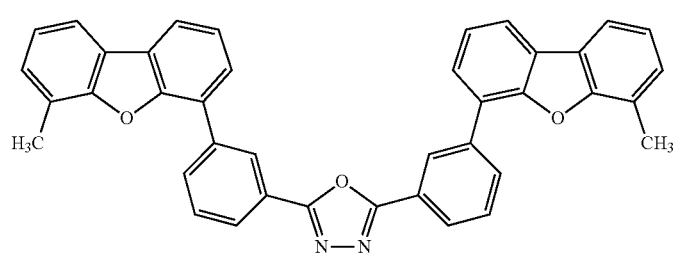

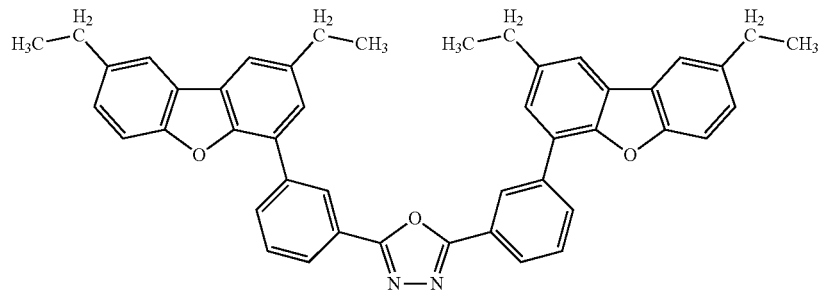
(420)
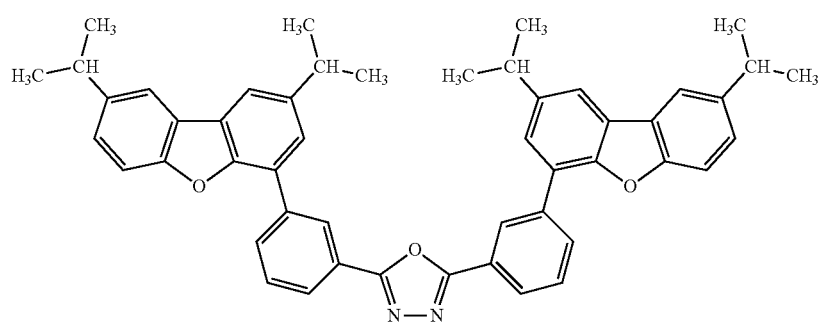
(421)
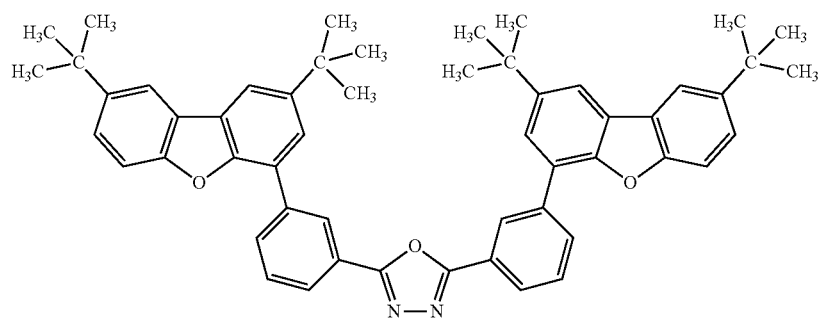
(422)
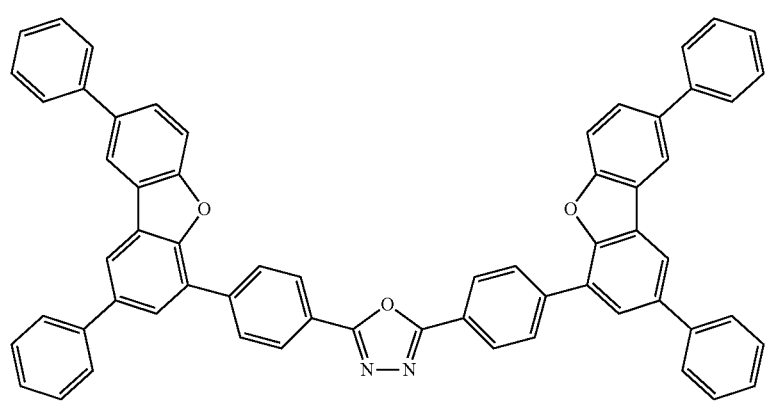
(423)

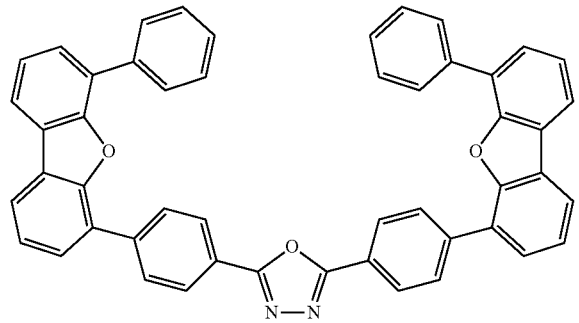
(424)
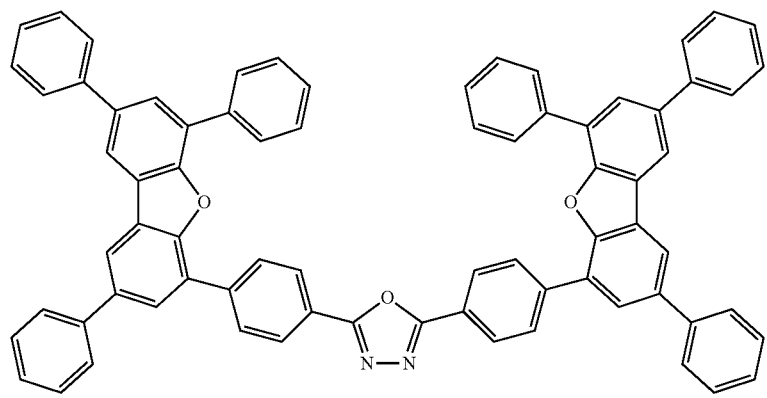
(425)
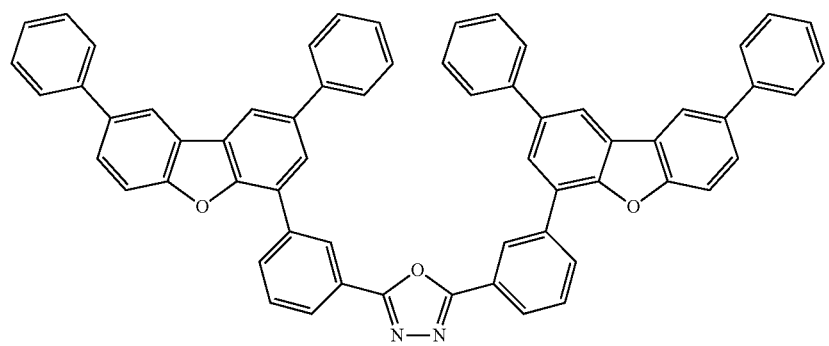
(426)
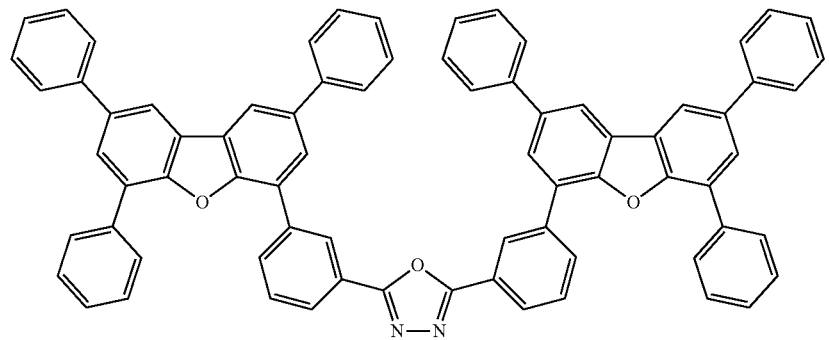
(427)

-continued
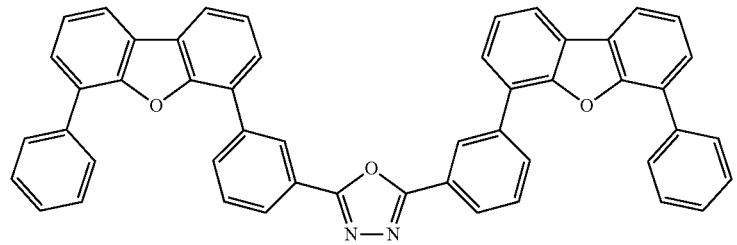
(428)
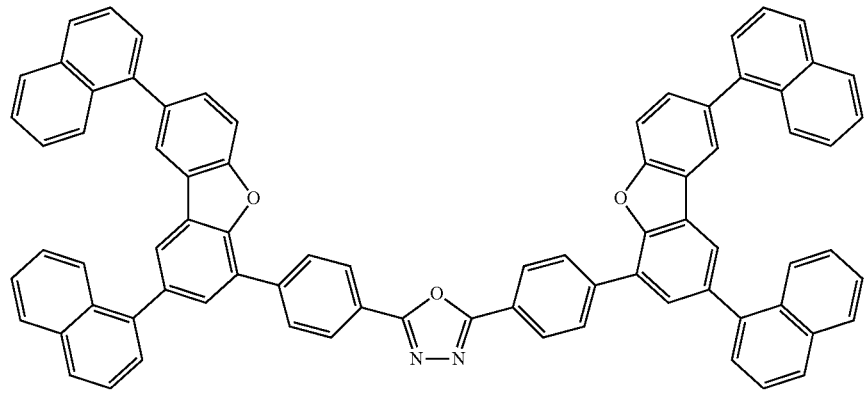
(429)
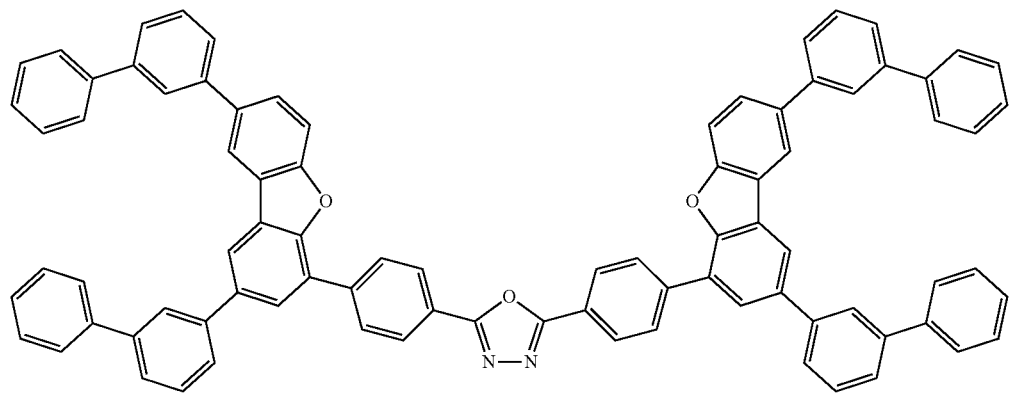
(430)
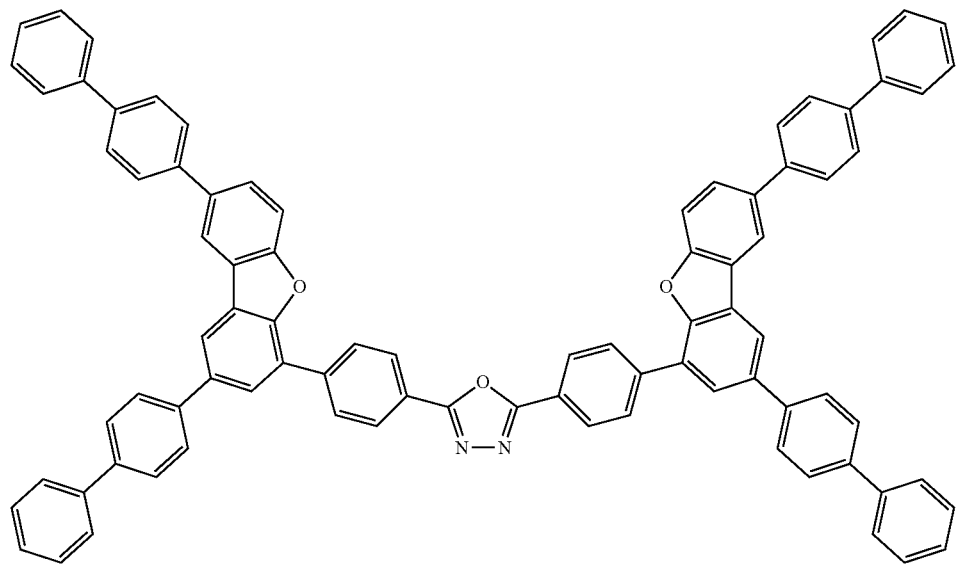
(431)

(432)
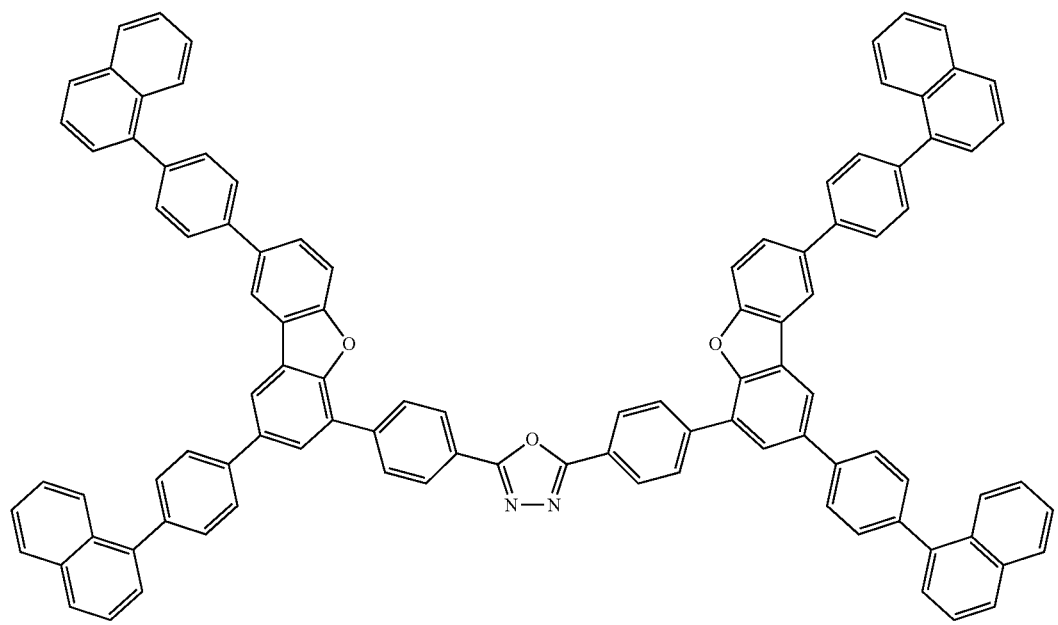
(433)
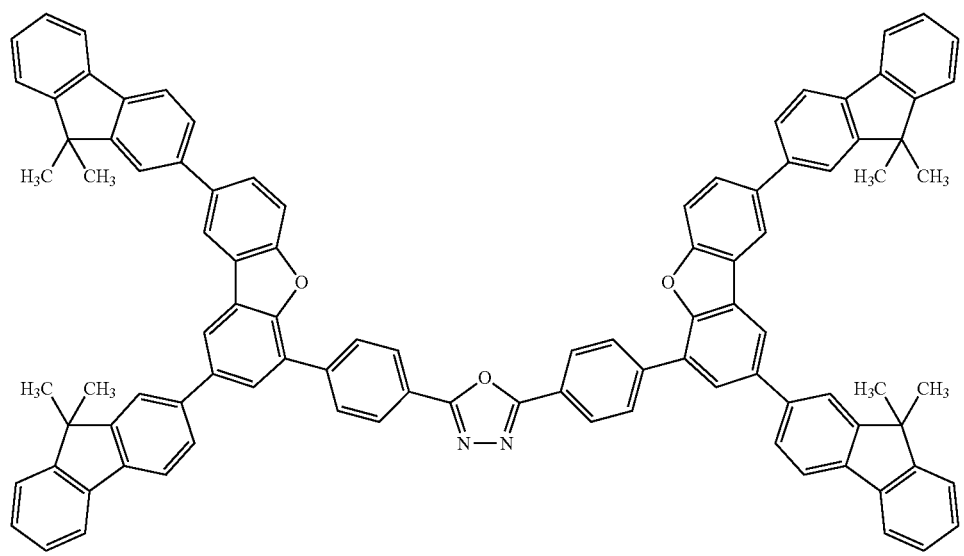

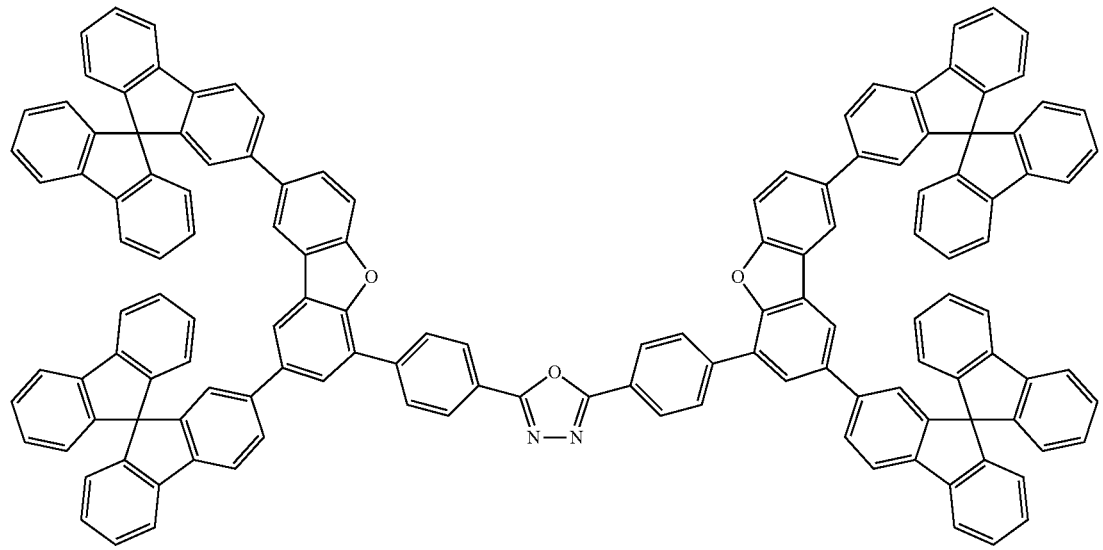
(434)
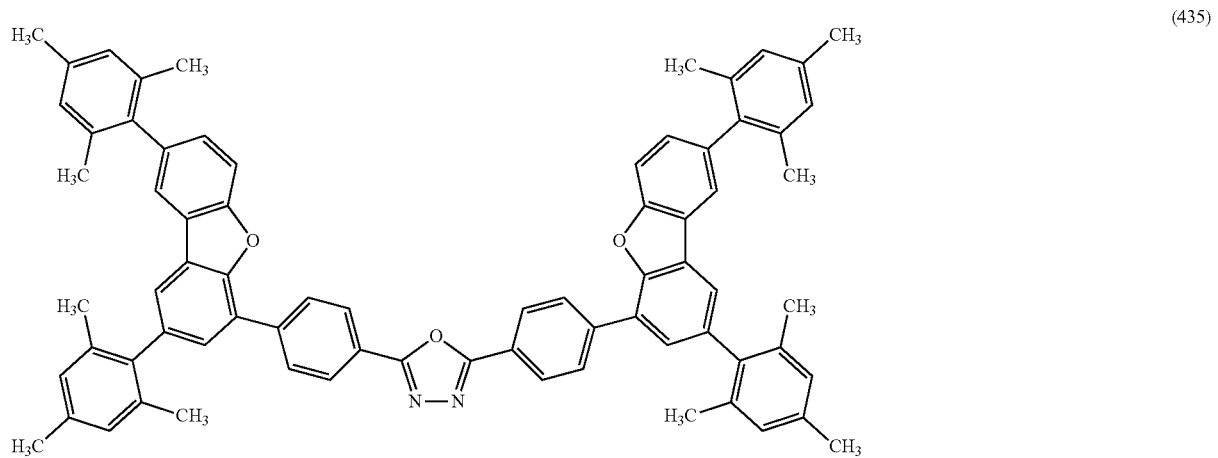
(435)

A variety of reactions can be applied to methods of synthesizing the oxadiazole derivatives of the present invention. For example, the oxadiazole derivative of one embodiment of the present invention, which is represented by General Formula (G1) below, can be synthesized by performing a synthesis reaction described below. Note that methods of synthesizing the oxadiazole derivatives of the present invention are not limited to the following synthesis methods.

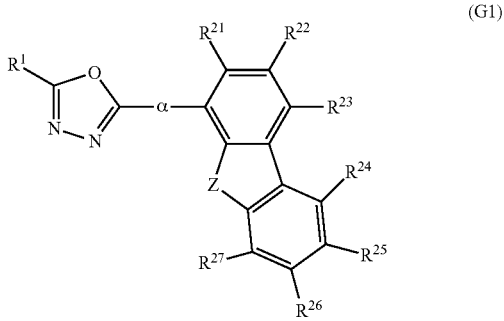

(G1)

Method of Synthesizing Oxadiazole Derivative Represented by General Formula (G1)

The oxadiazole derivative represented by General Formula (G1) can be synthesized as illustrated in Synthesis Scheme (A-1). Specifically, a halide of an oxadiazole derivative (Compound 1) is coupled with an organoboron compound or boronic acid of a dibenzofuran derivative or a dibenzothiophene derivative (Compound 2) by a Suzuki-Miyaura coupling reaction, whereby the oxadiazole derivative (General Formula (G1)) of the present invention can be obtained.

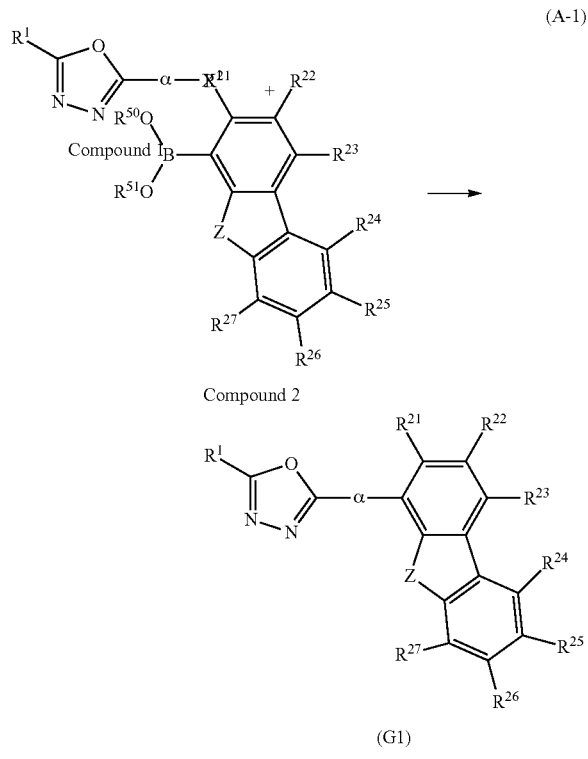

(A-1)

In Synthesis Scheme (A-1), Z represents either a sulfur atom or an oxygen atom; $R^1$ represents either an alkyl group having 1 to 4 carbon atoms or a substituted or unsubstituted aryl group having 6 to 13 carbon atoms; $R^{21}$ to $R^{27}$ separately represent any one of hydrogen, an alkyl group having 1 to 4 carbon atoms, and a substituted or unsubstituted aryl group having 6 to 13 carbon atoms; and α represents a substituted or unsubstituted arylene group having 6 to 13 carbon atoms. $R^{50}$ and $R^{51}$ separately represent either hydrogen or an alkyl group having 1 to 6 carbon atoms. In Synthesis Scheme (A-1), $R^{50}$ and $R^{51}$ may be bonded to each other to form a ring. Furthermore, $X^1$ represents halogen, preferably bromine or iodine.

Examples of a palladium catalyst that can be used in Synthesis Scheme (A-1) are, but not limited to, palladium(II) acetate, tetrakis(triphenylphosphine)palladium(0), bis(triphenylphosphine)palladium(II) dichloride, and the like.

Examples of a ligand of the palladium catalyst that can be used in Synthesis Scheme (A-1) are, but not limited to, tri(ortho-tolyl)phosphine, triphenylphosphine, tricyclohexylphosphine, and the like.

Examples of a base that can be used in Synthesis Scheme (A-1) are, but not limited to, an organic base such as sodium tert-butoxide, an inorganic base such as potassium carbonate or sodium carbonate, and the like.

Examples of a solvent that can be used in Synthesis Scheme (A-1) are, but not limited to, the following solvents: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. In particular, a mixed solvent of toluene and water, a mixed solvent of toluene, ethanol, and water, or a mixed solvent of water and ether such as ethylene glycol dimethyl ether is preferred.

As a coupling reaction in Synthesis Scheme (A-1), the Suzuki-Miyaura coupling reaction using the organoboron compound or the boronic acid represented by Compound 2 may be replaced with a cross coupling reaction using an organoaluminum compound, an organozirconium compound, an organozinc compound, an organotin compound, or the like. However, the present invention is not limited thereto. Further, in this coupling, a triflate group or the like may be used other than halogen; however, the present invention is not limited thereto.

Further, in the Suzuki-Miyaura coupling reaction illustrated in Synthesis Scheme (A-1), an organoboron compound or boronic acid of an oxadiazole derivative may be coupled with a halide of a dibenzofuran derivative or a dibenzothiophene derivative or with a dibenzofuran derivative or a dibenzothiophene derivative which has a triflate group as a substituent by a Suzuki-Miyaura coupling reaction.

The oxadiazole derivative of one embodiment of the present invention, which is represented by General Formula (G2) below, can be synthesized by performing a synthesis reaction described below. Note that methods of synthesizing the oxadiazole derivatives of the present invention are not limited to the following synthesis methods.

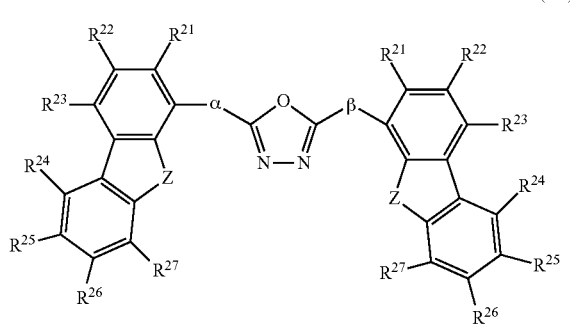

Method of Synthesizing Oxadiazole Derivative Represented by General Formula (G2)

The oxadiazole derivative represented by General Formula (G2) can be synthesized as illustrated in Synthesis Scheme (A-2). Specifically, a halide of an oxadiazole derivative (Compound 3) is coupled with an organoboron compound or boronic acid of a dibenzofuran derivative or a dibenzothiophene derivative (Compound 4) by a Suzuki-Miyaura coupling reaction, whereby the oxadiazole derivative (General Formula (G2)) of the present invention can be obtained.

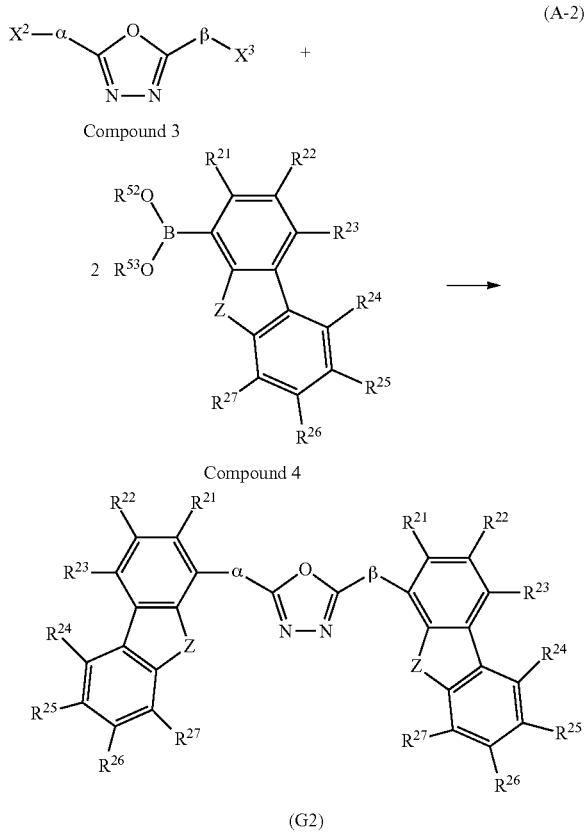

In Synthesis Scheme (A-2), Z represents either a sulfur atom or an oxygen atom; $R^{21}$ to $R^{27}$ separately represent any one of hydrogen, an alkyl group having 1 to 4 carbon atoms, and a substituted or unsubstituted aryl group having 6 to 13 carbon atoms; and α and β separately represent a substituted or unsubstituted arylene group having 6 to 13 carbon atoms. $R^{52}$ and $R^{53}$ separately represent either hydrogen or an alkyl group having 1 to 6 carbon atoms. In Synthesis Scheme (A-2), $R^{52}$ and $R^{53}$ may be bonded to each other to form a ring. Furthermore, $X^2$ and $X^3$ represent halogen, preferably bromine or iodine.

Examples of a palladium catalyst that can be used in Synthesis Scheme (A-2) are, but not limited to, palladium(II) acetate, tetrakis(triphenylphosphine)palladium(0), bis(triphenylphosphine)palladium(II) dichloride, and the like.

Examples of a ligand of the palladium catalyst that can be used in Synthesis Scheme (A-2) are, but not limited to, tri(ortho-tolyl)phosphine, triphenylphosphine, tricyclohexylphosphine, and the like.

Examples of a base that can be used in Synthesis Scheme (A-2) are, but not limited to, an organic base such as sodium tert-butoxide, an inorganic base such as potassium carbonate or sodium carbonate, and the like.

Examples of a solvent that can be used in Synthesis Scheme (A-2) are, but not limited to, the following solvents: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. In particular, a mixed solvent of toluene and water, a mixed solvent of toluene, ethanol, and water, or a mixed solvent of water and ether such as ethylene glycol dimethyl ether is preferred.

As a coupling reaction in Synthesis Scheme (A-2), the Suzuki-Miyaura coupling reaction using the organoboron compound or the boronic acid represented by Compound 4 may be replaced with a cross coupling reaction using an organoaluminum compound, an organozirconium compound, an organozinc compound, an organotin compound, or the like. However, the present invention is not limited thereto. Further, in this coupling, a triflate group or the like may be used other than halogen; however, the present invention is not limited thereto.

Further, in the Suzuki-Miyaura coupling reaction illustrated in Synthesis Scheme (A-2), an organoboron compound or boronic acid of an oxadiazole derivative may be coupled with a halide of a dibenzofuran derivative or a dibenzothiophene derivative or with a dibenzofuran derivative or a dibenzothiophene derivative which has a triflate group as a substituent by a Suzuki-Miyaura coupling reaction.

Embodiment 2

In Embodiment 2, a light-emitting element using any of the oxadiazole derivatives described in Embodiment 1 will be described as one embodiment of the present invention with reference to FIGS. 1A and 1B.

The light-emitting element in Embodiment 2 includes a first electrode which functions as an anode, a second electrode which functions as a cathode, and an EL layer provided between the first electrode and the second electrode. Note that the light-emitting element in Embodiment 2 can provide light emission when voltage is applied to each electrode so that the potential of the first electrode is higher than that of the second electrode.

In addition, the EL layer of the light-emitting element in Embodiment 2 includes a first layer (hole-injection layer), a second layer (hole-transport layer), a third layer (light-emitting layer), a fourth layer (electron-transport layer), and a fifth layer (electron-injection layer), from the first electrode side.

Figure 1B:
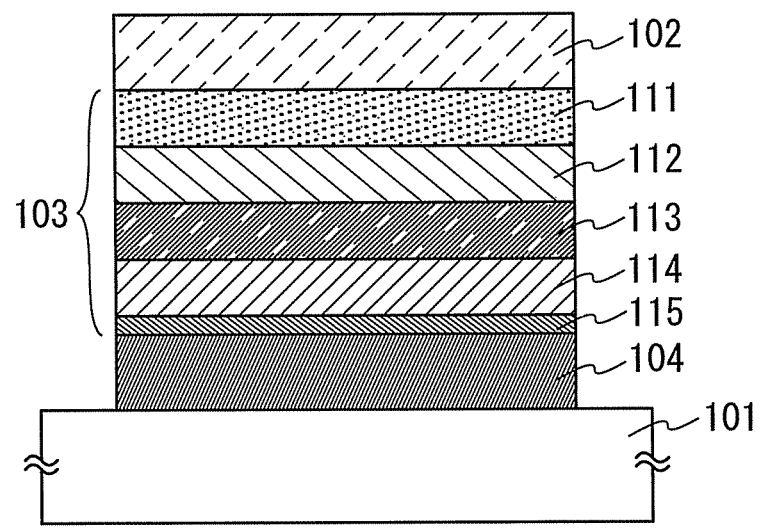

In the light-emitting element in Embodiment 2 described in FIG. 1A or 1B, a substrate 101 is used as a support of the light-emitting element. For the substrate 101, for example, glass, quartz, plastic, or the like can be used. A flexible substrate can also be used. The flexible substrate is a substrate that can be bent, such as a plastic substrate made of polycarbonate, polyarylate, or polyether sulfone, for example. Alternatively a film (made of polypropylene, polyester, polyvinyl fluoride, polyvinyl chloride, or the like), an inorganic film formed by evaporation, or the like can be used. Note that a substrate other than these can be used as long as it can function as a support in a manufacturing process of the light-emitting element.

Note that the above substrate 101 may remain in a light-emitting device or an electronic device which is a product utilizing the light-emitting element of one embodiment of the present invention, but may only functions as the support in its manufacturing process without remaining in an end product.

For a first electrode 102 formed over the substrate 101, any of metals, alloys, conductive compounds, mixtures thereof, and the like which has a high work function (specifically, a work function of 4.0 eV or more) is preferably used. Specific examples include indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like. Films of these conductive metal oxides are usually formed by sputtering, but may be formed by application of a sol-gel method or the like. For example, an indium oxide-zinc oxide (IZO) film can be formed by a sputtering method using a target obtained by adding zinc oxide to indium oxide at 1 wt % to 20 wt %. Further, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Other examples are gold (Au), platinum (Pt), nickel (Ni), tungsten (W), chromium (Cr), molybdenum (Mo), iron (Fe), cobalt (Co), copper (Cu), palladium (Pd), titanium (Ti), a nitride of a metal material (e.g., titanium nitride), and the like.

The first electrode 102 including any of these materials is usually formed by a sputtering method, but may be formed by a vacuum evaporation method, a CVD method, a coating method, an ink-jet method, a printing method, a spin coating method, or the like.

Further, in the EL layer 103 formed over the first electrode 102, when a first layer 111 formed in contact with the first electrode 102 is formed using a later described composite material formed by combining an organic compound and an electron acceptor (acceptor), as a substance used for the first electrode 102, any of a variety of metals, alloys, and conductive compounds, a mixture thereof, or the like can be used regardless of the work function; for example, aluminum (Al), silver (Ag), an alloy containing aluminum (e.g., Al—Si), or the like can also be used.

For the EL layer 103 formed over the first electrode 102, a known substance can be used, and either a low molecular compound or a high molecular compound can be used. Note that substances forming the EL layer 103 may consist of organic compounds or may include an inorganic compound as a part.

The EL layer 103 can be formed by stacking an appropriate combination of a hole-injection layer that includes a substance having a high hole-injection property, a hole-transport layer that includes a substance having a high hole-transport property, a light-emitting layer that includes a light-emitting substance, an electron-transport layer that includes a substance having a high electron-transport property, an electron-injection layer that includes a substance having a high electron-injection property, and the like. In FIGS. 1A and 1B, an EL layer is described in which the first layer (hole-injection layer) 111, a second layer (hole-transport layer) 112, a third layer (light-emitting layer) 113, a fourth layer (electron-transport layer) 114, and a fifth layer (electron-injection layer) 115 are stacked in this order from the first electrode 102 side.

The first layer 111 which is the hole-injection layer is a layer including a substance having a high hole-injection property. Examples of a substance having a high hole-injection property that can be used are molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide. Besides, as a low molecular organic compound, a phthalocyanine-based compound such as phthalocyanine (abbreviation: $H_2Pc$), copper(II) phthalocyanine (abbreviation: CuPc), or vanadyl phthalocyanine (abbreviation: VOPc) can be used.

Other examples of a substance that can be used are aromatic amine compounds which are low molecular organic compounds, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Still other examples of a substance that can be used are high molecular compounds (e.g., oligomers, dendrimers, and polymers), such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD), and high molecular compounds to which acid is added, such as poly(3,4-ethylenedioxythiophene)/poly(styrenesulfonic acid) (PEDOT/PSS), or polyaniline/poly(styrenesulfonic acid) (PAni/PSS).

For the first layer 111, a composite material formed by combining an organic compound and an electron acceptor (acceptor) may be used. Such a composite material, in which holes are generated in the organic compound by the electron acceptor, has an excellent hole-injection and hole-transport properties. In this case, the organic compound is preferably a material excellent in transporting the generated holes (a substance having a high hole-transport property). Note that when such a composite material is used, a material for forming the first electrode 102 can be selected regardless of its work function. In other words, besides a material with a high work function, a material with a low work function can also be used for the first electrode 102. In the case where the first layer 111 is formed using such a composite material, an organic compound and an electron acceptor (acceptor) may be co-evaporated.

Examples of the organic compound used for the composite material are a variety of compounds such as aromatic amine compounds, carbazole derivatives, aromatic hydrocarbons, and high molecular compounds (e.g., oligomers, dendrimers, and polymers). The organic compound used for the composite material is preferably organic compounds having a high hole-transport property, and specifically preferably a substance having hole mobility of $10^{-6}$ cm$^2$/Vs or more. Note that other than these substances, any substance that has a property of transporting more holes than electrons may be used. Organic compounds that can be used for the composite material will be specifically described below.

Examples of an organic compound that can be used for the composite material are aromatic amine compounds such as MTDATA, TDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD), and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N-carbazolyl)phenyl-2,3,5,6-tetraphenylbenzene.

Other examples of an organic compound that can be used are aromatic hydrocarbon compounds such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Other examples of an organic compound that can be used are aromatic hydrocarbon compounds, such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

Further, examples of the electron acceptor (accpetor) are organic compounds such as 7,7,8,8-tetracyano-2,3,5,6-tetrafluoroquinodimethane (abbreviation: F$_4$-TCNQ) and chloranil, transition metal oxides, and oxides of metals that belong to Groups 4 to 8 in the periodic table. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air, has a low hygroscopic property, and is easily treated.

The composite material may be formed using the above-described electron acceptor (acceptor) and the above-described high molecular compound such as PVK, PVTPA, PTPDMA, or Poly-TPD and used for the first layer 111.

The second layer 112 which is the hole-transport layer is a layer that includes a substance having a high hole-transport property. As the substance having a high hole-transport property, particularly as a low molecular organic compound, an aromatic amine compound such as NPB (or α-NPD), TPD, 4,4'-bis[N-(9,9-dimethylfluoren-2-yl)-N-phenylamino]biphenyl (abbreviation: DFLDPBi), or 4,4'-bis[N-(spiro-9,9'-bifluoren-2-yl)-N-phenylamino]biphenyl (abbreviation: BSPB) can be used. The substances mentioned here are mainly substances that have hole mobility of $10^{-6}$ cm$^2$/Vs or more. Note that other than the above substances, any substance that has a property of transporting more holes than electrons may be used. Further, the layer including a substance having a high hole-transport property is not limited to a single layer, and may be a stack of two or more layers including any of the above substances.

Alternatively, for the second layer 112, a composite material in which an electron acceptor (acceptor) is included in the above-described substance having a high hole-transport property may be used.

For the second layer 112, a high molecular compound such as PVK, PVTPA, PTPDMA, or Poly-TPD can be used.

The third layer 113 which is the light-emitting layer is a layer including a light-emitting substance. As the light-emitting substance, for example, a fluorescent compound which emits fluorescence or a phosphorescent compound which emits phosphorescence can be used. Note that in this embodiment, the case where the oxadiazole derivative which is one embodiment of the present invention is used for the light-emitting layer is described. For the light-emitting layer in which a substance having a high light-emitting property (a guest material) is dispersed in another substance (a host material), the oxadiazole derivative which is one embodiment of the present invention can be used as the host material.

In the case where the oxadiazole derivative which is one embodiment of the present invention is used as the host material and a substance which emits fluorescence is used as the guest material in the light-emitting layer, it is preferable to use, as the guest material, a substance whose lowest unoccupied molecular orbital level (LUMO level) is lower and highest occupied molecular orbital level (HOMO level) is higher than those of the oxadiazole derivative. Examples of materials for blue light emission include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and the like. Examples of materials for green light emission include N-(9,10-diphenyl-2-anthryl)-N, 9-diphenyl-9H-carbazol-3-amine (abbreviation: 2PCAPA), N-[9,10-bis(1,1'-biphenyl-2-yl)-2-anthryl]-N, 9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Examples of materials for yellow light emission include rubrene, 5,12-bis(1,1'-biphenyl-4-yl)-6,11-diphenyltetracene (abbreviation: BPT), and the like. Examples of materials for red light emission include N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), and the like.

Alternatively, in the case where the oxadiazole derivative which is one embodiment of the present invention is used as the host material and a substance which emits phosphorescence is used as the guest material in the light-emitting layer, it is preferable to use, as the guest material, a substance having lower triplet excitation energy than the oxadiazole derivative. For example, the following organometallic complexes can be used, such as bis[2-(2'-benzo[4,5-α]thienyl)pyridinato-N,C$^3$']iridium(III)acetylacetonate (abbreviation:

Ir(btp)$_2$(acac)), bis(1-phenylisoquinolinato-N,C$^{2'}$)iridium (III)acetylacetonate (abbreviation: Ir(piq)$_2$(acac)), (acetylacetonato)bis[2,3-bis(4-fluorophenyl)quinoxalinato]iridium (III) (abbreviation: Ir(Fdpq)$_2$(acac)), and 2,3,7,8,12,13,17,18-octaethyl-21H,23H-porphyrin platinum(II) (abbreviation: PtOEP).

Since the oxadiazole derivatives described which are embodiments of the present invention have an electron-transport property, using any of them in a light-emitting layer achieves its high electron-transport property. Such a light-emitting layer can provide light emission with high efficiency by using a guest material with high electron-trapping property.

In addition, as a substance (host material) in which a light-emitting substance (guest material) is dispersed, plural kinds of substances can be used. Therefore, the light-emitting layer may include a second host material in addition to the oxadiazole derivatives which are embodiments of the present invention. Note that as the second host material, a known host material can be used.

The fourth layer 114 which is the electron-transport layer is a layer which includes a substance having a high electron-transport property. Examples of the substance having a high electron-transport property used for the fourth layer 114 which can be used are: metal complexes having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]-quinolinato)beryllium (abbreviation: BeBq$_2$), and bis(2-methyl-8-quinolinolato)(4-phenylphenolato)aluminum (abbreviation: BAlq); and the like. In addition, a metal complex having an oxazole ligand or a thiazole ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can also be used. In addition to the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can be used. Alternatively, a high molecular compound such as poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can be used.

Since the oxadiazole derivatives which are embodiments of the present invention have an electron-transport property, they can also be used for an electron-transport layer.

The substances described here are mainly substances having electron mobility of 10$^{-6}$ cm$^2$/Vs or more. Further, the electron-transport layer is not limited to a single layer and may be a stacked layer which includes two or more layers including the above-described substances.

The fifth layer 115 which is the electron-injection layer is a layer that includes a substance having a high electron-injection property. For the fifth layer 115, an alkali metal, an alkaline earth metal, or a compound thereof, such as lithium fluoride (LiF), cesium fluoride (CsF), or calcium fluoride (CaF$_2$), can be used. Alternatively, a rare earth metal compound such as erbium fluoride can be used.

Alternatively, a composite material in which an organic compound and an electron donor (donor) are mixed may be used for the electron-injection layer. Such a composite material is excellent in an electron-injection property and an electron-transport property because electrons are generated in the organic compound by the electron donor. In this case, the organic compound is preferably a material excellent in transporting the generated electrons. Specifically, the above substances for forming the electron-transport layer (e.g., a metal complex or a heteroaromatic compound) can be used, for example. As the electron donor, a substance exhibiting an electron-donating property to the organic compound may be used. Specifically, it is preferable to use an alkali metal, an alkaline earth metal, or a rare earth metal, such as lithium, cesium, magnesium, calcium, erbium, ytterbium, or the like. Further, it is preferable to use an alkali metal oxide or an alkaline earth metal oxide, such as lithium oxide, calcium oxide, or barium oxide. Alternatively, a Lewis base such as magnesium oxide can also be used. Further alternatively, an organic compound such as tetrathiafulvalene (abbreviation: TTF) can be used.

Note that the first layer (hole-injection layer) 111, the second layer (hole-transport layer) 112, the third layer (light-emitting layer) 113, the fourth layer (electron-transport layer) 114, and the fifth layer (electron-injection layer) 115 which are included in the above-described EL layer 103 can each be formed by an evaporation method (including a vacuum evaporation method), an ink jet method, a coating method, or the like. Note that a different formation method may be employed for each layer.

The second electrode 104 can be foamed using a metal, an alloy, a conductive compound, a mixture thereof, or the like which has a low work function (specifically, a work function of 3.8 eV or less). Specifically, any of the following materials can be used: elements that belong to Group 1 or Group 2 in the periodic table, that is, alkali metals such as lithium (Li) and cesium (Cs), alkaline earth metals such as magnesium (Mg), calcium (Ca), and strontium (Sr), alloys thereof (e.g., Mg—Ag and Al—Li), rare earth metals such as europium (Eu) and ytterbium (Yb), alloys thereof, and the like.

Note that in the case where a layer formed in contact with the second electrode 104 which is included in the EL layer 103 is formed using the above-described composite material formed by combining the organic compound and the electron donor (donor), any of a variety of conductive materials such as aluminum, silver, ITO, indium oxide-tin oxide containing silicon or silicon oxide can be used regardless of the work function.

Note that the second electrode 104 can be formed by a vacuum evaporation method or a sputtering method. Alternatively, a coating method, an ink-jet method, a spin coating method, or the like can be employed depending on a material to be used.

In the above-described light-emitting element of the present invention, a current flows because of a potential difference generated between the first electrode 102 and the second electrode 104 and holes and electrons recombine in the EL layer 103, so that light is emitted. Then, this emitted light is extracted out through one or both of the first electrode 102 and the second electrode 104. Accordingly, one or both of the first electrode 102 and the second electrode 104 is/are an electrode having a light-transmitting property.

Note that the structure of the layer provided between the first electrode 102 and the second electrode 104 is not limited to the above structure. A structure other than the above may also be employed as long as a light-emitting region in which holes and electrons recombine is provided in a portion away from the first electrode 102 and the second electrode 104 in order to prevent quenching due to proximity of the light-emitting region to a metal.

In other words, a stacked structure of the layer is not particularly limited, and a layer formed of a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like may freely be combined with a light-emitting layer.

Alternatively, as illustrated in FIG. 1B, a structure may be employed in which the second electrode 104 functioning as a cathode, the EL layer 103, and the first electrode 102 functioning as an anode are stacked in that order over the substrate 101. Note that the EL layer 103 in this case has a structure in which the fifth layer 115, the fourth layer 114, the third layer 113, the second layer 112, the first layer 111, and the first electrode 102 are stacked in that order over the second electrode 104.

As described above, the light-emitting element can be manufactured using the oxadiazole derivative which is one embodiment of the present invention. Note that when the light-emitting element can be manufactured using the oxadiazole derivative which is one embodiment of the present invention, a light-emitting element having high emission efficiency can be realized. In addition, a light-emitting element with long lifetime can be obtained.

Note that with the use of the light-emitting element manufactured using any of the oxadiazole derivatives which are embodiments of the present invention, a passive matrix light-emitting device or an active matrix light-emitting device can be fabricated.

Note that there is no particular limitation on the structure of a TFT in the case of manufacturing an active matrix light-emitting device. For example, a staggered TFT or an inverted staggered TFT can be used as appropriate. Further, a driver circuit formed over a TFT substrate may be formed using both of an n-type TFT and a p-type TFT or only either an n-type TFT or a p-type TFT. Furthermore, there is no particular limitation on the crystallinity of a semiconductor film used for the TFT. An amorphous semiconductor film may be used, or a crystalline semiconductor film may be used.

Note that this embodiment can be used in combination with any of the structures described in the other embodiments as appropriate.

Embodiment 3

Figure 2:
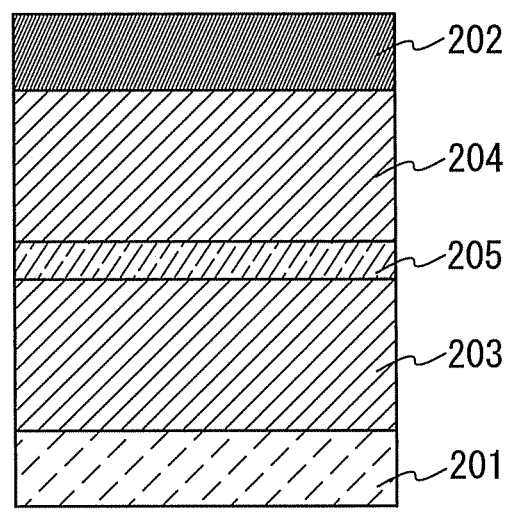
FIG. 2 illustrates a light-emitting element of one embodiment of the present invention.

In this embodiment, a light-emitting element having a stack of plural EL layers of the light-emitting elements described in Embodiment 2 (hereinafter, referred to as a stacked-type element) is described using FIG. 2. This light-emitting element is a stacked-type light-emitting element that has a plurality of EL layers (a first EL layer 203 and a second EL layer 204) between a first electrode 201 and a second electrode 202. Note that although a structure in which two EL layers are formed is described in this embodiment, three or more EL layers may be formed.

In this embodiment, the first electrode 201 functions as an anode, and the second electrode 202 functions as a cathode. Note that for the first electrode 201 and the second electrode 202, structures similar to those described in Embodiment 2 can be employed. Further, for the plurality of EL layers (the first EL layer 203 and the second EL layer 204), structures similar to those described in Embodiment 2 can be employed. Note that structures of the first EL layer 203 and the second EL layer 204 may be the same or different from each other and can be similar to those described in Embodiment 2.

Further, a charge generation layer 205 is provided between the plurality of EL layers (the first EL layer 203 and the second EL layer 204). The charge generation layer 205 has a function of injecting electrons into one of the EL layers and injecting holes into the other of the EL layers when voltage is applied to the first electrode 201 and the second electrode 202. In this embodiment, when voltage is applied so that the potential of the first electrode 201 is higher than that of the second electrode 202, the charge generation layer 205 injects electrons into the first EL layer 203 and injects holes into the second EL layer 204.

Note that the charge generation layer 205 preferably has a light-transmitting property in terms of light extraction efficiency. Further, the charge generation layer 205 functions even when it has lower electric conductivity than the first electrode 201 or the second electrode 202.

The charge generation layer 205 may have either a structure including an organic compound having a high hole-transport property and an electron acceptor (acceptor) or a structure including an organic compound having a high electron-transport property and an electron donor (donor). Alternatively, both of these structures may be stacked. Note that the electron acceptor and the electron donor are at least capable of donating and accepting electrons with the assistance of an electric field.

In the case of the structure in which an electron acceptor is added to an organic compound having a high hole-transport property, examples of the substances having a high hole-transport property which can be used include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), and the like. The substances described here are mainly materials having hole mobility of $10^{-6}$ $cm^2/Vs$ or more. However, any substance other than the above substances may be used as long as it is a substance in which the hole-transport property is higher than the electron-transport property.

In addition, examples of the electron acceptor include 7,7,8,8-tetracyano-2,3,5,6-tetrafluoroquinodimethane (abbreviation: $F_4$-TCNQ), chloranil, and transition metal oxides. Other examples are oxides of metals belonging to Group 4 to Group 8 in the periodic table. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easily handled.

On the other hand, in the case of the structure in which an electron donor is added to an organic compound having a high electron-transport property, examples of the substances having a high electron-transport property which can be used include a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq), and the like. Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)-benzothiazolato]zinc (abbreviation: Zn(BTZ)$_2$), or the like can be used. Besides the metal complexes, 2-(4-biphenylyl)-5-(4-tert-butylphenyl)-1,3,4-oxadiazole (abbreviation: PBD), 1,3-bis[5-

(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances described here are mainly substances having electron mobility of $10^{-6}$ cm$^2$/Vs or more. Note that any substance other than the above substances may be used as long as it is a substance in which the electron-transport property is higher than the hole-transport property.

Examples of the electron donor that can be used are alkali metals, alkaline earth metals, rare earth metals, metals that belong to Group 13 in the periodic table and oxides or carbonates thereof, and preferably specifically lithium (Li), cesium (Cs), magnesium (Mg), calcium (Ca), ytterbium (Yb), indium (In), lithium oxide, cesium carbonate, and the like. An organic compound such as tetrathianaphthacene may be used as the electron donor.

By forming the charge generation layer 205 with any of the above materials, it is possible to suppress an increase in driving voltage caused when the EL layers are stacked.

Although the light-emitting element including two EL layers is described in this embodiment, the embodiment can be applied to a light-emitting element in which three or more EL layers are stacked. When a plurality of EL layers with a charge generation layer interposed therebetween is arranged between a pair of electrodes, as in the light-emitting element of this embodiment, it is possible to realize an element which can emit light in a high luminance region while current density is kept low. Since the current density can be kept low, the element can have a long lifetime. When the light-emitting element is applied for illumination, voltage drop due to resistance of an electrode material can be reduced, whereby uniform light emission in a large area is possible. Moreover, a light-emitting device with low driving voltage and low power consumption can be achieved.

Furthermore, by making emission colors of the EL layers different, light having a desired color can be obtained from the light-emitting element as a whole. For example, the emission colors of first and second EL layers are complementary in a light-emitting element including the two EL layers, so that the light-emitting element can be made to emit white light as a whole. Note that the term "complementary" means color relationship in which an achromatic color is obtained when colors are mixed. That is, emission of white light can be obtained by mixture of light emitted from substances whose emission colors are complementary colors.

Further, the same can be applied to a light-emitting element including three EL layers. For example, the light-emitting element as a whole can emit white light when the emission color of the first EL layer is red, the emission color of the second EL layer is green, and the emission color of the third EL layer is blue.

Note that Embodiment 3 can be combined with any of the structures described in Embodiments 1 and 2 as appropriate.

Embodiment 4

In Embodiment 4, a light-emitting device having a light-emitting element of one embodiment of the present invention in a pixel portion will be described with reference to FIGS. 3A and 3B. Note that FIG. 3A is a top view illustrating the light-emitting device, and FIG. 3B is a cross-sectional view taken along lines A-A' and B-B' of FIG. 3A.

Figure 3A:
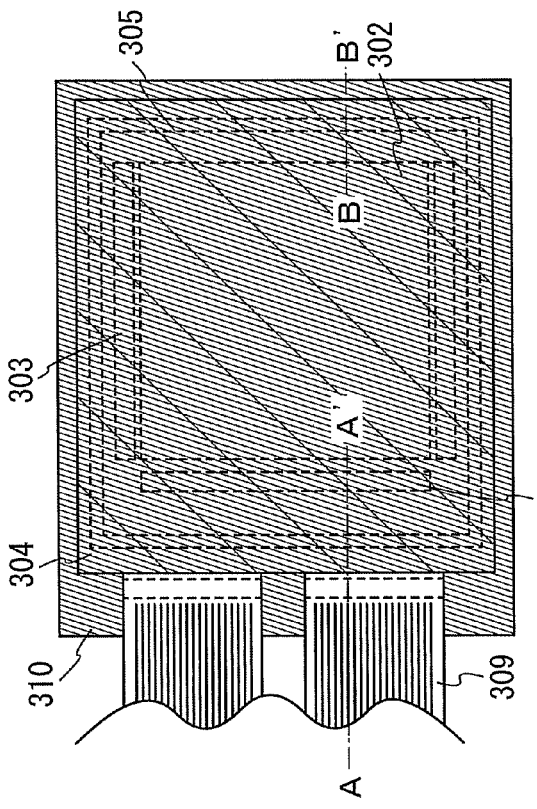
FIGS. 3A and 3B illustrate a light-emitting device of one embodiment of the present invention.
Figure 3B:
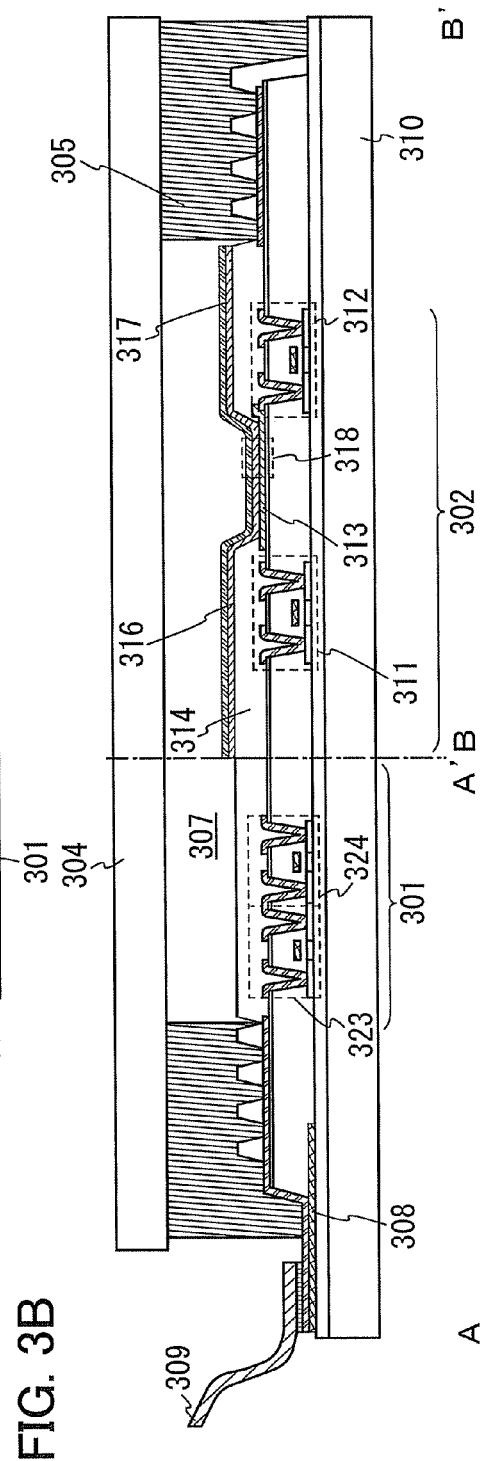

In FIG. 3A, reference numeral 301 denotes a driver circuit portion (a source driver circuit), reference numeral 302 denotes a pixel portion, and reference numeral 303 denotes a driver circuit portion (a gate driver circuit), which are each indicated by dotted lines. Reference numeral 304 denotes a sealing substrate, reference numeral 305 denotes a sealing material, and a portion enclosed by the sealing material 305 is a space 307.

Note that a lead wiring 308 is a wiring for transmitting signals that are to be input to the source driver circuit 301 and the gate driver circuit 303, and receives a video signal, a clock signal, a start signal, a reset signal, and the like from an FPC (flexible printed circuit) 309 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Next, a cross-sectional structure will be described with reference to FIG. 3B. The driver circuit portion and the pixel portion are formed over an element substrate 310. Here, the source driver circuit 301 which is the driver circuit portion and one pixel in the pixel portion 302 are illustrated. Note that, in the source driver circuit 301, a CMOS circuit which includes an n-channel TFT 323 and a p-channel TFT 324 is formed. The driver circuit may be any of a variety of circuits formed with TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 302 includes a plurality of pixels having a switching TFT 311, a current control TFT 312, and a first electrode 313 electrically connected to a drain of the current control TFT 312. Note that an insulator 314 is formed to cover an end portion of the first electrode 313.

In order to improve coverage, the insulator 314 is preferably formed so as to have a curved surface with curvature at an upper end portion or a lower end portion. For example, when positive photosensitive acrylic is used as a material for the insulator 314, only an upper end portion of the insulator 314 can have a curved surface with a radius of curvature (0.2 μm to 3 μm). For the insulator 314, it is also possible to use either a negative type that becomes insoluble in an etchant by light irradiation or a positive type that becomes soluble in an etchant by light irradiation.

An EL layer 316 and a second electrode 317 are formed over the first electrode 313. Here, as a material for forming the first electrode 313, a material having a high work function is preferably used. For example, it is possible to use a single layer of an ITO film, an indium tin oxide film that includes silicon, an indium oxide film that includes zinc oxide at 2 wt % to 20 wt %, a titanium nitride film, a chromium film, a tungsten film, a Zn film, a Pt film, or the like, a stacked layer of a titanium nitride film and a film that mainly includes aluminum, a three-layer structure of a titanium nitride film, a film that mainly includes aluminum, and a titanium nitride film, or the like. Note that when a stacked layer structure is employed, resistance of a wiring is low and a favorable ohmic contact is obtained.

In addition, the EL layer 316 is formed by any of various methods such as an evaporation method using an evaporation mask, a droplet discharging method like an ink-jet method, a printing method, and a spin coating method. The EL layer 316 includes any of the oxadiazole derivatives described in Embodiment 1. Further, another material included in the EL layer 316 may be a low molecular material, an oligomer, a dendrimer, a high molecular material, or the like.

As the second electrode 317, any of a variety of metals, alloys, and electrically conductive compounds, or a mixture thereof can be used. Among such materials, a metal, an alloy, an electrically conductive compound, a mixture thereof, or the like having a low work function (a work function of 3.8 eV or less) is preferably used when the second electrode 317 is used as a cathode. As an example, an element belonging to Group 1 or Group 2 in the periodic table, i.e., an alkali metal such as lithium (Li) or cesium (Cs), an alkaline earth metal such as magnesium (Mg), calcium (Ca), or strontium (Sr), or an alloy containing any of these (e.g., Mg—Ag or Al—Li), and the like can be given.

In order that light generated in the EL layer 316 be transmitted through the second electrode 317, a stack of a metal thin film having a reduced thickness and a transparent conductive film (e.g., indium oxide-tin oxide (ITO), indium oxide-tin oxide that includes silicon or silicon oxide, indium oxide-zinc oxide (IZO), or indium oxide that includes tungsten oxide and zinc oxide) can be used for the second electrode 317.

Further, the sealing substrate 304 is attached to the element substrate 310 with the sealing material 305, so that a light-emitting element 318 is provided in the space 307 enclosed by the element substrate 310, the sealing substrate 304, and the sealing material 305. The space 307 is filled with a filler, and may be filled with an inert gas (such as nitrogen or argon) or the sealing material 305.

Note that an epoxy-based resin is preferably used as the sealing material 305. Such a material preferably allows as little moisture and oxygen as possible to penetrate. As a material used for the sealing substrate 304, a plastic substrate formed of FRP (fiberglass-reinforced plastics), PVF (polyvinyl fluoride), polyester, acrylic, or the like can be used besides a glass substrate or a quartz substrate.

As described above, the active matrix light-emitting device having the light-emitting element which is one embodiment of the present invention can be obtained.

Figure 4A:
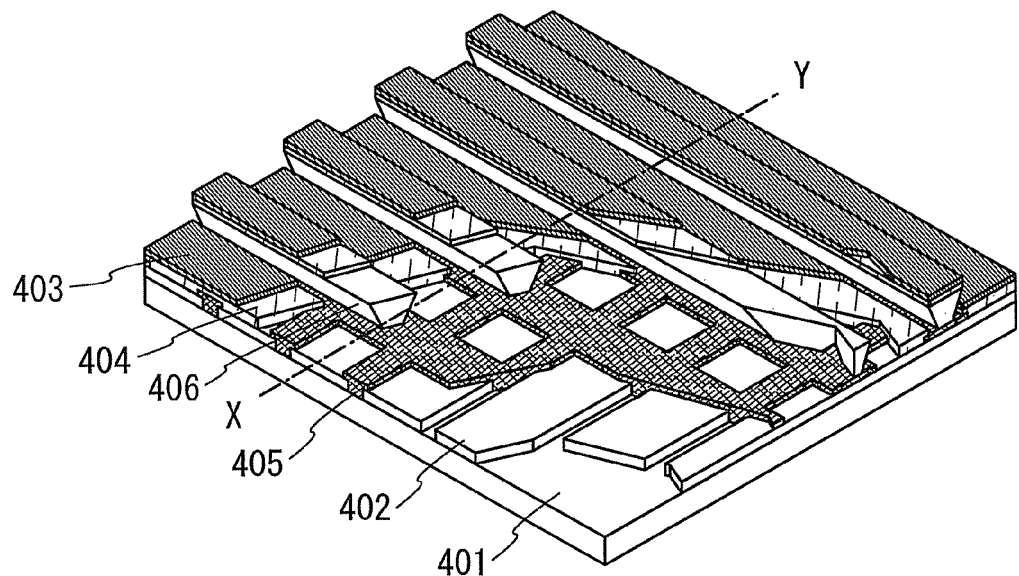
FIGS. 4A and 4B illustrate a light-emitting device of one embodiment of the present invention.
Figure 4B:
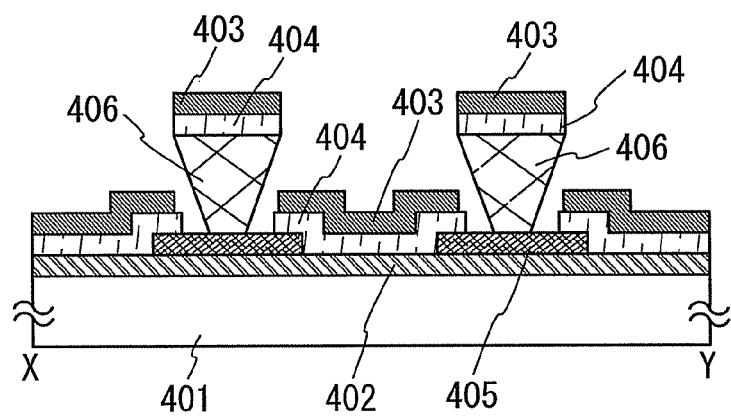

Further, a light-emitting element of one embodiment of the present invention can be used for a passive matrix light-emitting device as well as the above active matrix light-emitting device. FIGS. 4A and 4B are a perspective view and a cross-sectional view of a passive matrix light-emitting device using a light-emitting element of one embodiment of the present invention. Note that FIG. 4A is a perspective view of the light-emitting device, and FIG. 4B is a cross-sectional view taken along line X-Y of FIG. 4A.

In FIGS. 4A and 4B, an EL layer 404 is provided between a first electrode 402 and a second electrode 403 over a substrate 401. An end portion of the first electrode 402 is covered with an insulating layer 405. In addition, a partition layer 406 is provided over the insulating layer 405. The sidewalls of the partition layer 406 are aslope so that a distance between both the sidewalls is gradually narrowed toward the surface of the substrate. In other words, a cross section taken along the direction of the short side of the partition layer 406 is trapezoidal, and the base (side facing in a direction similar to a plane direction of the insulating layer 405 and being in contact with the insulating layer 405) is shorter than the upper side (side facing in the direction similar to the plane direction of the insulating layer 405 and not being in contact with the insulating layer 405). By providing the partition layer 406 in such a way, a defect of a light-emitting element due to static electricity or the like can be prevented.

Thus, the passive matrix light-emitting device having a light-emitting element which is one embodiment of the present invention can be obtained.

The light-emitting devices described in this embodiment (the active matrix light-emitting device and the passive matrix light-emitting device) are both formed using the light-emitting element which is one embodiment of the present invention, and accordingly, the light-emitting devices can have low power consumption.

Note that this embodiment can be combined with any of the structures described in the other embodiments as appropriate.

Embodiment 5

In this embodiment, with reference to FIGS. 5A to 5E, FIG. 6, and FIG. 7, description is given of examples of a variety of electronic devices and lighting devices that are completed by using a light-emitting device which is one embodiment of the present invention.

Examples of the electronic devices to which the light-emitting device is applied are television devices (also referred to as televisions or television receivers), monitors for computers and the like, cameras such as digital cameras and digital video cameras, digital photo frames, mobile phones (also referred to as cellular phones or cellular phone devices), portable game machines, portable information terminals, audio reproducing devices, large game machines such as pachinko machines, and the like. Specific examples of these electronic devices and a lighting device are illustrated in FIGS. 5A to 5E.

Figure 5A:
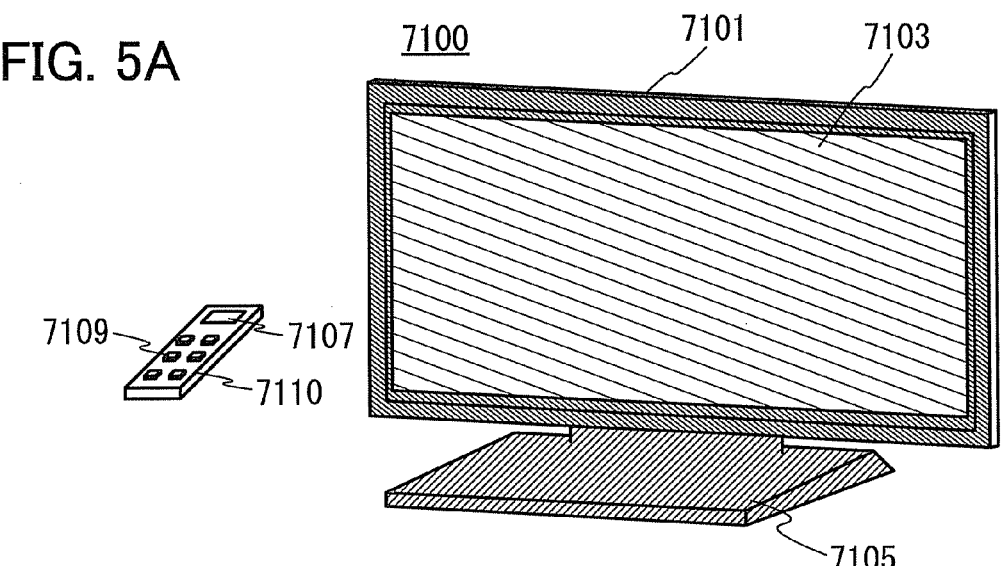
FIGS. 5A to 5E illustrate electronic devices and a lighting device of embodiments of the present invention.

FIG. 5A illustrates an example of a television device. In a television device 7100, a display portion 7103 is incorporated into a housing 7101. The display portion 7103 is capable of displaying images, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Further, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 5B:
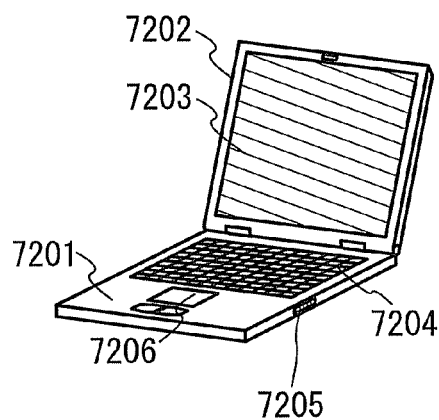

FIG. 5B illustrates a computer having a main body 7201, a housing 7202, a display portion 7203, a keyboard 7204, an external connection port 7205, a pointing device 7206, and the like. This computer is manufactured by using a light-emitting device for the display portion 7203.

Figure 5C:
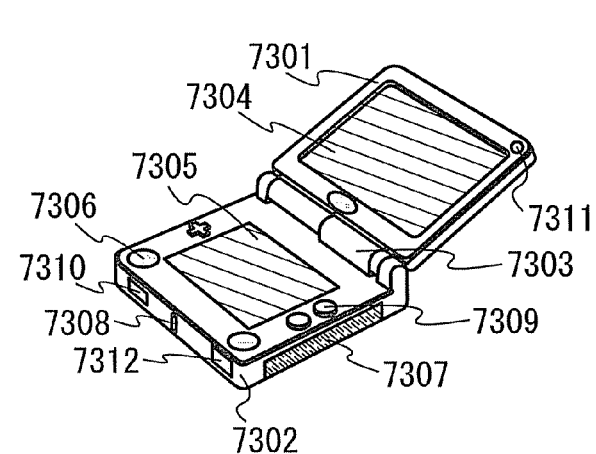

FIG. 5C illustrates a portable game machine having two housings, a housing 7301 and a housing 7302, which are connected with a joint portion 7303 so that the portable game machine can be opened or folded. A display portion 7304 is incorporated into the housing 7301 and a display portion 7305 is incorporated into the housing 7302. In addition, the portable game machine illustrated in FIG. 5C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable game machine is not limited to the above as far as a light-emitting device can be used for at least either the display portion 7304 or the display portion 7305, or both, and may include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above.

Figure 5D:
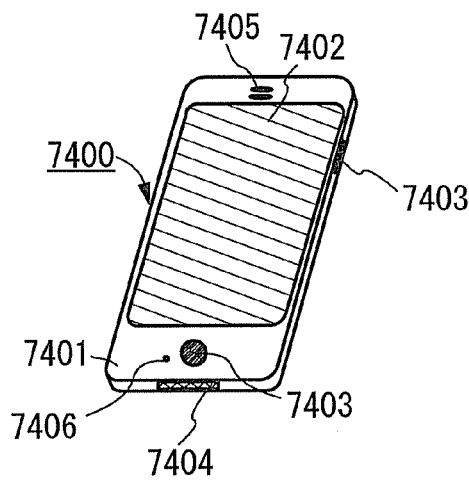

FIG. 5D illustrates an example of a cellular phone. A cellular phone 7400 is provided with operation buttons 7403, an external connection port 7404, a speaker 7405, a microphone 7406, and the like, in addition to a display portion 7402 incorporated into a housing 7401. Note that the cellular phone 7400 is manufactured using a light-emitting device for the display portion 7402.

When the display portion 7402 of the cellular phone 7400 illustrated in FIG. 5D is touched with a finger or the like, data can be input into the cellular phone 7400. Further, operations such as making a call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a text input mode mainly for inputting text is selected for the display portion 7402 so that text displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or operation with the operation buttons 7403 of the housing 7401. Alternatively, the screen modes can be switched depending on kinds of images displayed on the display portion 7402. For example, when a signal for an image displayed on the display portion is data of moving images, the screen mode is switched to the display mode. When the signal is text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 can function as an image sensor. For example, an image of a palm print, a fingerprint, or the like is taken by touch on the display portion 7402 with the palm or the finger, so that personal authentication can be performed. Furthermore, by provision of a backlight or a sensing light source emitting a near-infrared light in the display portion, an image of a finger vein, a palm vein, or the like can also be taken.

Figure 5E:
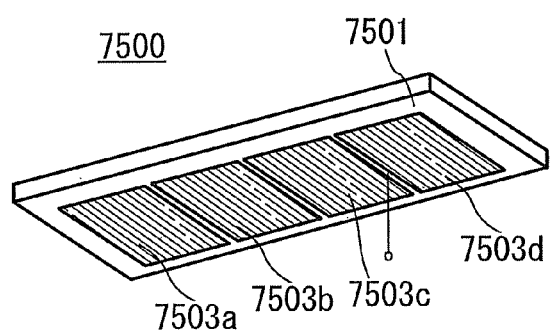

FIG. 5E illustrates an example of a lighting device. In a lighting device 7500, light-emitting devices 7503*a* to 7503*d* of one embodiment of the present invention are incorporated in a housing 7501 as light sources. The lighting device 7500 can be attached to a ceiling, a wall, or the like.

The light-emitting device of one embodiment of the present invention includes a light-emitting element in a thin film form. Thus, when the light-emitting device is attached to a base with a curved surface, the light-emitting device with a curved surface can be obtained. In addition, when the light-emitting device is located in a housing with a curved surface, an electronic device or a lighting device with a curved surface can be obtained.

Figure 6:
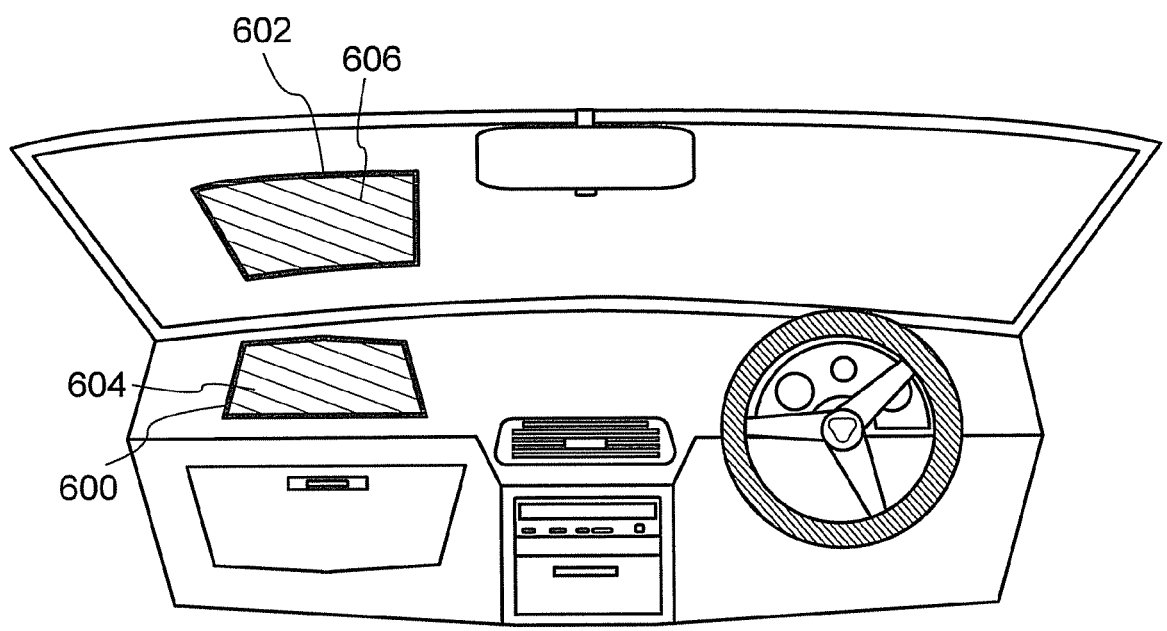
FIG. 6 illustrates electronic devices of embodiments of the present invention.

FIG. 6 illustrates a driver's seat and the periphery thereof inside a vehicle. FIG. 6 illustrates an example in which a display device 600 is set on a dashboard and a display device 602 is set on a windshield. In the display device 600 illustrated in FIG. 6, a display portion 604 is incorporated in a housing with a curved surface and can display images. In the display device 600, the light-emitting device of one embodiment of the present invention can be used in the display portion 604.

In the display device 602 illustrated in FIG. 6, a display portion 606 is incorporated in a housing with a curved surface and the light-emitting device of one embodiment of the present invention can be used in the display portion 606. A pair of electrodes and a support of a light-emitting element which are included in the light-emitting device of one embodiment of the present invention are formed using a light-transmitting material, whereby light can be extracted through both a top surface and a bottom surface of the light-emitting device. Thus, the light-emitting device is used in the display portion 606, whereby a user can see the outside from the display portion 606 through the windshield. Similarly, a user can also see an image displayed on the display portion 606 from the outside through the windshield.

Note that the display device 600 or the display device 602 illustrated in FIG. 6 can also be used as a lighting device.

Figure 7:
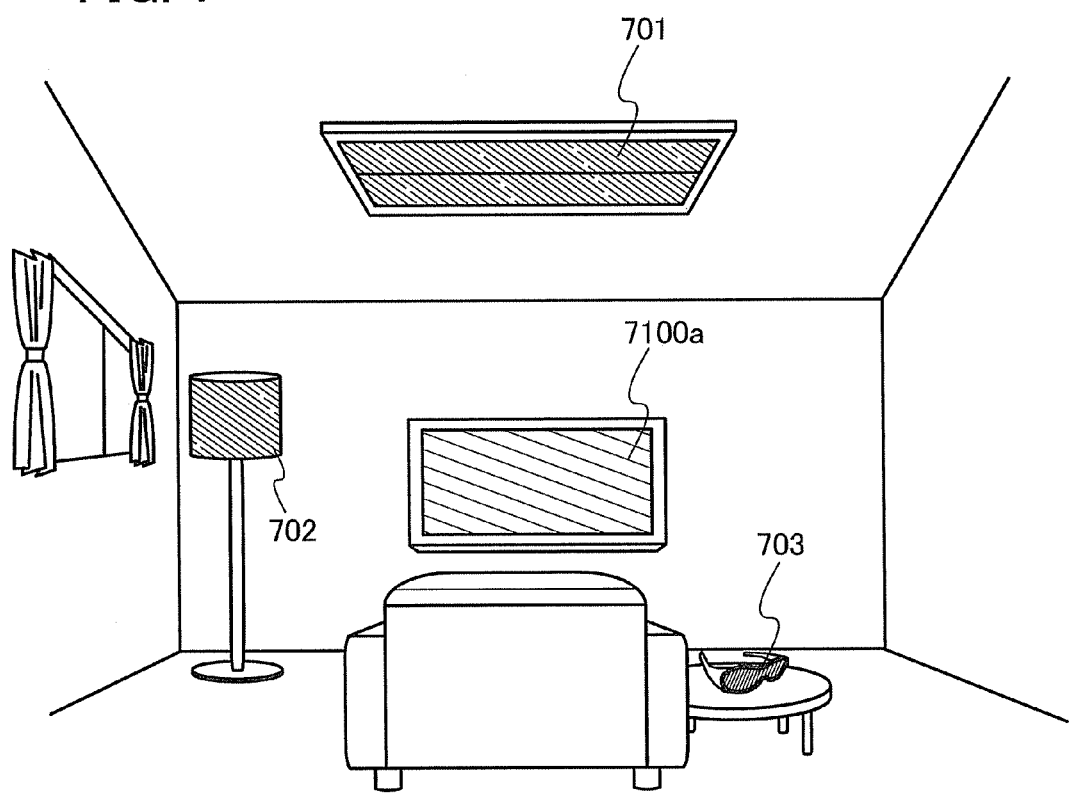
FIG. 7 illustrates electronic devices and lighting devices of embodiments of the present invention.

FIG. 7 illustrates an example in which the light-emitting device is used as an indoor lighting device 701. Since the area of the light-emitting device can be increased, the light-emitting device can be used as a lighting device with a large area.

In addition, a lighting device 702 in which a light-emitting region has a curved surface can also be obtained with the use of a housing with a curved surface. A light-emitting element included in the lighting device described in this embodiment is in a thin film form, which allows the housing to be designed more freely. Therefore, the lighting device can be elaborately designed in a variety of ways.

A television device 7100*a* that is a television device one example of which is illustrated in FIG. 5A can be set in a room provided with the lighting device to which one embodiment of the present invention is applied. The television device 7100*a* may have a three-dimensional display function as well as a normal two-dimensional display function. In FIG. 7, a three-dimensional image can be watched with glasses 703 for watching three-dimensional images.

As described above, the electronic devices and the lighting devices can be obtained by application of the light-emitting device. The light-emitting device has a remarkably wide application range, and thus can be applied to electronic devices in a variety of fields.

Note that the structure described in this embodiment can be combined with any of the structures described in Embodiments 1 to 4 as appropriate.

Example 1

In Example 1, a method of synthesizing 2-[4-dibenzothiophen-4-yl)phenyl]-5-phenyl-1,3,4-oxadiazole (abbreviation: DBTO11-II) represented by Structural Formula (100) in Embodiment 1 is specifically described.

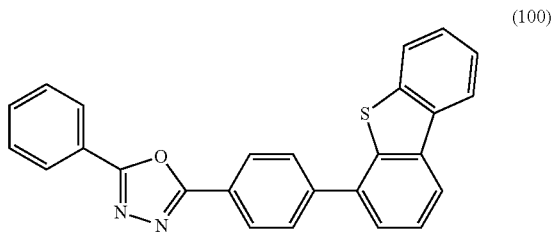 [SMILES: c1ccc(-c2nnc(-c3ccc(-c4cccc5c4sc4ccccc45)cc3)o2)cc1]
(100)

Synthesis of 2-[4-dibenzothiophen-4-yl)phenyl]-5-phenyl-1,3,4-oxadiazole (abbreviation: DBTO11-II)

A synthesis scheme of 2-[4-dibenzothiophen-4-yl)phenyl]-5-phenyl-1,3,4-oxadiazole (abbreviation: DBTO11-II) is illustrated in (B-1).

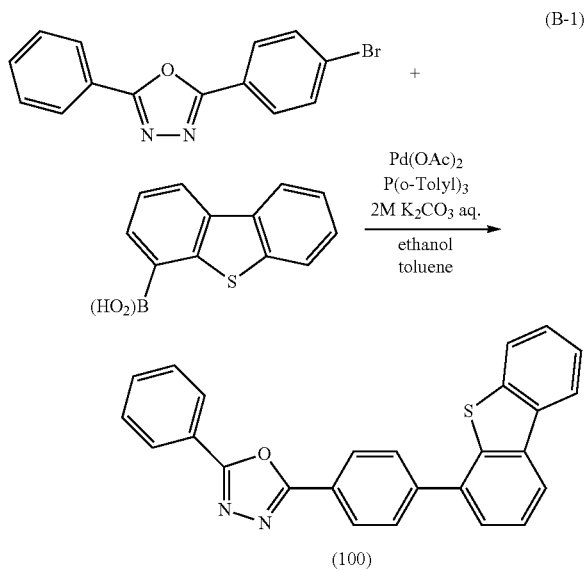
(B-1)

Into a 50-mL three neck flask were put 1.1 g (3.7 mmol) of 2-(4-bromophenyl)-5-phenyl-1,3,4-oxadiazole, 0.9 g (3.9 mmol) of dibenzothiophene-4-boronic acid, and 56 mg (0.2 mmol) of tris(2-methylphenyl)phosphine, and the air in the flask was replaced with nitrogen. To this mixture were added 3.7 mL of a 2.0M aqueous potassium carbonate solution, 15 mL of toluene, and 5 mL of ethanol, and the mixture was degassed by being stirred under reduced pressure.

To this mixture was added 8.3 mg (37 μmol) of palladium (II) acetate, and the mixture was stirred at 80° C. for 7 hours under a nitrogen stream. After a predetermined time, the aqueous layer of the obtained mixture was extracted with toluene. The obtained extract solution and the organic layer were combined, washed with saturated brine, and dried over magnesium sulfate. This mixture was separated by gravity filtration, and the filtrate was concentrated to give a solid. This solid was purified by silica gel column chromatography.

The column chromatography was performed first using toluene as a developing solvent and then using a mixed solvent of a 20:1 ratio of toluene to ethyl acetate as a developing solvent. The obtained fraction was condensed to give a solid. This solid was purified by high performance liquid column chromatography. The high performance liquid column chromatography was performed using chloroform as a developing solvent. The obtained fraction was condensed to give a solid. Hexane was added to this solid, followed by irradiation with ultrasonic waves. The solid was collected by suction filtration, so that 1.3 g of a white powder was obtained in 88% yield, which was the substance to be produced.

By a train sublimation method, 1.3 g of the obtained white powder was purified. The purification was performed under the following conditions: the temperature was 220° C.; the pressure was 2.5 Pa; and the flow rate of argon gas was 5 mL/min. Accordingly, 1.1 g of the compound was obtained at a yield of 85%.

In addition, the compound obtained through the above synthesis method was measured by a nuclear magnetic resonance (NMR) method. The measurement data are shown below. $^1$H NMR (CDCl$_3$, 300 MHz): δ (ppm)=7.46-7.63 (m, 7H), 7.84-7.89 (m, 1H), 7.94 (d, J=8.4 Hz, 2H), 8.16-8.24 (m, 4H), 8.31 (d, J=8.4 Hz, 2H).

Figure 9A:
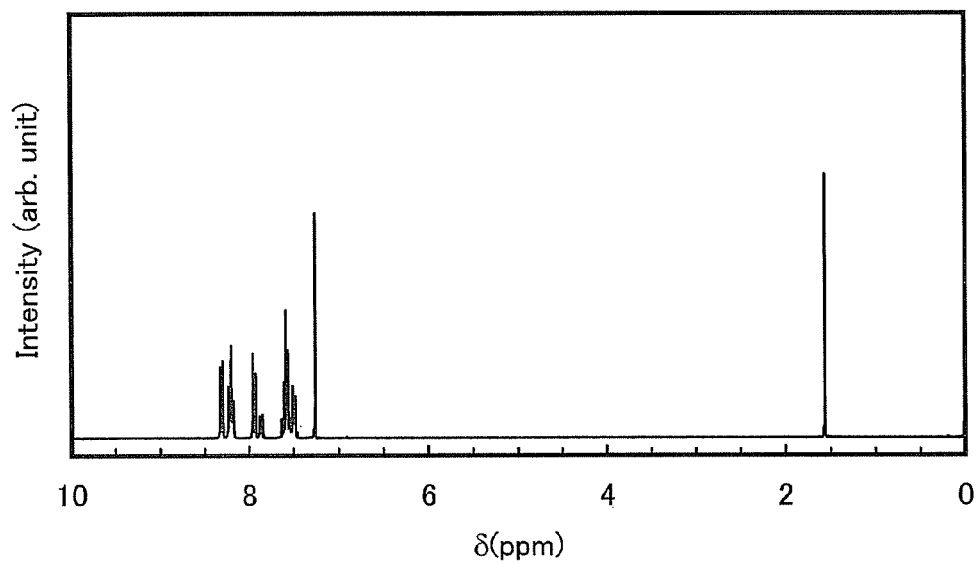
FIGS. 9A and 9B are NMR charts of DBTO11-II (abbreviation).
Figure 9B:
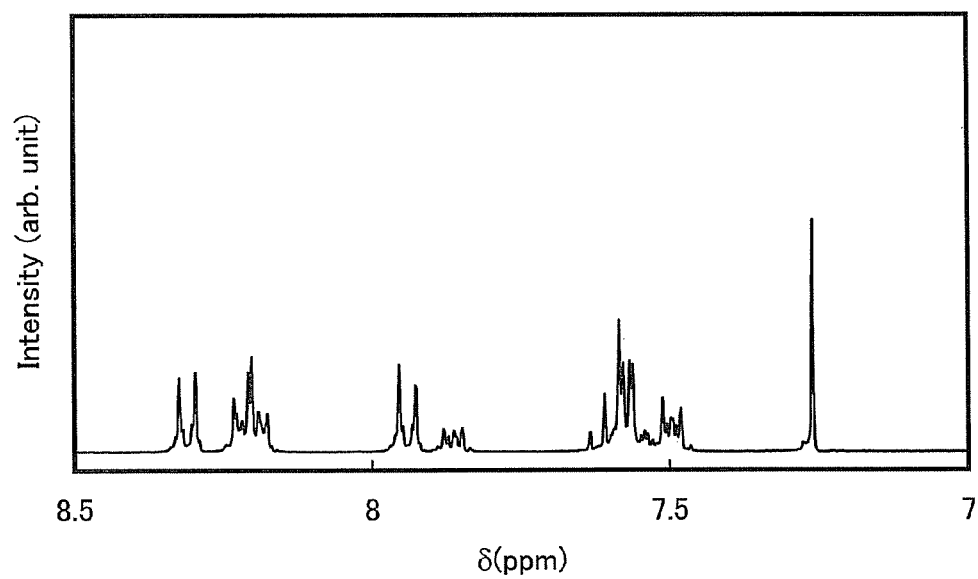

Further, $^1$H NMR charts are shown in FIGS. 9A and 9B. Note that FIG. 9B is a chart where the range of 7.0 ppm to 8.5 ppm in FIG. 9A is enlarged. It was found from the measurement results that 2-[4-dibenzothiophen-4-yl)phenyl]-5-phenyl-1,3,4-oxadiazole (abbreviation: DBTO11-II) represented by Structural Formula (100) above was obtained.

Figure 10A:
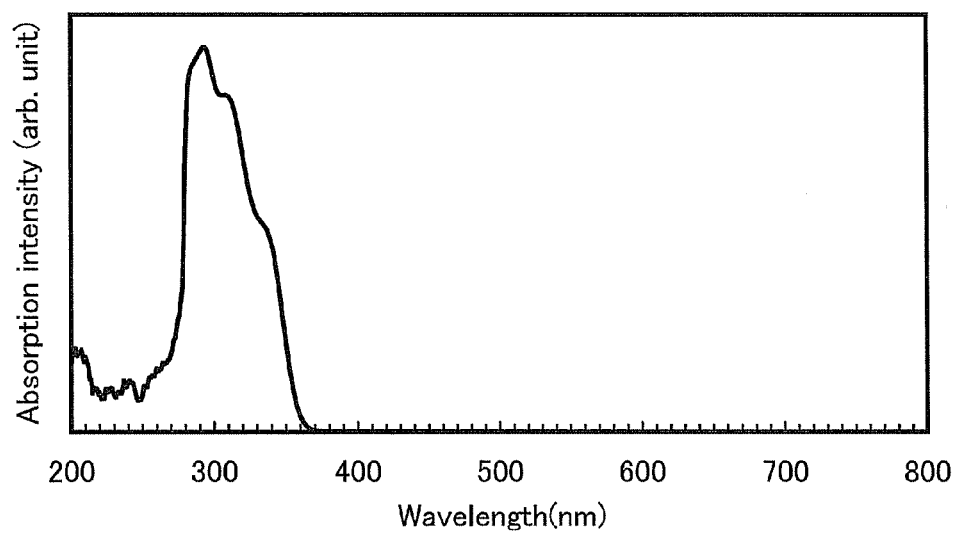
FIGS. 10A and 10B each show an absorption spectrum of DBTO11-II (abbreviation).
Figure 10B:
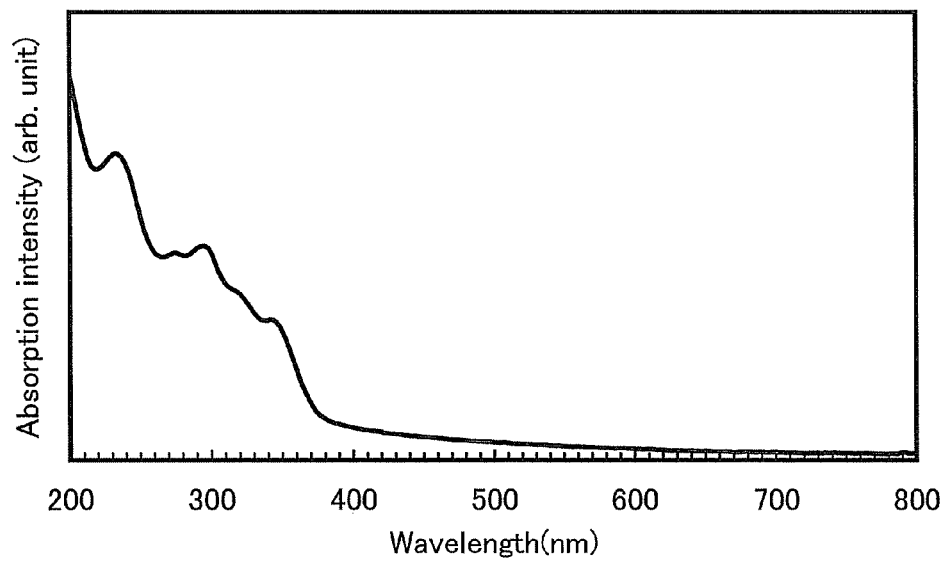

Further, FIG. 10A shows an absorption spectrum of DBTO11-II (abbreviation) in a toluene solution, and FIG. 10B shows an absorption spectrum of DBTO11-II (abbreviation) in a thin film. An ultraviolet-visible spectrophotometer (V-550, manufactured by JASCO Corporation) was used for the measurement. The absorption spectrum of DBTO11-II (abbreviation) in the toluene solution was obtained by subtracting the absorption spectra of quartz and toluene from the absorption spectrum of DBTO11-II (abbreviation) in the toluene solution in a quartz cell. In addition, the absorption spectrum of DBTO11-II (abbreviation) in the thin film was obtained by subtracting the absorption spectrum of quartz from the absorption spectrum of a sample formed by evaporating DBTO11-II (abbreviation) to a quartz substrate. In FIG. 10A and FIG. 10B, the horizontal axis represents wavelength (nm) and the vertical axis represents absorption intensity (arbitrary unit). In the case of the toluene solution, absorption peaks were observed at around 333 nm, 308 nm, and 292 nm, and in the case of the thin film, absorption peaks were observed at around 343 nm, 318 nm, 295 nm, 276 nm, and 233 nm.

Figure 11A:
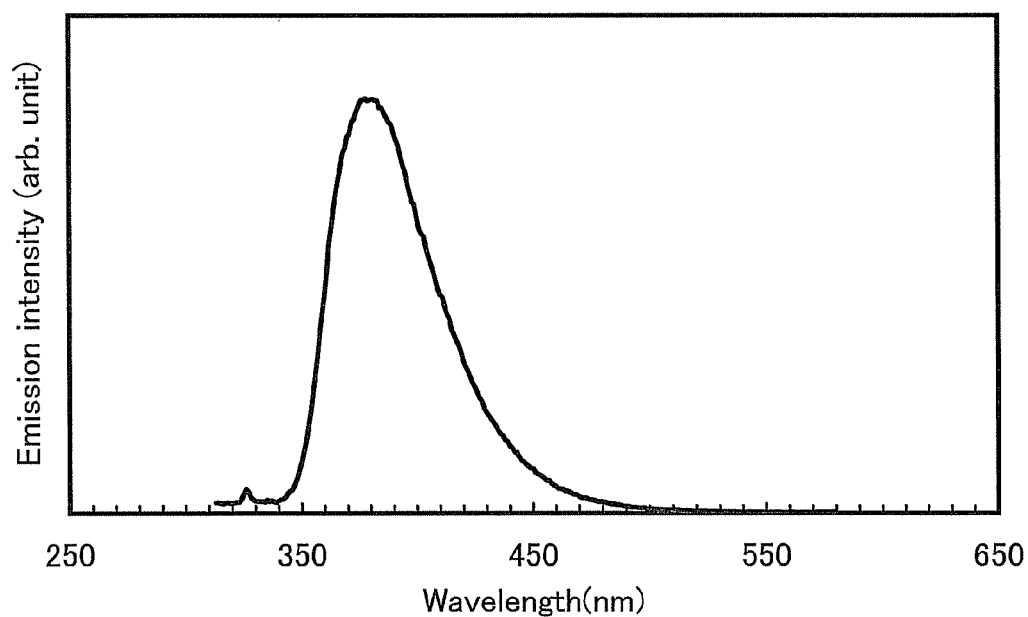
FIGS. 11A and 11B each show an emission spectrum of DBTO11-II (abbreviation).
Figure 11B:
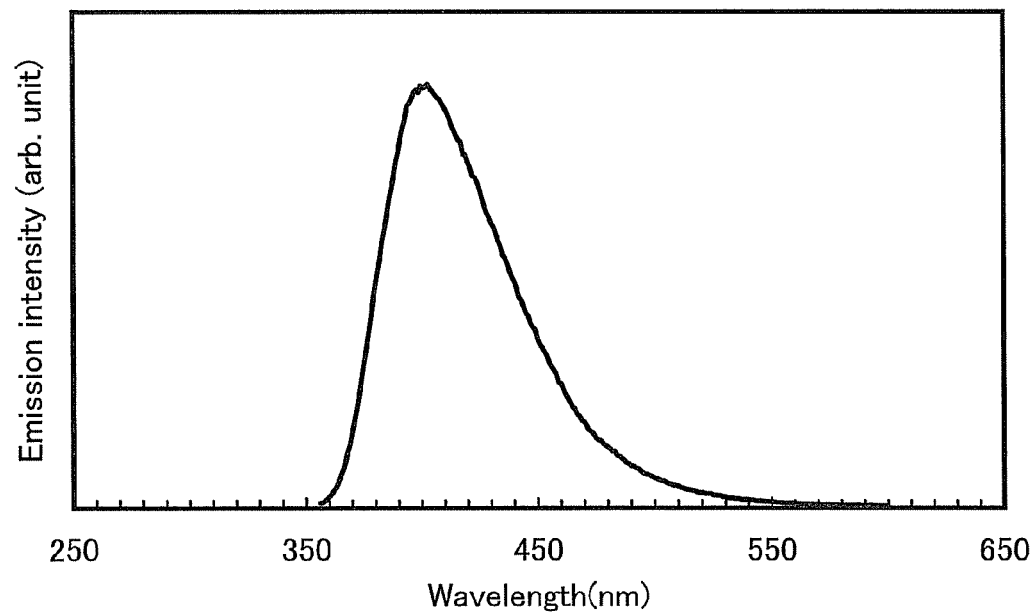

Further, FIG. 11A shows an emission spectrum of DBTO11-II (abbreviation) in the toluene solution (excitation wavelength: 297 nm). FIG. 11B shows an emission spectrum of DBTO11-II (abbreviation) in the thin film (excitation wavelength: 340 nm). In FIGS. 11A and 11B, the horizontal axis represents wavelength (nm) and the vertical axis represents emission intensity (arbitrary unit). The maximum emission wavelength was 380 nm in the case of the toluene solution (excitation wavelength: 297 nm), and 402 nm in the case of the thin film (excitation wavelength: 340 nm).

Further, by measurement with a photoelectron spectrometer (AC-2, manufactured by Riken Keiki, Co., Ltd.) in the atmosphere, the ionization potential of DBTO11-II (abbreviation) in the thin film was found to be 5.91 eV. As a result, the HOMO level was found to be −5.91 eV. Furthermore, with the use of the absorption spectrum data of DBTO11-II (abbreviation) in the thin film, the absorption edge was obtained by a Tauc plot assuming direct transition. The absorption edge was estimated as an optical energy gap, whereby the energy gap was 3.36 eV. From the obtained value of the energy gap and the HOMO level, the LUMO level was −2.55 eV.

Example 2

In Example 2, a method of synthesizing 2-[3-dibenzothiophen-4-yl)phenyl]-5-phenyl-1,3,4-oxadiazole (abbreviation: mDBTO11-II) represented by Structural Formula (101) in Embodiment 1 is specifically described.

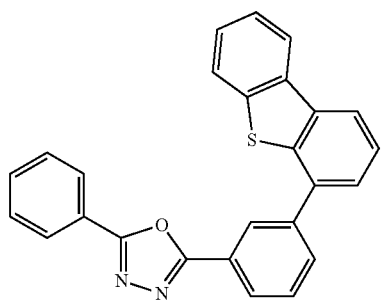

(101)

Synthesis of 2-[3-dibenzothiophen-4-yl)phenyl]-5-phenyl-1,3,4-oxadiazole (abbreviation: mDBTO11-II)

A synthesis scheme of 2-[3-dibenzothiophen-4-yl)phenyl]-5-phenyl-1,3,4-oxadiazole (abbreviation: mDBTO11-II) is illustrated in (C-1).

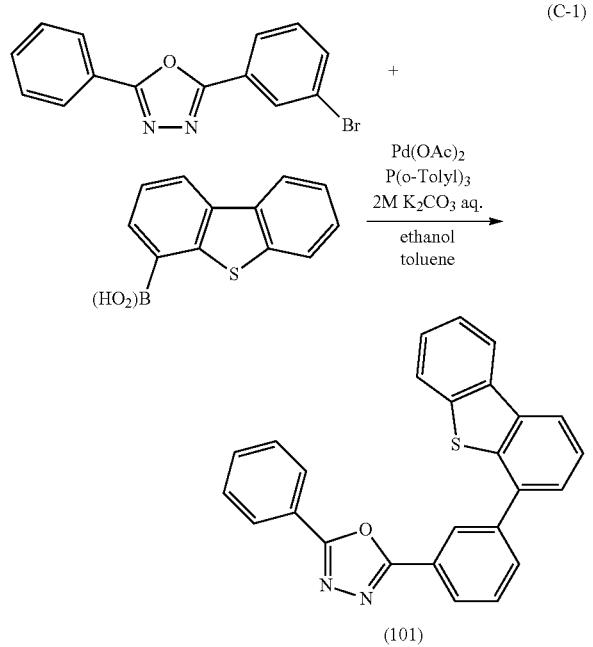

Into a 50-mL three neck flask were put 1.1 g (3.7 mmol) of 2-(3-bromophenyl)-5-phenyl-1,3,4-oxadiazole, 0.9 g (3.9 mmol) of dibenzothiophene-4-boronic acid, and 56 mg (0.2 mmol) of tris(2-methylphenyl)phosphine, and the air in the flask was replaced with nitrogen. To this mixture were added 3.7 mL of a 2.0M aqueous potassium carbonate solution, 15 mL of toluene, and 5.0 mL of ethanol, and the mixture was degassed by being stirred under reduced pressure.

To this mixture was added 8.3 mg (37 μmol) of palladium (II) acetate, and the mixture was stirred at 80° C. for 7 hours under a nitrogen stream. After a predetermined time, the aqueous layer of the obtained mixture was extracted with toluene. The obtained extract solution and the organic layer were combined, washed with saturated brine, and dried over magnesium sulfate. This mixture was separated by gravity filtration, and the filtrate was concentrated to give a solid. This solid was purified by silica gel column chromatography.

The column chromatography was performed first using toluene as a developing solvent and then using a mixed solvent of a 20:1 ratio of toluene to ethyl acetate as a developing solvent. The obtained fraction was condensed to give a solid. Methanol was added to this solid, followed by irradiation with ultrasonic waves. The solid was collected by suction filtration, so that 1.3 g of a white powder was obtained in 91% yield, which was the substance to be produced.

By a train sublimation method, 1.3 g of the obtained white powder was purified. The purification was performed under the following conditions: the temperature was 230° C.; the pressure was 2.4 Pa; and the flow rate of argon gas was 5 ml/min. Accordingly, 1.1 g of the compound was obtained at a yield of 85%.

In addition, the compound obtained through the above synthesis method was measured by a nuclear magnetic resonance (NMR) method. The measurement data are shown below. $^1$H NMR (CDCl$_3$, 300 MHz): δ (ppm)=7.46-7.64 (m, 7H), 7.71 (t, J=7.8 Hz, 1H), 7.84-7.87 (m, 1H), 7.94-7.98 (m, 1H), 8.15-8.26 (m, 5H), 8.50-8.51 (m, 1H).

Figure 12A:
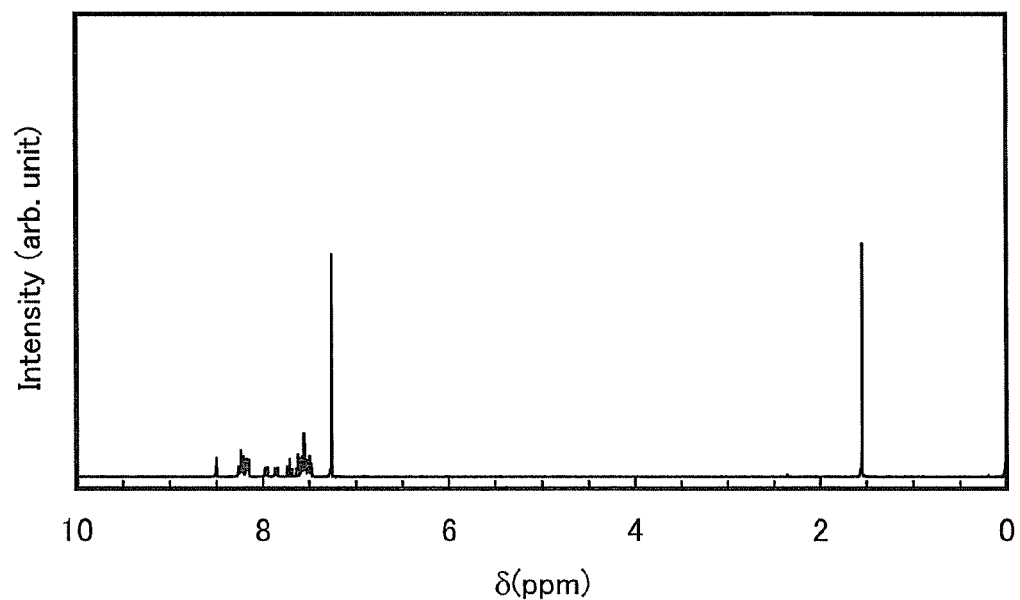
FIGS. 12A and 12B are NMR charts of mDBTO11-II (abbreviation).
Figure 12B:
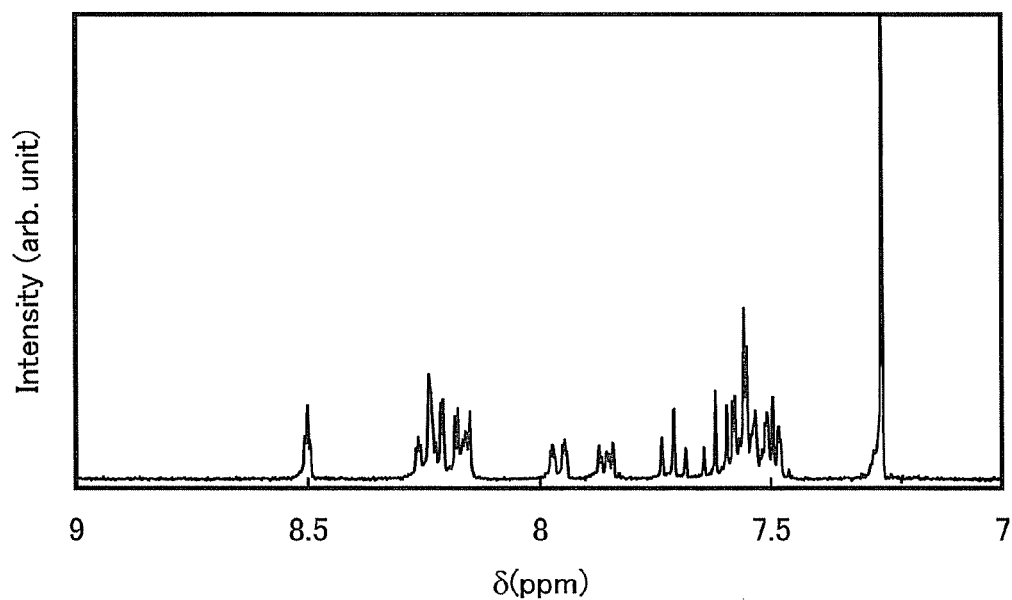

Further, $^1$H NMR charts are shown in FIGS. 12A and 12B. Note that FIG. 12B is a chart where the range of 7.0 ppm to 9.0 ppm in FIG. 12A is enlarged. It was found from the measurement results that 2-[3-dibenzothiophen-4-yl)phenyl]-5-phenyl-1,3,4-oxadiazole (abbreviation: mDBTO11-II) represented by Structural Formula (101) above was obtained.

Figure 13A:
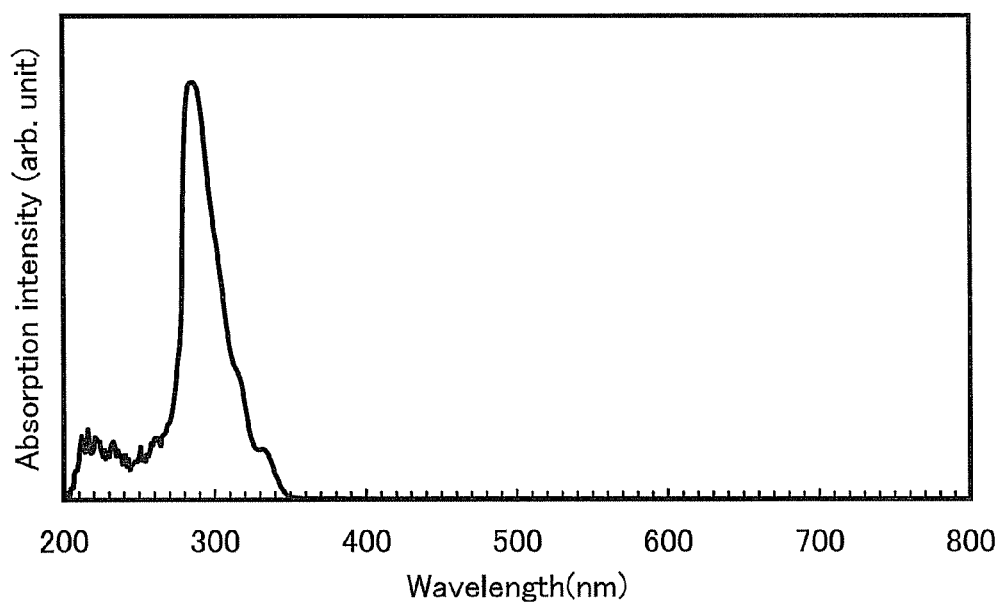
FIGS. 13A and 13B each show an absorption spectrum of mDBTO11-II (abbreviation).
Figure 13B:
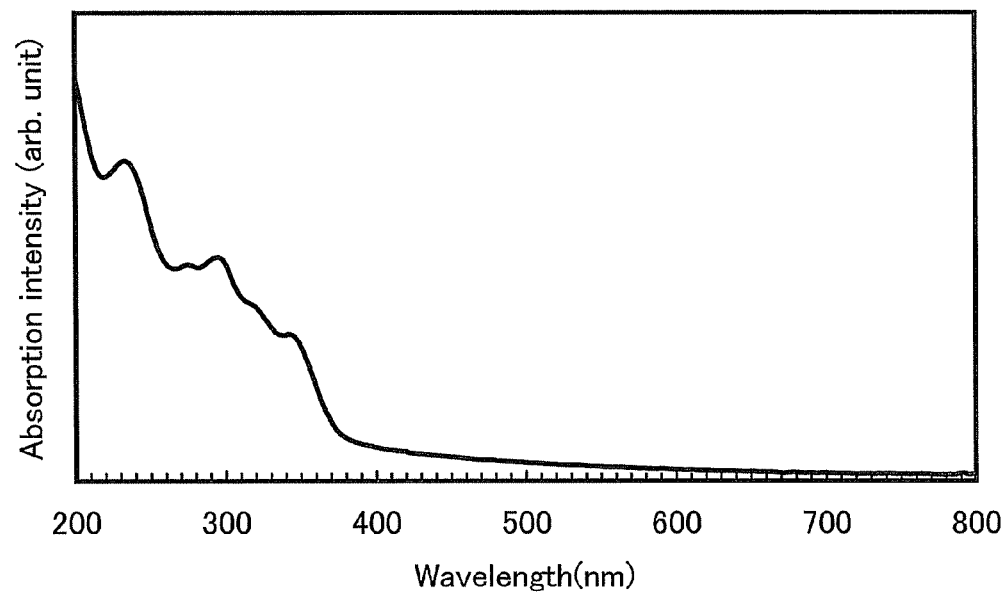

Further, FIG. 13A shows an absorption spectrum of mDBTO11-II (abbreviation) in a toluene solution, and FIG. 13B shows an absorption spectrum of mDBTO11-II (abbreviation) in a thin film. An ultraviolet-visible spectrophotometer (V-550, manufactured by JASCO Corporation) was used for the measurement. The absorption spectrum of mDBTO11-II (abbreviation) in the toluene solution was obtained by subtracting the absorption spectra of quartz and toluene from the absorption spectrum of mDBTO11-II (abbreviation) in the toluene solution in a quartz cell. In addition, the absorption spectrum of mDBTO11-II (abbreviation) in the thin film was obtained by subtracting the absorption spectrum of quartz from the absorption spectrum of a sample formed by evaporating mDBTO11-II (abbreviation) to a quartz substrate.

In FIG. 13A and FIG. 13B, the horizontal axis represents wavelength (nm) and the vertical axis represents absorption intensity (arbitrary unit). In the case of the toluene solution, absorption peaks were observed at around 333 nm, 316 nm, and 286 nm, and in the case of the thin film, absorption peaks were observed at around 338 nm, 319 nm, 287 nm, 271 nm, and 243 nm.

Figure 14A:
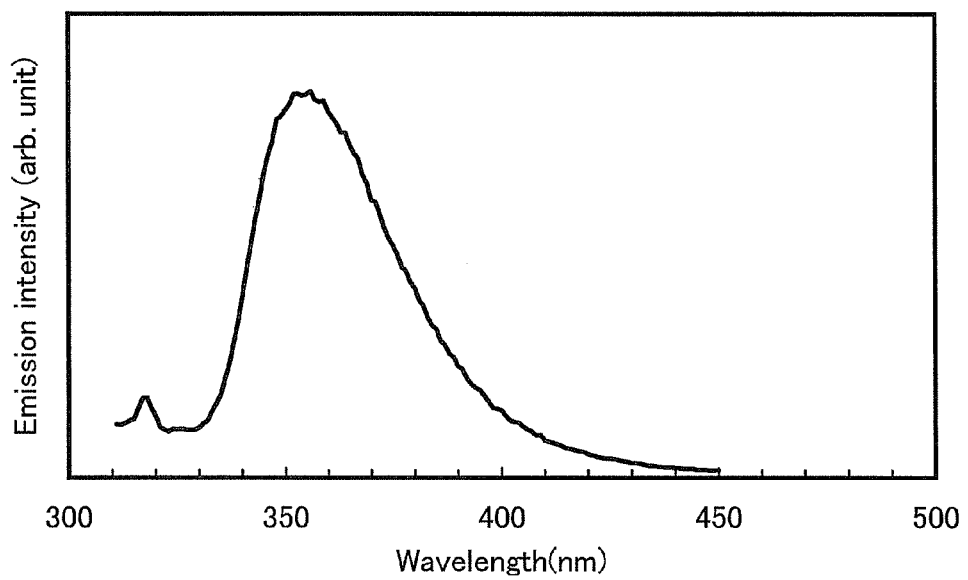
FIGS. 14A and 14B each show an emission spectrum of mDBTO11-II (abbreviation).
Figure 14B:
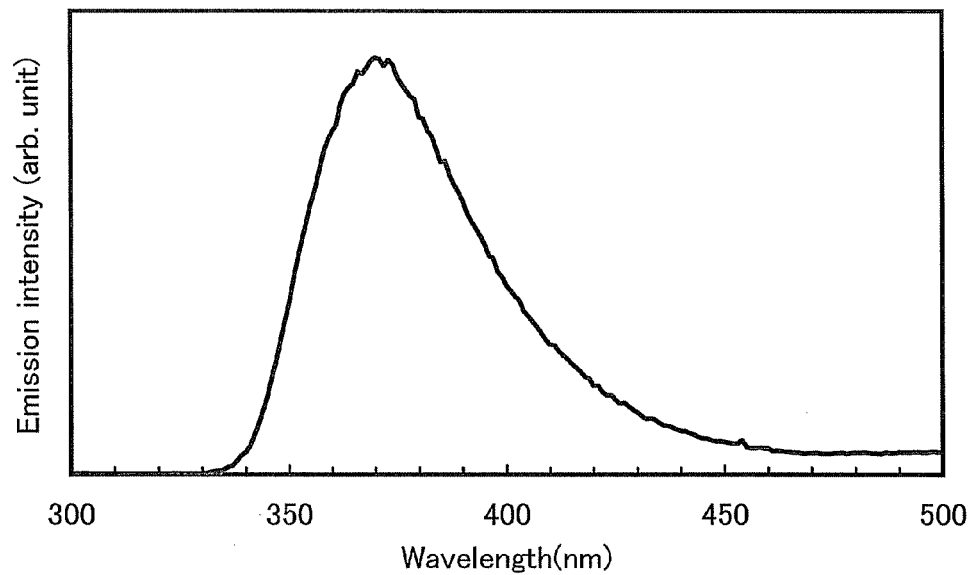

Further, FIG. 14A shows an emission spectrum of mDBTO11-II (abbreviation) in the toluene solution (excitation wavelength: 290 nm). FIG. 14B shows an emission spectrum of mDBTO11-II (abbreviation) in the thin film (excitation wavelength: 285 nm). In FIGS. 14A and 14B, the horizontal axis represents wavelength (nm) and the vertical axis represents emission intensity (arbitrary unit). The maximum emission wavelength was 355 nm in the case of the toluene solution (excitation wavelength: 290 nm), and 370 nm in the case of the thin film (excitation wavelength: 285 nm).

Further, by measurement with a photoelectron spectrometer (AC-2, manufactured by Riken Keiki, Co., Ltd.) in the atmosphere, the ionization potential of mDBTO11-II (abbreviation) in the thin film was found to be 5.63 eV. As a result, the HOMO level was found to be −5.63 eV. Furthermore, with the use of the absorption spectrum data of mDBTO11-II (abbreviation) in the thin film, the absorption edge was obtained by a Tauc plot assuming direct transition. The absorption edge was estimated as an optical energy gap, whereby the energy gap was 3.48 eV. From the obtained value of the energy gap and the HOMO level, the LUMO level was −2.15 eV.

Example 3

In Example 3, a method of synthesizing 2-[4-(2,8-diphenyldibenzothiophen-4-yl)phenyl]-5-phenyl-1,3,4-oxadiazole (abbreviation: DBTO11-III) represented by Structural Formula (128) in Embodiment 1 is specifically described.

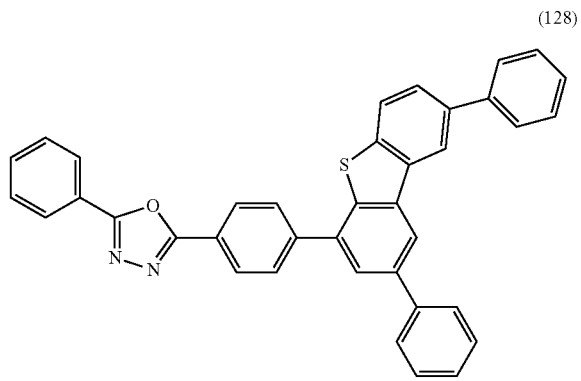 [SMILES: c1ccc(-c2ccc3sc4c(-c5ccc(-c6nnc(-c7ccccc7)o6)cc5)cc(-c5ccccc5)cc4c3c2)cc1]

(128)

Synthesis of 2-[4-(2,8-diphenyldibenzothiophen-4-yl)phenyl]-5-phenyl-1,3,4-oxadiazole (abbreviation: DBTO11-III)

A synthesis scheme of 2-[4-(2,8-diphenyldibenzothiophen-4-yl)phenyl]-5-phenyl-1,3,4-oxadiazole (abbreviation: DBTO11-III)] is illustrated in (D-1).

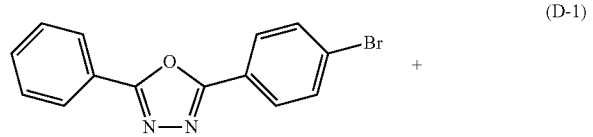

(D-1)

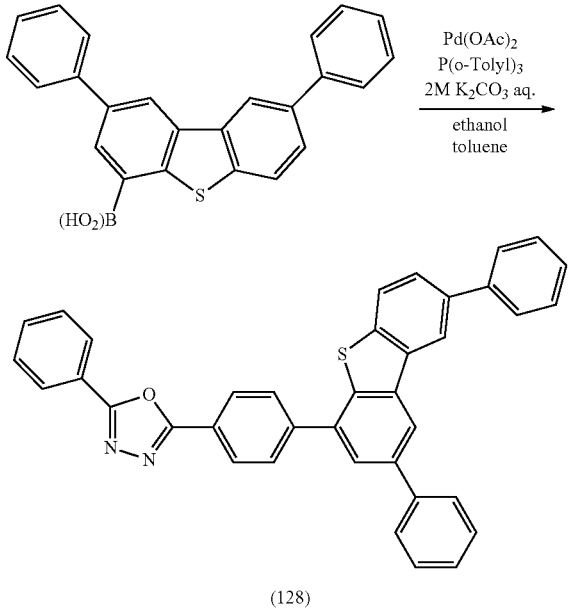

(128)

Into a 50-mL three neck flask were put 0.8 g (2.7 mmol) of 2-(4-bromophenyl)-5-phenyl-1,3,4-oxadiazole, 1.1 g (2.9 mmol) of 2,8-diphenyldibenzothiophene-4-boronic acid, and 41 mg (0.1 mmol) of tris(2-methylphenyl)phosphine, and the air in the flask was replaced with nitrogen. To this mixture were added 3.0 mL of a 2.0M aqueous potassium carbonate solution, 10 mL of toluene, and 3.4 mL of ethanol, and the mixture was degassed by being stirred under reduced pressure.

To this mixture was added 6.0 mg (27 μmol) of palladium (II) acetate, and the mixture was stirred at 80° C. for 7 hours under a nitrogen stream. After a predetermined time, the aqueous layer of the obtained mixture was extracted with chloroform. The obtained extract solution and the organic layer were combined, washed with saturated brine, and dried over magnesium sulfate. This mixture was separated by gravity filtration, and the filtrate was concentrated to give an oily substance. This oily substance was purified by silica gel column chromatography.

The column chromatography was performed using toluene as a developing solvent. The obtained fraction was condensed to give a solid. Methanol was added to this solid, followed by irradiation with ultrasonic waves. The solid was collected by suction filtration, so that 1.4 g of a white powder was obtained in 93% yield, which was the substance to be produced.

By a train sublimation method, 1.4 g of the obtained white powder was purified. The purification was performed under the following conditions: the temperature was 310° C.; the pressure was 2.4 Pa; and the flow rate of argon gas was 5 mL/min. Accordingly, 1.2 g of the compound was obtained at a yield of 86%.

In addition, the compound obtained through the above synthesis method was measured by a nuclear magnetic resonance (NMR) method. The measurement data are shown below. $^1$H NMR (CDCl$_3$, 300 MHz): δ (ppm)=7.38-7.45 (m, 2H), 7.49-7.59 (m, 7H), 7.73-7.80 (m, 6H), 7.92 (d, J=8.4 Hz, 1H), 7.99 (d, J=8.1 Hz, 2H), 8.16-8.21 (m, 2H), 8.33 (d, J=8.1 Hz, 2H), 8.45 (d, J=1.8 Hz, 2H).

Figure 15A:
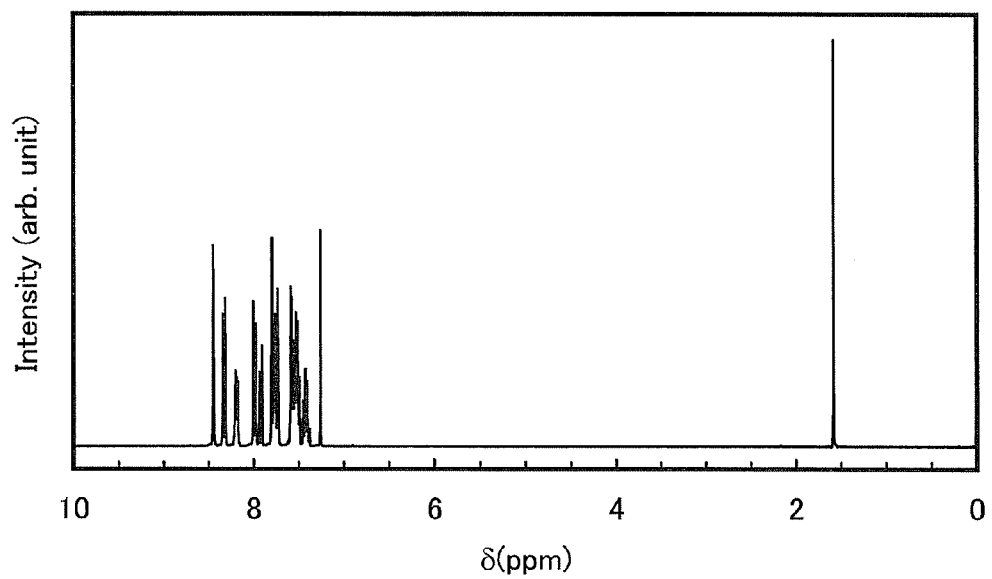
FIGS. 15A and 15B are NMR charts of DBTO11-III (abbreviation).
Figure 15B:
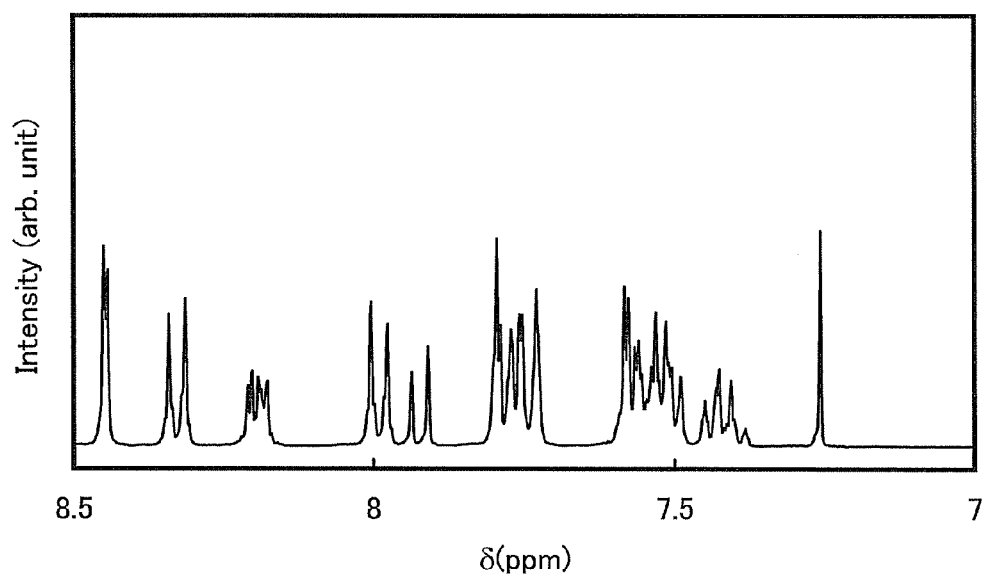

Further, $^1$H NMR charts are shown in FIGS. 15A and 15B. Note that FIG. 15B is a chart where the range of 7.0 ppm to 8.5 ppm in FIG. 15A is enlarged. It was found from the measurement results that 2-[4-(2,8-diphenyldibenzothiophen-4-yl)phenyl]-5-phenyl-1,3,4-oxadiazole (abbreviation: DBTO11-III) represented by Structural Formula (128) above was obtained.

Figure 16A:
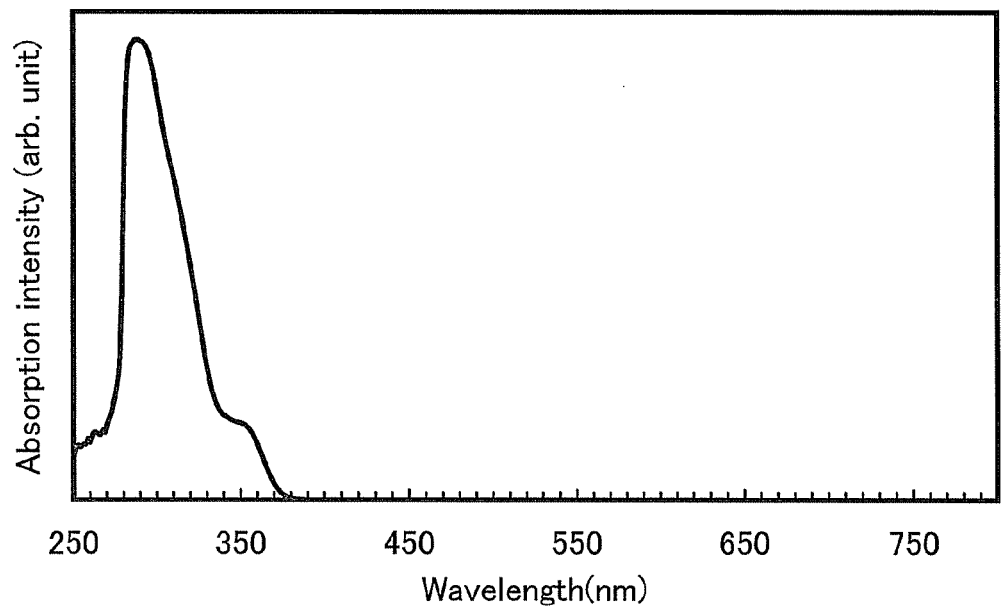
FIGS. 16A and 16B each show an absorption spectrum of DBTO11-III (abbreviation).
Figure 16B:
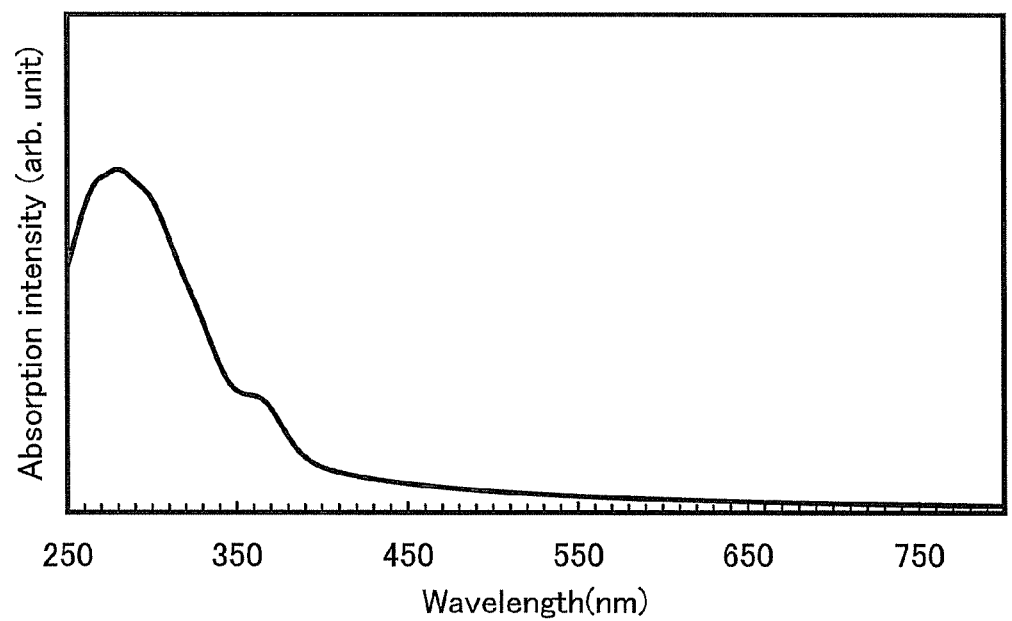

Further, FIG. 16A shows an absorption spectrum of DBTO11-III (abbreviation) in a toluene solution, and FIG. 16B shows an absorption spectrum of DBTO11-III (abbreviation) in a thin film. An ultraviolet-visible spectrophotometer (V-550, manufactured by JASCO Corporation) was used for the measurement. The absorption spectrum of DBTO11-III (abbreviation) in the toluene solution was obtained by subtracting the absorption spectra of quartz and toluene from the absorption spectrum of DBTO11-III (abbreviation) in the toluene solution in a quartz cell. In addition, the absorption spectrum of DBTO11-III (abbreviation) in the thin film was obtained by subtracting the absorption spectrum of quartz from the absorption spectrum of a sample formed by evaporating DBTO11-III (abbreviation) to a quartz substrate.

In FIG. 16A and FIG. 16B, the horizontal axis represents wavelength (nm) and the vertical axis represents absorption intensity (arbitrary unit). In the case of the toluene solution, absorption peaks were observed at around 349 nm and 289 nm, and in the case of the thin film, absorption peaks were observed at around 360 nm and 279 nm.

Figure 17A:
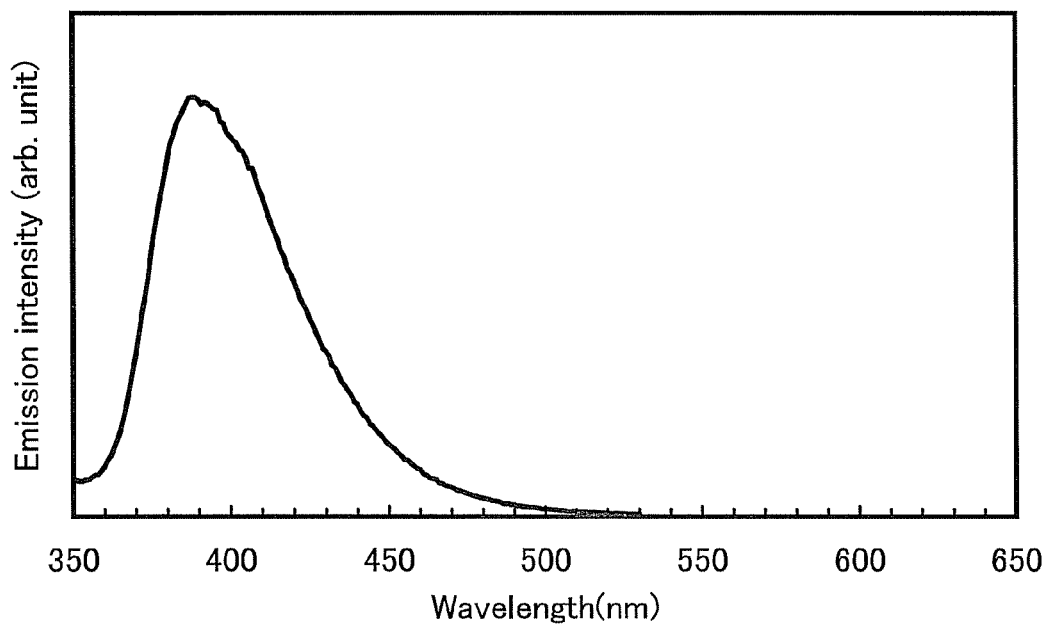
FIGS. 17A and 17B each show an emission spectrum of DBTO11-III (abbreviation).
Figure 17B:
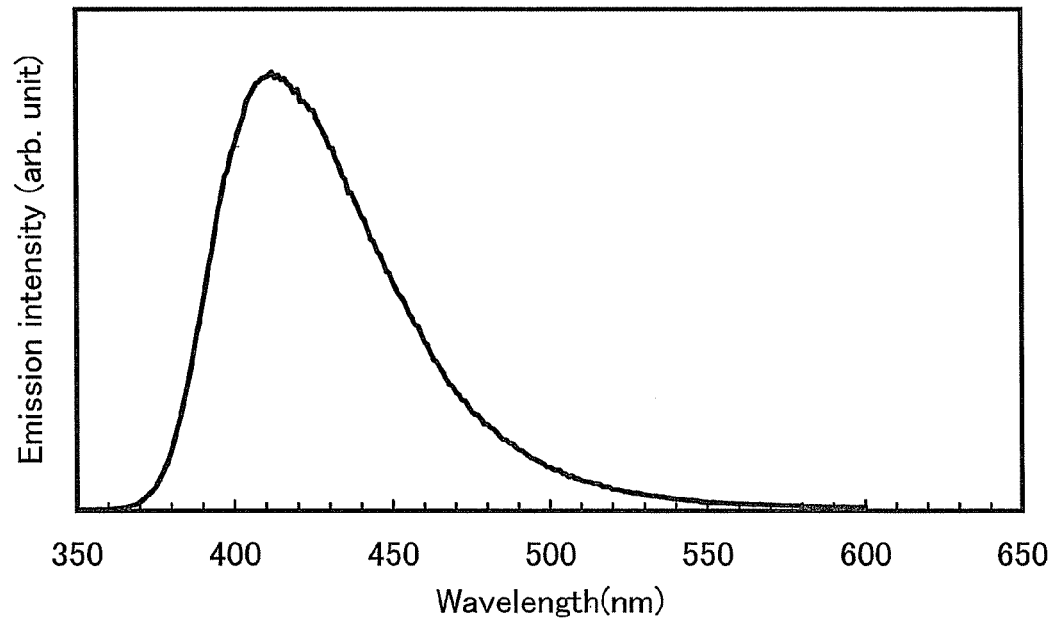

Further, FIG. 17A shows an emission spectrum of DBTO11-III (abbreviation) in the toluene solution (excitation wavelength: 290 nm). FIG. 17B shows an emission spectrum of DBTO11-III (abbreviation) in the thin film (excitation wavelength: 330 nm). In FIGS. 17A and 17B, the horizontal axis represents wavelength (nm) and the vertical axis represents emission intensity (arbitrary unit). The maximum emission wavelength was 388 nm in the case of the toluene solution (excitation wavelength: 290 nm), and 412 nm in the case of the thin film (excitation wavelength: 330 nm).

Further, by measurement with a photoelectron spectrometer (AC-2, manufactured by Riken Keiki, Co., Ltd.) in the atmosphere, the ionization potential of DBTO11-III (abbreviation) in the thin film was found to be 5.85 eV. As a result, the HOMO level was found to be −5.85 eV. Furthermore, with the use of the absorption spectrum data of DBTO11-III (abbreviation) in the thin film, the absorption edge was obtained by a Tauc plot assuming direct transition. The absorption edge was estimated as an optical energy gap, whereby the energy gap was 3.18 eV. From the obtained value of the energy gap and the HOMO level, the LUMO level was −2.67 eV.

Example 4

In Example 4, a method of synthesizing 2,5-bis[4-(dibenzothiophen-4-yl)phenyl]-1,3,4-oxadiazole (abbreviation: DBT2O11-II) represented by Structural Formula (200) in Embodiment 1 is specifically described.

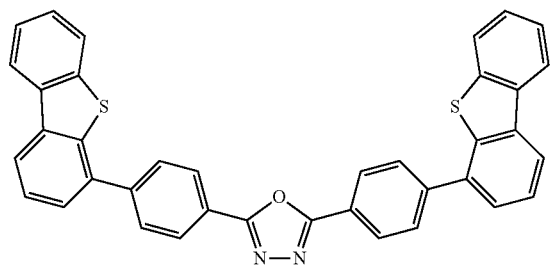

(200)

Synthesis of 2,5-bis[4-(dibenzothiophen-4-yl)phenyl]-1,3,4-oxadiazole (abbreviation: DBT2O11-II)

A synthesis scheme of 2,5-bis[4-(dibenzothiophen-4-yl)phenyl]-1,3,4-oxadiazole (abbreviation: DBT2O11-II) is illustrated in (E-1).

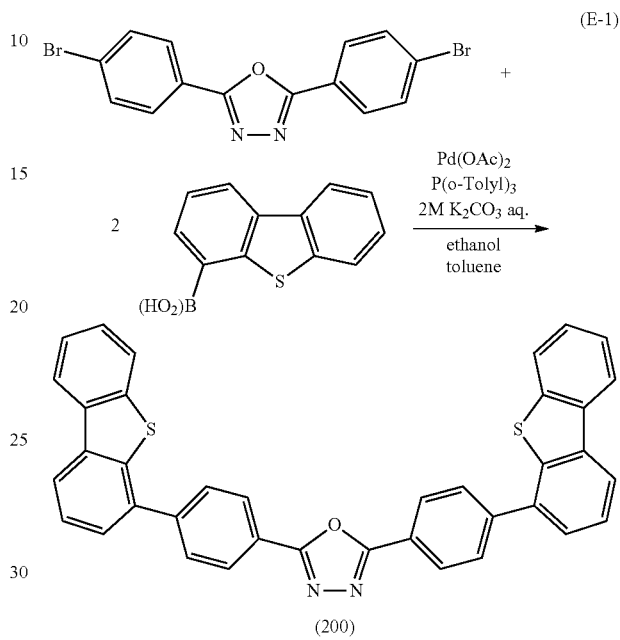

(E-1)

(200)

Into a 50-mL three neck flask were put 1.1 g (2.9 mmol) of 2,5-bis(4-bromophenyl)-1,3,4-oxadiazole, 1.4 g (6.1 mmol) of dibenzothiophene-4-boronic acid, and 91 mg (0.3 mmol) of tris(2-methylphenyl)phosphine, and the air in the flask was replaced with nitrogen. To this mixture were added 6.0 mL of a 2.0M aqueous potassium carbonate solution, 12 mL of toluene, and 4.0 mL of ethanol, and the mixture was degassed by being stirred under reduced pressure.

To this mixture was added 13 mg (0.1 mmol) of palladium (II) acetate, and the mixture was stirred at 80° C. for 7 hours under a nitrogen stream. After a predetermined time, the aqueous layer of the obtained mixture was extracted with chloroform. The obtained extract solution and the organic layer were combined, washed with saturated brine, and dried over magnesium sulfate. This mixture was separated by gravity filtration, and the filtrate was concentrated to give a solid. This solid was purified by silica gel column chromatography.

The column chromatography was performed using chloroform as a developing solvent. The obtained fraction was condensed to give a solid. The solid was recrystallized with toluene/hexane, so that 0.8 g of a white powder was obtained in 53% yield, which was the substance to be produced.

By a train sublimation method, 0.8 g of the obtained white powder was purified. The purification was performed under the following conditions: the temperature was 325° C.; the pressure was 2.4 Pa; and the flow rate of argon gas was 5 mL/min. Accordingly, 0.7 g of the compound was obtained at a yield of 88%.

In addition, the compound obtained through the above synthesis method was measured by a nuclear magnetic resonance (NMR) method. The measurement data are shown below. $^1$H NMR (CDCl$_3$, 300 MHz): δ (ppm)=7.47-7.53 (m, 4H), 7.55-7.65 (m, 4H), 7.85-7.89 (m, 2H), 7.97 (d, J=9.0 Hz, 4H), 8.20-8.24 (m, 4H), 8.35 (d, J=8.7 Hz, 4H).

Figure 18A:
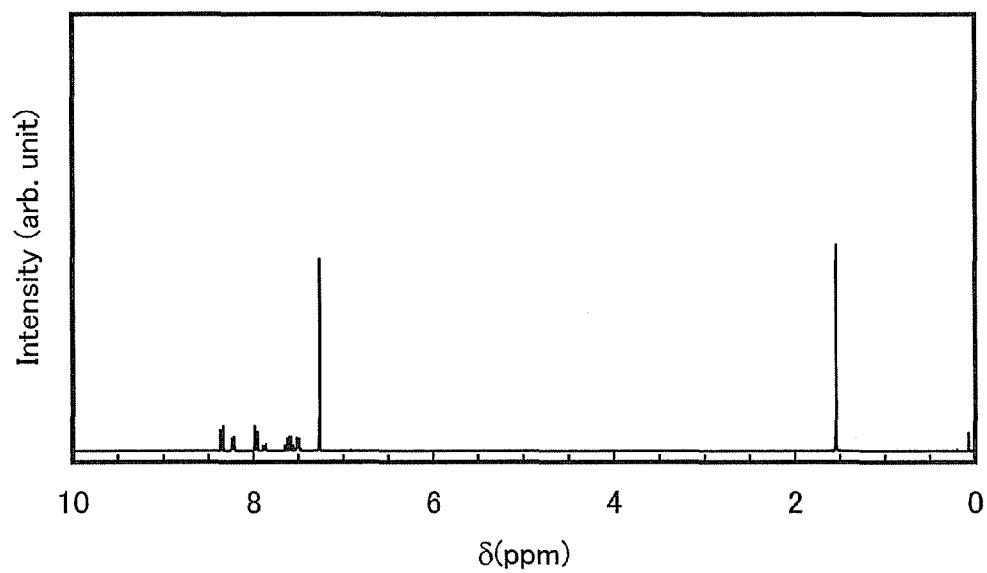
FIGS. 18A and 18B are NMR charts of DBT2O11-II (abbreviation).
Figure 18B:
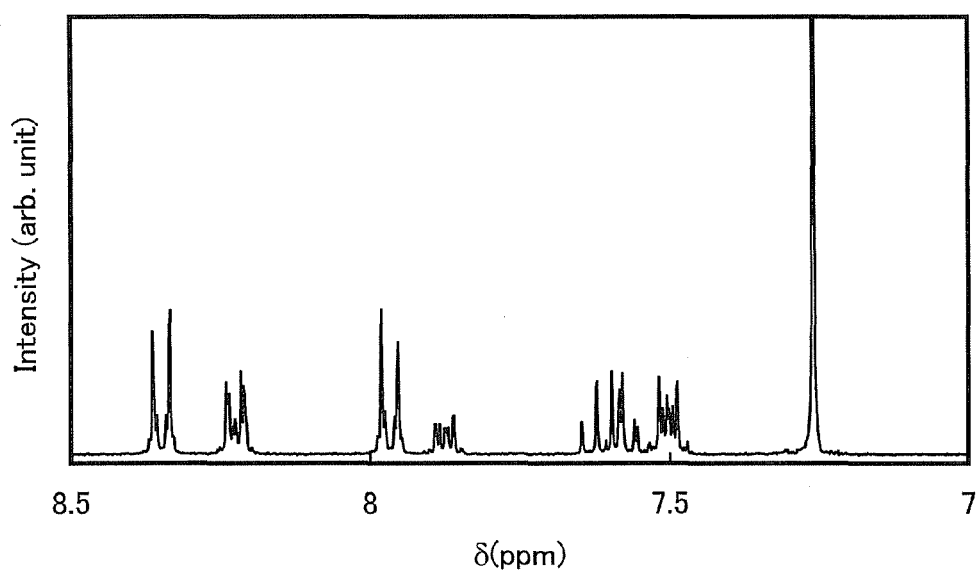

Further, ¹H NMR charts are shown in FIGS. 18A and 18B. Note that FIG. 18B is a chart where the range of 7.0 ppm to 8.5 ppm in FIG. 18A is enlarged. It was found from the measurement results that 2,5-bis[4-(dibenzothiophen-4-yl)phenyl]-1,3,4-oxadiazole (abbreviation: DBT2O11-II) represented by Structural Formula (200) above was obtained.

Figure 19A:
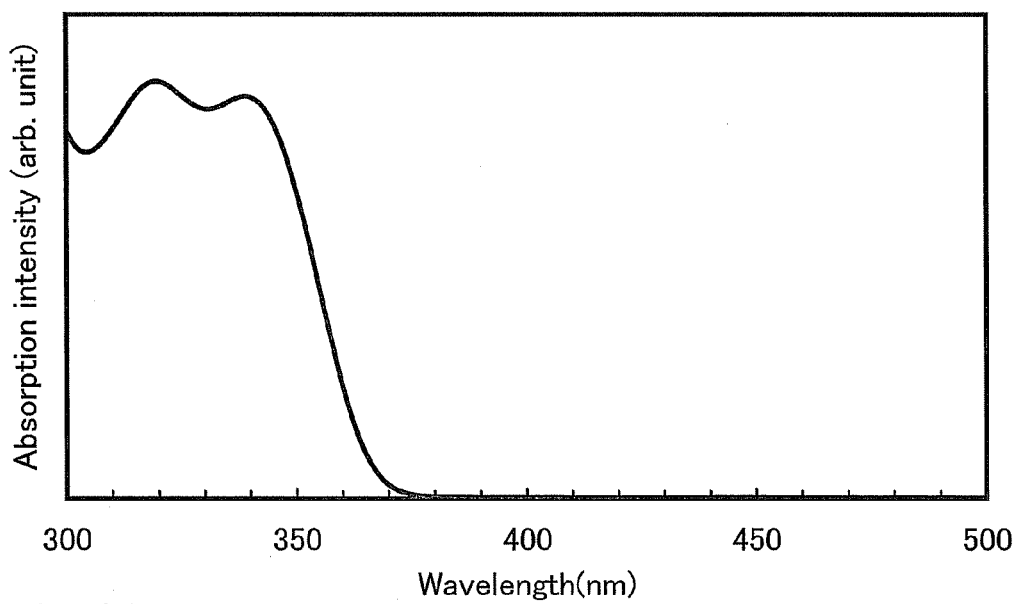
FIGS. 19A and 19B each show an absorption spectrum of DBT2O11-II (abbreviation).
Figure 19B:
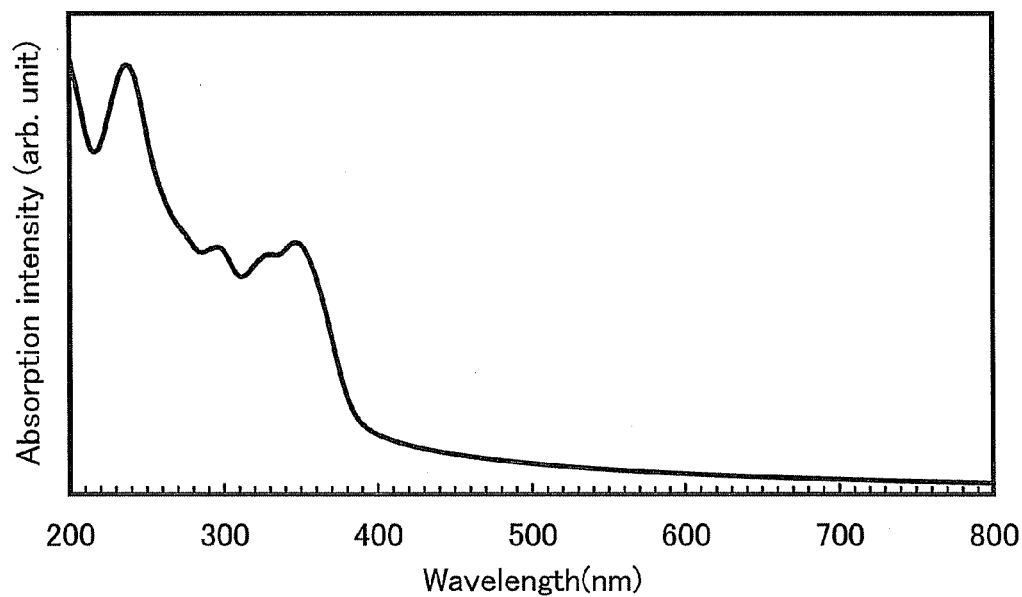

Further, FIG. 19A shows an absorption spectrum of DBT2O11-II (abbreviation) in a toluene solution, and FIG. 19B shows an absorption spectrum of DBT2O11-II (abbreviation) in a thin film. An ultraviolet-visible spectrophotometer (V-550, manufactured by JASCO Corporation) was used for the measurement. The absorption spectrum of DBT2O11-II (abbreviation) in the toluene solution was obtained by subtracting the absorption spectra of quartz and toluene from the absorption spectrum of DBT2O11-II (abbreviation) in the toluene solution in a quartz cell. In addition, the absorption spectrum of DBT2O11-II (abbreviation) in the thin film was obtained by subtracting the absorption spectrum of quartz from the absorption spectrum of a sample formed by evaporating DBT2O11-II (abbreviation) to a quartz substrate.

In FIG. 19A and FIG. 19B, the horizontal axis represents wavelength (nm) and the vertical axis represents absorption intensity (arbitrary unit). In the case of the toluene solution, absorption peaks were observed at around 342 nm, 339 nm, and 319 nm, and in the case of the thin film, absorption peaks were observed at around 347 nm, 329 nm, 297 nm, and 237 nm.

Figure 20A:
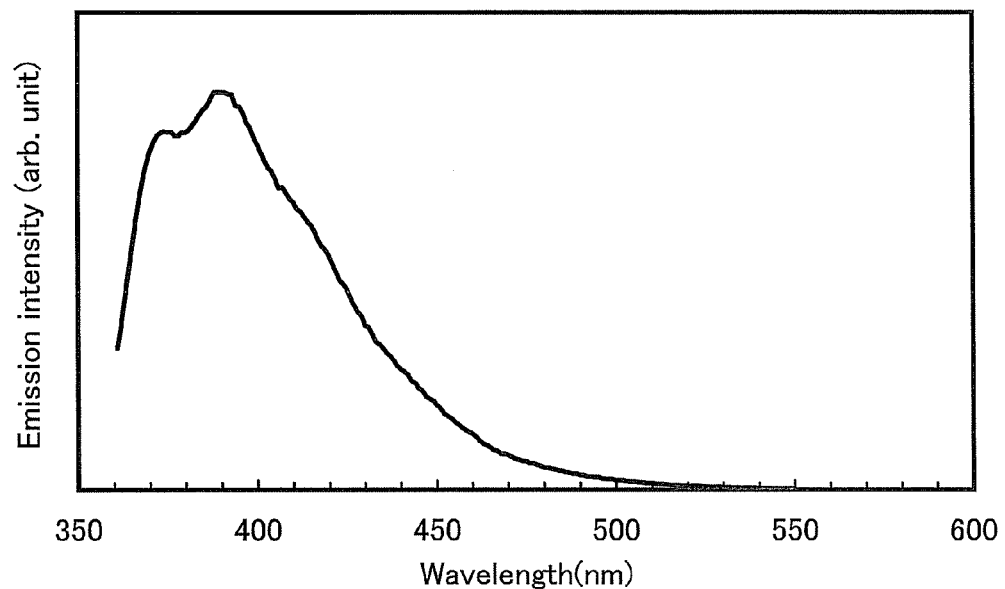
FIGS. 20A and 20B each show an emission spectrum of DBT2O11-II (abbreviation).
Figure 20B:
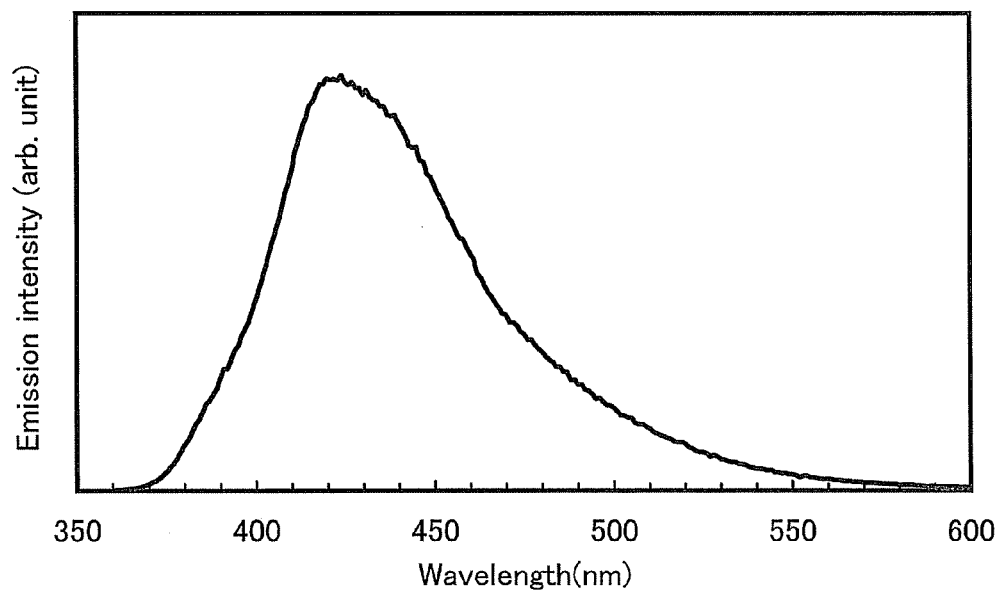

Further, FIG. 20A shows an emission spectrum of DBT2O11-II (abbreviation) in the toluene solution (excitation wavelength: 344 nm). FIG. 20B shows an emission spectrum of DBT2O11-II (abbreviation) in the thin film (excitation wavelength: 344 nm). In FIGS. 20A and 20B, the horizontal axis represents wavelength (nm) and the vertical axis represents emission intensity (arbitrary unit). The maximum emission wavelengths were 390 nm and 375 nm in the case of the toluene solution (excitation wavelength: 344 nm), and 425 nm in the case of the thin film (excitation wavelength: 344 nm).

Further, by measurement with a photoelectron spectrometer (AC-2, manufactured by Riken Keiki, Co., Ltd.) in the atmosphere, the ionization potential of DBT2O11-II (abbreviation) in the thin film was found to be 5.91 eV. As a result, the HOMO level was found to be −5.91 eV. Furthermore, with the use of the absorption spectrum data of DBT2O11-II (abbreviation) in the thin film, the absorption edge was obtained by a Tauc plot assuming direct transition. The absorption edge was estimated as an optical energy gap, whereby the energy gap was 3.26 eV. From the obtained value of the energy gap and the HOMO level, the LUMO level was −2.65 eV.

Example 5

In this example, described are a method for manufacturing a light-emitting element including any of the oxadiazole derivatives described in Embodiment 1 as a host material of a light-emitting layer and measurement results of element characteristics. Specifically, Light-Emitting Element 1 formed using 2,5-bis[4-(dibenzothiophen-4-yl)phenyl]-1,3,4-oxadiazole (abbreviation: DBT2O11-II) which is described in Example 4 and Light-Emitting Element 2 formed using 2-[4-(2,8-diphenyldibenzothiophen-4-yl)phenyl]-5-phenyl-1,3,4-oxadiazole (abbreviation: DBTO11-III) which is described in Example 3, will be described.

Figure 8:
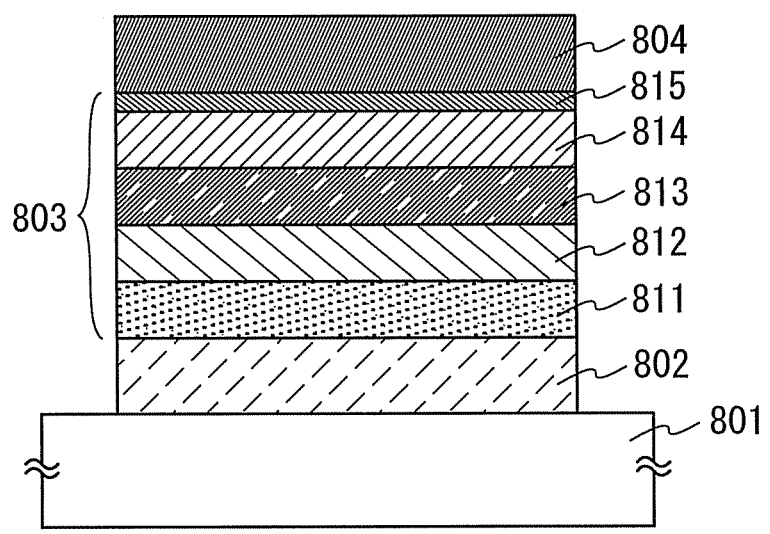
FIG. 8 illustrates an element structure of a light-emitting element in Example 5.

Note that each element structure of the light-emitting elements of this example is illustrated in FIG. 8, in which a light-emitting layer 813 is formed using any of the oxadiazole derivatives which are embodiments of the present invention. Structural formulae of organic compounds used in this example are shown below.

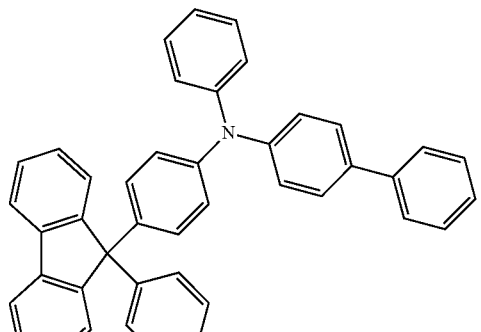

BPAFLP

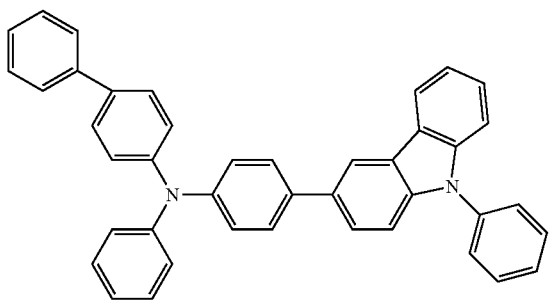

PCBA1BP

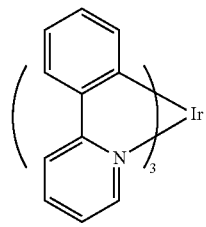

Ir(ppy)₃

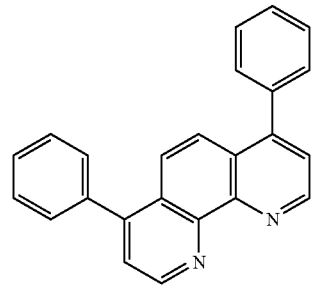

BPhen

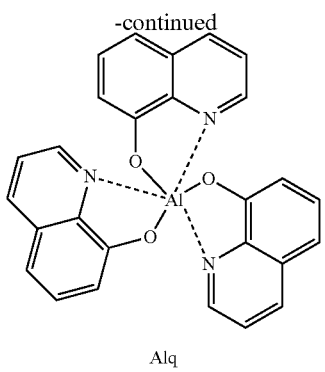

Alq

First, a film of indium tin oxide containing silicon oxide (ITSO) was deposited on a substrate 801 which was a glass substrate by a sputtering method to form a first electrode 802. The thickness was 110 nm and the electrode area was 2 mm×2 mm. In this example, the first electrode 802 was manufactured as an anode.

Next, an EL layer 803 in which a plurality of layers were stacked was formed over the first electrode 802. In this example, the EL layer 803 has a structure in which a first layer 811 which is a hole-injection layer, a second layer 812 which is a hole-transport layer, a third layer 813 which is a light-emitting layer, a fourth layer 814 which is an electron-transport layer, and a fifth layer 815 which is an electron-injection layer are sequentially stacked.

The substrate 801 provided with the first electrode 802 was fixed on a substrate holder that was provided in a vacuum evaporation apparatus so that a surface provided with the first electrode 802 faced downward. The pressure in the vacuum evaporation apparatus was reduced to approximately $10^{-4}$ Pa. Then, on the first electrode 802, 4-phenyl-4'-(9-phenylfluoren-9-yl)triphenylamine (abbreviation: BPAFLP) and molybdenum(VI) oxide were co-evaporated to form the first layer 811 which is the hole-injection layer. The thickness of the first layer 811 was 50 nm, and the evaporation rate was controlled so that the weight ratio of BPAFLP to molybdenum oxide was 4:2 (=BPAFLP:molybdenum oxide). Note that the co-evaporation method refers to an evaporation method in which evaporation is carried out from a plurality of evaporation sources at the same time in one treatment chamber.

Next, a 10-nm-thick film of a hole-transport material was formed on the first layer 811 by an evaporation method with resistance heating to form the second layer 812 which is the hole-transport layer. Note that for the second layer 812, 4-phenyl-4'-(9-phenylfluoren-9-yl)triphenylamine (abbreviation: BPAFLP) was used.

Next, the third layer 813 which is the light-emitting layer was formed over the second layer 812 by an evaporation method using resistance heating. In the case where Light-Emitting Element 1 is formed, a first film with a thickness of 20 nm was formed by co-evaporation of 2,5-bis[4-(dibenzothiophen-4-yl)phenyl]-1,3,4-oxadiazole (abbreviation: DBT2O11-II) as a first host material, 4-phenyl-4'-(9-phenyl-9H-carbazol-3-yl)triphenylamine (abbreviation: PCBA1BP) as a second host material, and tris(2-phenylpyridinato-$N,C^{2'}$)iridium(III) (abbreviation: Ir(ppy)$_3$) as a guest material. Note that the evaporation rate was controlled so that the weight ratio of DBT2O11-II (abbreviation) to PCBA1BP (abbreviation) and Ir(ppy)$_3$ (abbreviation) was 1:0.25:0.08 (=DBT2O11-II:PCBA1BP:Ir(ppy)$_3$).

Further, a second film with a thickens of 20 nm was formed by co-evaporation of 2,5-bis[4-(dibenzothiophen-4-yl)phenyl]-1,3,4-oxadiazole (abbreviation: DBT2O11-II) as a host material and tris(2-phenylpyridinato-$N,C^{2'}$)iridium(III) (abbreviation: Ir(ppy)$_3$) as a guest material. Note that the evaporation rate was controlled so that the weight ratio of DBT2O11-II (abbreviation) to Ir(ppy)$_3$ (abbreviation) was 1:0.08 (=DBT2O11-II:Ir(ppy)$_3$). In other words, in Light-Emitting Element 1, the third layer 813 in which the first film and the second film were stacked was formed.

In the case where Light-Emitting Element 2 is formed, a first film with a thickness of 20 nm was formed by co-evaporation of 2-[4-(2,8-diphenyldibenzothiophen-4-yl)phenyl]-5-phenyl-1,3,4-oxadiazole (abbreviation: DBTO11-III) as a first host material, 4-phenyl-4'-(9-phenyl-9H-carbazol-3-yl)triphenylamine (abbreviation: PCBA1BP) as a second host material, and tris(2-phenylpyridinato-$N,C^{2'}$)iridium(III) (abbreviation: Ir(ppy)$_3$) as a guest material. Note that the evaporation rate was controlled so that the weight ratio of DBTO11-III (abbreviation) to PCBA1BP (abbreviation) and Ir(ppy)$_3$ (abbreviation) was 1:0.25:0.08 (=DBTO11-III:PCBA1BP:Ir(ppy)$_3$).

Further, a second film with a thickens of 20 nm was formed by co-evaporation of 2-[4-(2,8-diphenyldibenzothiophen-4-yl)phenyl]-5-phenyl-1,3,4-oxadiazole (abbreviation: DBTO11-III) as a host material and tris(2-phenylpyridinato-$N,C^{2'}$)iridium(III) (abbreviation: Ir(ppy)$_3$) as a guest material. Note that the evaporation rate was controlled so that the weight ratio of DBTO11-III (abbreviation) to Ir(ppy)$_3$ (abbreviation) was 1:0.08 (=DBTO11-III:Ir(ppy)$_3$). In other words, in Light-Emitting Element 2, the third layer 813 in which the first film and the second film were stacked was formed.

Furthermore, on the third layer 813, a 15-nm-thick film of tris(8-quinolinolato)aluminum(III) (abbreviation: Alq) and, thereon, a 15-nm-thick film of bathophenanthroline (abbreviation: BPhen) were formed to form the fourth layer 814 which is the electron-transport layer.

On the fourth layer 814, the fifth layer 815 which is the electron-injection layer was formed by depositing lithium fluoride (LiF) to a thickness of 1 nm.

Lastly, a 200-nm-thick film of aluminum was formed by an evaporation method using resistance heating to form a second electrode 804. Thus, Light-Emitting Elements 1 and 2 were formed.

Table 1 shows element structures of Light-Emitting Elements 1 and 2 obtained through the above-described steps.

TABLE 1

|  | First Electrode 802 | First Layer (Hole-Injection Layer) 811 | Second Layer (Hole-Transport Layer) 812 |
| --- | --- | --- | --- |
| Light-Emitting Element 1 | ITSO 110 nm | BPAFLP:MoOx (=4:2) 50 nm | BPAFLP 10 nm |
| Light-Emitting Element 2 | ITSO 110 nm | BPAFLP: MoOx (=4:2) 50 nm | BPAFLP 10 nm |

|  | Third Layer (Light-Emitting Layer) 813 | |
| --- | --- | --- |
| Light-Emitting Element 1 | DBT2O11II:PCBA1BP:Ir(ppy)$_3$ (=1:0.25:0.08) 20 nm | DBT2O11II:Ir(ppy)$_3$ (=1:0.08) 20 nm |
| Light-Emitting Element 2 | DBTO11III:PCBA1BP:Ir(ppy)$_3$ (=1:0.25:0.08) 20 nm | DBTO11III:Ir(ppy)$_3$ (=1:0.08) 20 nm |

TABLE 1-continued

| | Fourth Layer (Electron-Transport Layer) 814 | Fifth Layer (Electron-Injection Layer) 815 | Second Electrode 804 |
|---|---|---|---|
| Light-Emitting Element 1 | Alq 15 nm | BPhen 15 nm | LiF 1 nm | Al 200 nm |
| Light-Emitting Element 2 | Alq 15 nm | BPhen 15 nm | LiF 1 nm | Al 200 nm |

*Mixture ratios are all represented in weight ratios.

Light-Emitting Elements 1 and 2 were sealed in a glove box under a nitrogen atmosphere without being exposed to the air. Then, the operation characteristics of these light-emitting elements were measured. Note that the measurement was carried out at room temperature (in an atmosphere kept at 25° C.).

Table 2 shows voltage (V), current density (mA/cm$^2$), CIE chromaticity coordinates (x, y), luminance (cd/m$^2$), and current efficiency (cd/A) of each of Light-Emitting Elements 1 and 2 at a luminance of about 1000 cd/m$^2$.

TABLE 2

| | Voltage (V) | Current Density (mA/cm$^2$) | Chromaticity (x, y) | Luminance (cd/m$^2$) | Current Efficiency (cd/A) |
|---|---|---|---|---|---|
| Light-Emitting Element 1 | 3.2 | 2.6 | (0.34, 0.61) | 860 | 32.6 |
| Light-Emitting Element 2 | 3.0 | 1.6 | (0.34, 0.61) | 845 | 52.0 |

Figure 21:
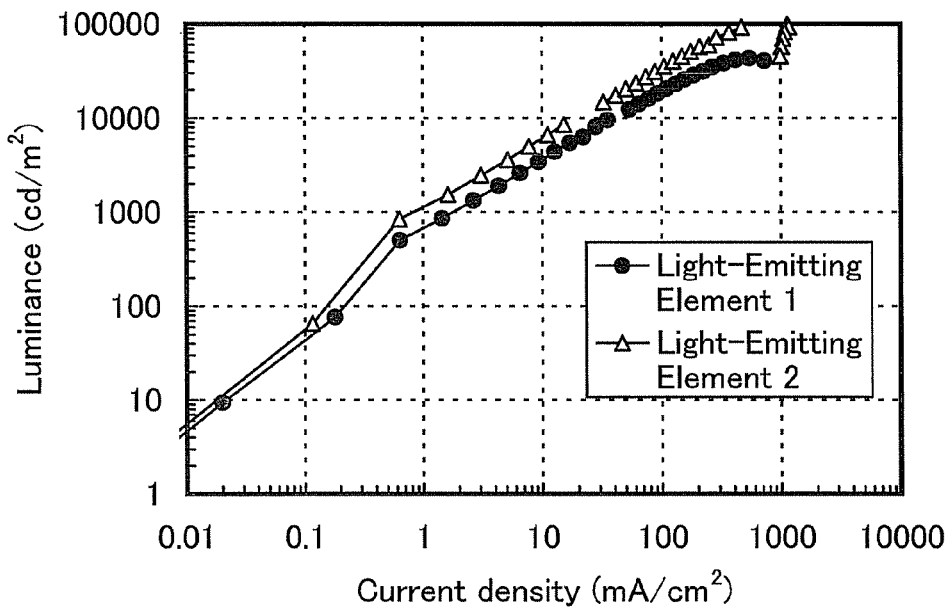
FIG. 21 shows current density vs. luminance characteristics of Light-Emitting Elements 1 and 2.
Figure 22:
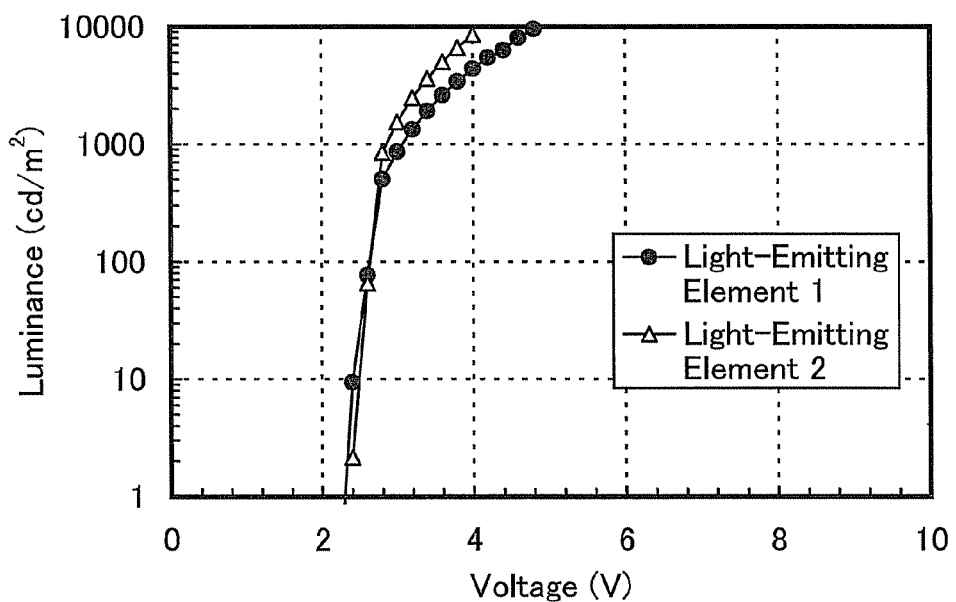
FIG. 22 shows voltage vs. luminance characteristics of Light-Emitting Elements 1 and 2.
Figure 23:
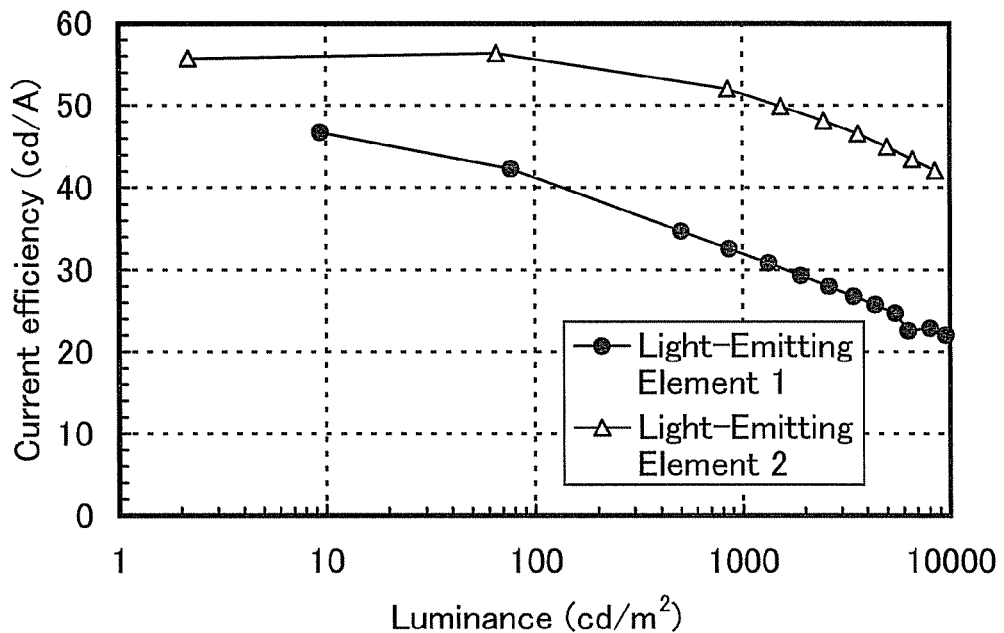
FIG. 23 shows luminance vs. current efficiency characteristics of Light-Emitting Elements 1 and 2.
Figure 24:
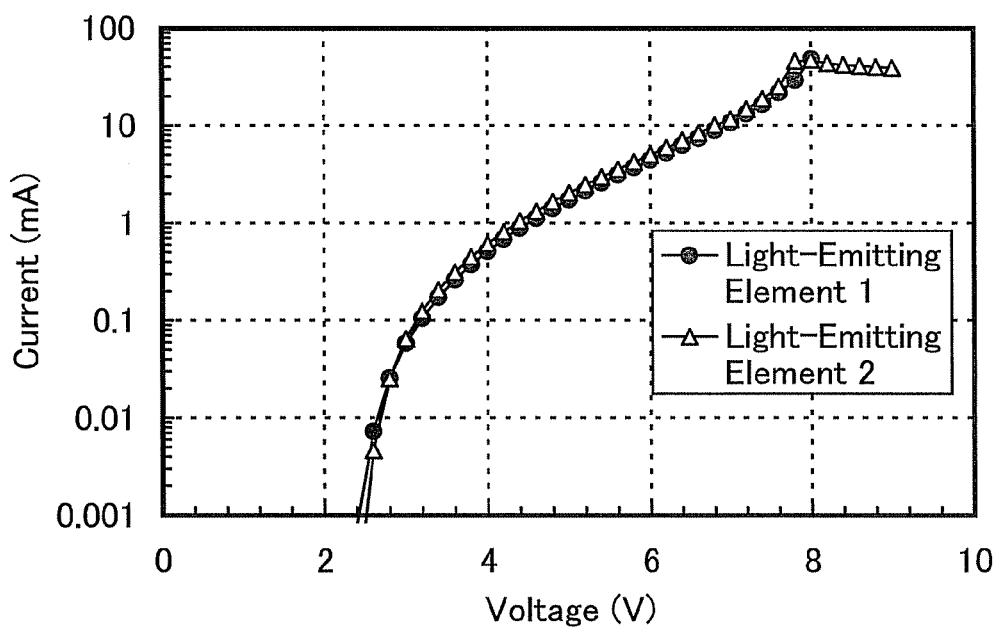
FIG. 24 shows voltage vs. current characteristics of Light-Emitting Elements 1 and 2.

FIG. 21 shows current density vs. luminance characteristics of Light-Emitting Elements 1 and 2; FIG. 22 shows voltage vs. luminance characteristics thereof; FIG. 23 shows luminance vs. current efficiency characteristics thereof; and FIG. 24 shows voltage vs. current characteristics thereof. In FIG. 21, the vertical axis represents luminance (cd/m$^2$) and the horizontal axis represents current density (mA/cm$^2$). In FIG. 22, the vertical axis represents luminance (cd/m$^2$) and the horizontal axis represents voltage (V). In FIG. 23, the vertical axis represents current efficiency (cd/A) and the horizontal axis represents luminance (cd/m$^2$). In FIG. 24, the vertical axis represents current (mA) and the horizontal axis represents voltage (V).

From FIG. 23, the maximum current efficiency of Light-Emitting Element 1 is 47 cd/A, and the maximum current efficiency of Light-Emitting Element 2 is 56 cd/A. This demonstrates that the light-emitting element including the oxadiazole derivative which is one embodiment of the present invention has extremely high efficiency.

Figure 25:
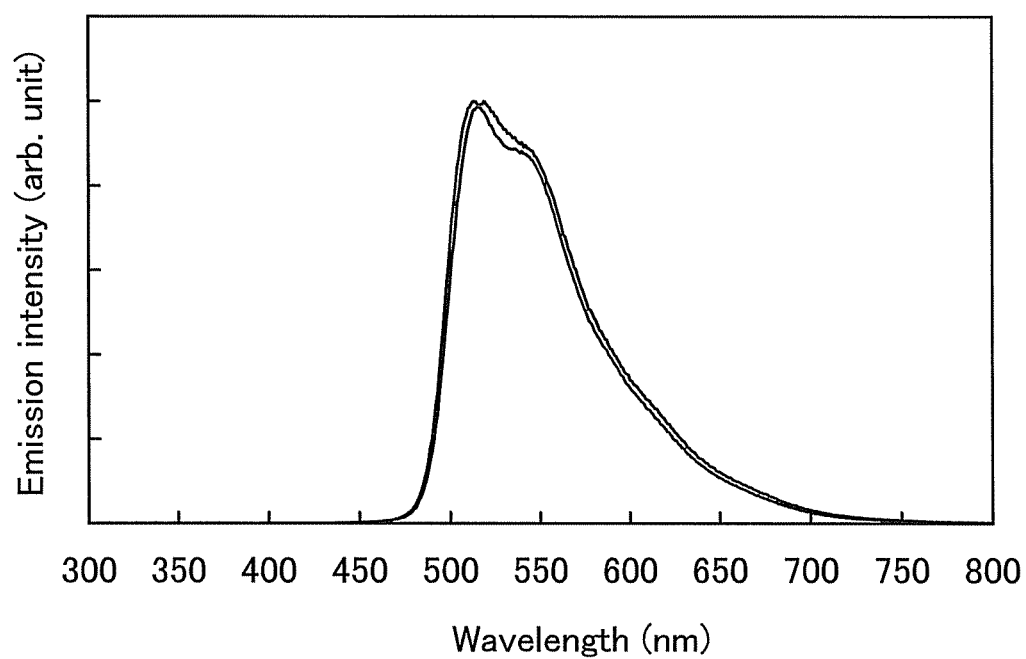
FIG. 25 shows emission spectra of Light-Emitting Elements 1 and 2.

FIG. 25 shows emission spectra of Light-Emitting Elements 1 and 2. As shown in FIG. 25, in each case of Light-Emitting Elements 1 and 2, an emission wavelength derived from Ir(ppy)$_3$ (abbreviation) which was used as the guest material was observed, whereas emission wavelengths derived from the oxadiazole derivative which is one embodiment of the present invention (DBT2O11-II (abbreviation) or DBTO11-III (abbreviation)) which was used as the host material and PCBA1BP (abbreviation) which was used as the second host material were not observed. Thus, it was confirmed that the oxadiazole derivative which is one embodiment of the present invention served as the host material of the light-emitting layer of the light-emitting element.

Reference Example

In this reference example, an example of synthesizing 4-phenyl-4'-(9-phenylfluoren-9-yl)triphenylamine (abbreviation: BPAFLP) used as a material of Light-Emitting Element 1 will be described.

Step 1: Method of Synthesizing 9-(4-bromophenyl)-9-phenylfluorene

In a 100-mL three-neck flask, 1.2 g (50 mmol) of magnesium was heated and stirred for 30 minutes under reduced pressure to be activated. This was cooled to room temperature, and the flask was made to contain a nitrogen atmosphere. Then, several drops of dibromoethane were added, so that foam formation and heat generation were confirmed. After 12 g (50 mmol) of 2-bromobiphenyl dissolved in 10 mL of dehydrated diethyl ether was slowly added dropwise to this mixture, the mixture was heated and stirred under reflux for 2.5 hours, so that a Grignard reagent was prepared.

Into a 500-mL three-neck flask were placed 10 g (40 mmol) of 4-bromobenzophenone and 100 mL of dehydrated diethyl ether. After the Grignard reagent which was synthesized in advance was slowly added dropwise to this mixture, the mixture was heated and stirred under reflux for 9 hours.

After reaction, this mixture solution was filtered to give a residue. The obtained residue was dissolved in 150 mL of ethyl acetate, and 1N-hydrochloric acid was added to the mixture until it was made acid, which was then stirred for 2 hours. The organic layer of this liquid was washed with water, and magnesium sulfate was added thereto to remove moisture. This suspension was filtered, and the obtained filtrate was concentrated to give a highly viscous substance. Into a 500-mL recovery flask were placed this highly viscous substance, 50 mL of glacial acetic acid, and 1.0 mL of hydrochloric acid. The mixture was stirred and heated at 130° C. for 1.5 hours under a nitrogen atmosphere to be reacted.

After the reaction, this reaction mixture solution was filtered to give a residue. The obtained residue was washed with water, an aqueous sodium hydroxide solution, water, and methanol in this order. Then, the mixture was dried, so that the substance which was the object of the synthesis was obtained as 11 g of a white powder in 69% yield. The synthesis scheme of Step 1 is illustrated in the following (J-1).

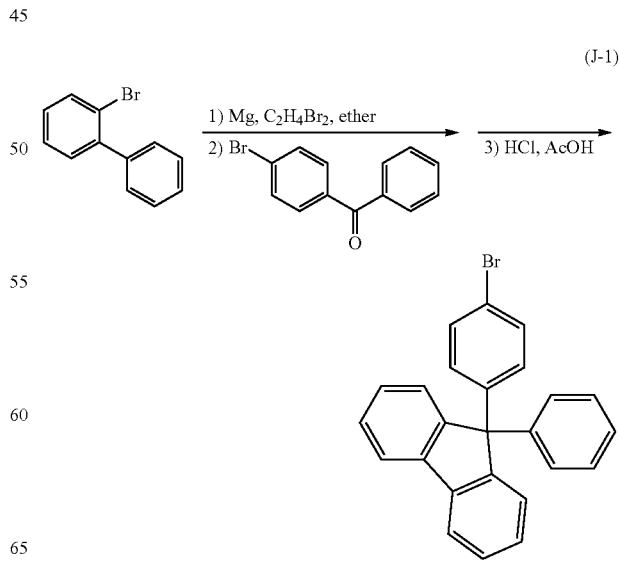

Step 2: Method of Synthesizing 4-phenyl-4'-(9-phenylfluoren-9-yl)triphenylamine (abbreviation: BPAFLP)

Into a 100-mL three-neck flask were placed 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0), and the air in the flask was replaced with nitrogen. Then, 20 mL of dehydrated xylene was added to this mixture. After the mixture was degassed by being stirred under reduced pressure, 0.2 mL (0.1 mmol) of tri(tert-butyl)phosphine (a 10 wt % hexane solution) was added to the mixture. This mixture was stirred and heated at 110° C. for 2 hours under a nitrogen atmosphere to be reacted.

After the reaction, 200 mL of toluene was added to this reaction mixture solution, and this suspension was filtered through Florisil (produced by Wako Pure Chemical Industries, Ltd., Catalog No. 540-00135) and Celite (produced by Wako Pure Chemical Industries, Ltd., Catalog No. 531-16855). The obtained filtrate was concentrated, and the resulting substance was purified by silica gel column chromatography (with a developing solvent of toluene and hexane in a 1:4 ratio). The obtained fraction was concentrated, and acetone and methanol were added to the mixture. The mixture was irradiated with ultrasonic waves and then recrystallized, so that the substance which was the object of the synthesis was obtained as 4.1 g of a white powder in 92% yield. The synthesis scheme of Step 2 is illustrated in the following (J-2).

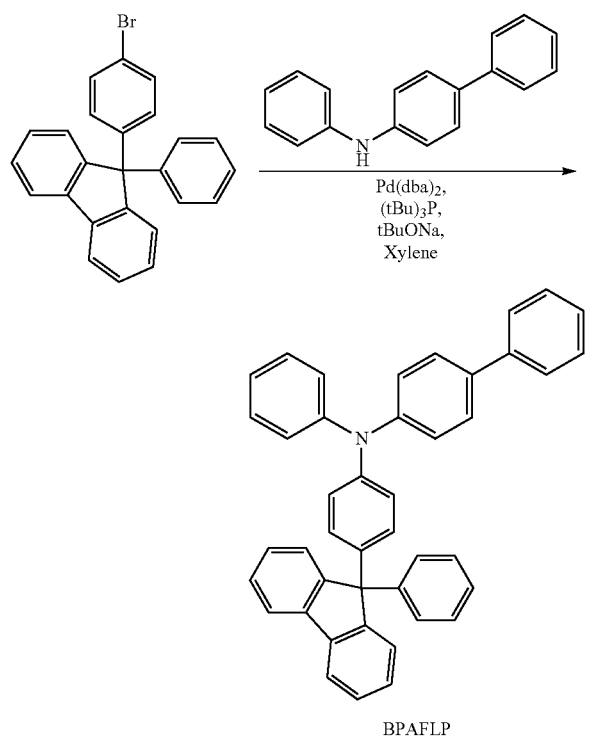

(J-2)

The Rf values of the substance that was the object of the synthesis, 9-(4-bromophenyl)-9-phenylfluorene, and 4-phenyl-diphenylamine were respectively 0.41, 0.51, and 0.27, which were found by silica gel thin layer chromatography (TLC) (with a developing solvent of ethyl acetate and hexane in a 1:10 ratio).

This compound was identified as 4-phenyl-4'-(9-phenylfluoren-9-yl)triphenylamine (abbreviation: BPAFLP), which was the object of the synthesis, by a nuclear magnetic resonance (NMR) method.

$^1$H NMR data of the obtained compound are shown below.

$^1$H NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9, 2H).

This application is based on Japanese Patent Application serial no. 2010-257739 filed with Japan Patent Office on Nov. 18, 2010, the entire contents of which are hereby incorporated by reference.

What is claimed is:

1. An oxadiazole derivative represented by General Formula (G1),

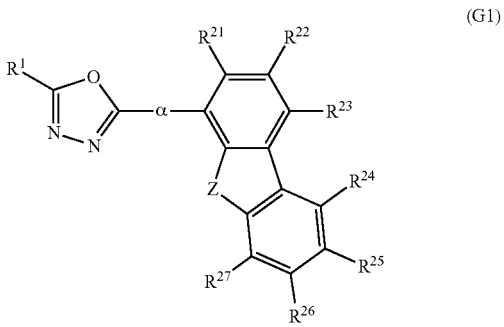

(G1)

wherein:

$R^1$ represents an alkyl group having 1 to 4 carbon atoms, or a substituted or unsubstituted aryl group having 6 to 13 carbon atoms;

$R^{21}$ to $R^{27}$ separately represent a hydrogen atom, an alkyl group having 1 to 4 carbon atoms, or a substituted or unsubstituted aryl group having 6 to 13 carbon atoms;

α represents a substituted or unsubstituted arylene group having 6 to 13 carbon atoms; and Z represents a sulfur atom or an oxygen atom.

2. The oxadiazole derivative according to claim 1, wherein α represents a substituted or unsubstituted biphenyldiyl group.

3. The oxadiazole derivative according to claim 1, wherein α represents a substituted phenylene group.

4. The oxadiazole derivative according to claim 1, wherein α represents any one of structures represented by Structural Formulae (1-1) to (1-15),

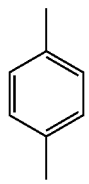

(1-1)

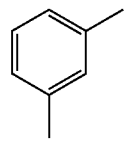

(1-2)

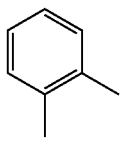
(1-3)
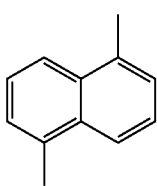
(1-4)
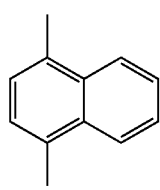
(1-5)
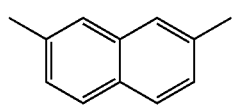
(1-6)
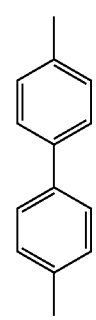
(1-7)
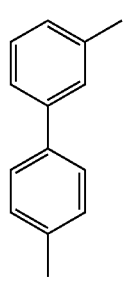
(1-8)
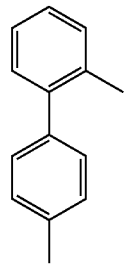
(1-9)
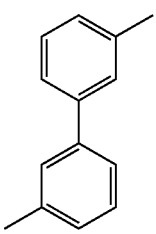
(1-10)
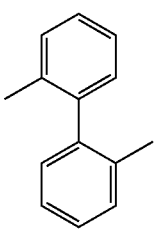
(1-11)
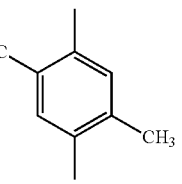
(1-12)
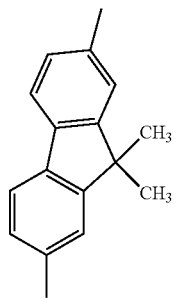
(1-13)

(1-14)

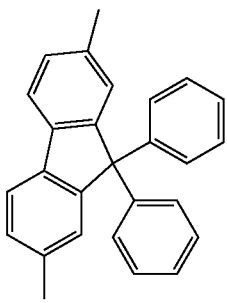

(1-15)

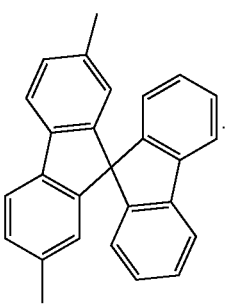

5. A light-emitting element comprising the oxadiazole derivative according to claim 1.

6. A light-emitting device comprising the light-emitting element according to claim 5.

7. A lighting device comprising the light-emitting device according to claim 6.

8. An electronic device comprising the light-emitting device according to claim 6.

9. An oxadiazole derivative represented by General Formula (G1-1),

(G1-1)

wherein:
$R^1$ represents an alkyl group having 1 to 4 carbon atoms, or a substituted or unsubstituted aryl group having 6 to 13 carbon atoms;
$R^{21}$ to $R^{27}$ separately represent a hydrogen atom, an alkyl group having 1 to 4 carbon atoms, or a substituted or unsubstituted aryl group having 6 to 13 carbon atoms; and
Z represents a sulfur atom or an oxygen atom.

10. A light-emitting element comprising the oxadiazole derivative according to claim 9.

11. A light-emitting device comprising the light-emitting element according to claim 10.

12. A lighting device comprising the light-emitting device according to claim 11.

13. An electronic device comprising the light-emitting device according to claim 11.

* * * * *

UNITED STATES PATENT AND TRADEMARK OFFICE
CERTIFICATE OF CORRECTION

PATENT NO. : 8,563,740 B2  
APPLICATION NO. : 13/297937  
DATED : October 22, 2013  
INVENTOR(S) : Yuko Kawata et al.

Page 1 of 1

It is certified that error appears in the above-identified patent and that said Letters Patent is hereby corrected as shown below:

In the Specification:

Column 1, line 33; Change "fowled." to --formed.--.
Column 3, line 44; Change "(I-1)" to --(1-1)--.
Column 69, Structural Formula (364);

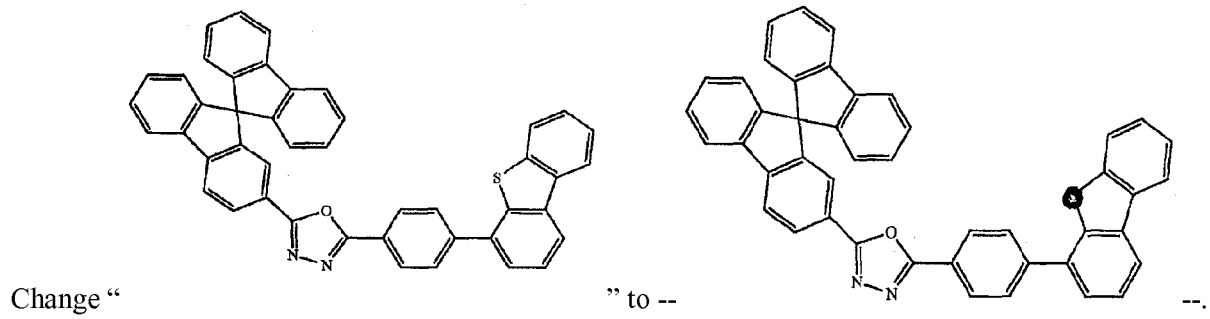

Column 85, Structural Formula (A-1);

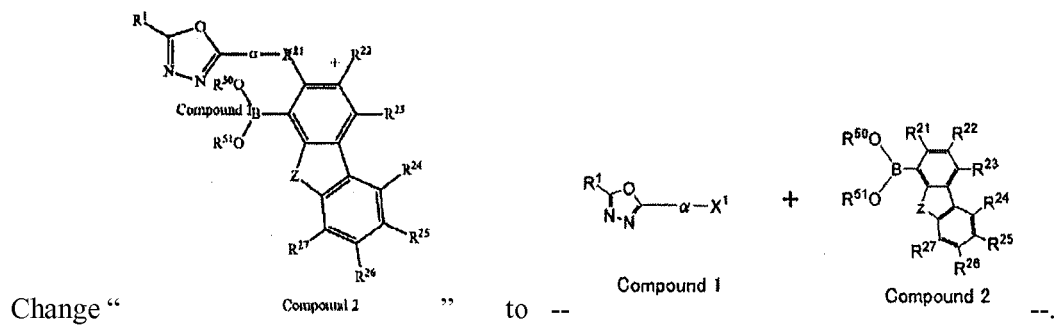

Column 94, line 25; Change "foamed" to --formed--.

Signed and Sealed this  
Thirty-first Day of December, 2013

Margaret A. Focarino  
*Commissioner for Patents of the United States Patent and Trademark Office*